US006335426B1

(12) United States Patent
Shanafelt et al.

(10) Patent No.: US 6,335,426 B1
(45) Date of Patent: *Jan. 1, 2002

(54) T-CELL SELECTIVE INTERLEUKIN-4 AGONISTS

(75) Inventors: Armen B. Shanafelt, Moraga; Jeffrey M. Greve, Berkeley; Robert Gundel, Alamo, all of CA (US)

(73) Assignee: Bayer Corporation, Berkeley, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/298,374

(22) Filed: Apr. 23, 1999

Related U.S. Application Data

(63) Continuation-in-part of application No. 08/874,697, filed on Jun. 13, 1997, now Pat. No. 5,986,059.
(60) Provisional application No. 60/036,746, filed on Jan. 27, 1997, and provisional application No. 60/019,748, filed on Jun. 14, 1996.

(51) Int. Cl.[7] .......................... C07K 1/00; C07K 14/00; C07K 17/00; A61K 45/00; A01N 37/18

(52) U.S. Cl. .......................... 530/351; 530/350; 514/2; 424/85.2

(58) Field of Search .................. 530/350, 351; 424/85.2; 514/2

(56) References Cited

U.S. PATENT DOCUMENTS

| 5,013,824 A | 5/1991 | Abrams et al. ............. 530/300 |
| 5,017,691 A | 5/1991 | Lee et al. .................. 535/351 |
| 5,506,107 A | 4/1996 | Cunningham et al. ...... 435/721 |
| 5,723,118 A | 3/1998 | Sebald ....................... 530/351 |

FOREIGN PATENT DOCUMENTS

| WO | 8702990 | 5/1987 | ........... C07K/15/00 |
| WO | 9221029 | 11/1992 | ........... C07K/13/00 |
| WO | 9310235 | 5/1993 | ........... C12N/15/24 |
| WO | 9321308 | 10/1993 | ........... C01N/13/00 |
| WO | 9400491 | 1/1994 | ........... C07K/13/00 |
| WO | 6527732 | 10/1995 | ........... C07K/14/00 |
| WO | 9527052 | 10/1995 | ........... C12N/15/00 |
| WO | 9604306 | 2/1996 | ........... C07K/14/55 |
| WO | 9604388 | 2/1996 | ........... C12N/15/62 |
| WO | 9609323 | 3/1996 | ........... C07K/14/54 |

OTHER PUBLICATIONS

Aversa, G., et al., "An interleukin–4 (IL–4) mutant protein inhibits both IL–4 or IL–13 induced human immunoglobulin G4 (IgG4) and IgE Synthesis and B cell proliferation: support for a common component shared by IL–4 and IL–13 receptors", J. Exp. Med., 178: 2213–2218 (1993).

Bowie, J. U., et al., "Deciphering the Message in Protein Sequences: Tolerance to Amino Acid Substitutions", Science, 247: 1306–1310 (Mar. 1990).

Callard, R., et al., "IL–4 and IL–13 receptors: are they one and the same?", Immunology Today, 17(3): 108–110 (1996).

Carr, C., et al., "Disulfide Assignments in Recombinant Mouse and Human Interleukin 4", Biochemistry, 30: 1515–1523 (1991).

Economides, A., et al., "Designer cytokines: targeting actions to cells of choice", Science, 270: 1351–1353 (1995).

Frömmel, C., et al., "An Estimate on the Effect of Point Mutation and Natural Selection on the Rate of Amino Acid Replacement in Proteins", J. Mol. Evol., 21:233–257 (1985).

George, D. G., et al., "Current Methods in Sequence Comparison and Analysis", Macromolecular Sequencing and Synthesis. Selected Methods and Applications, pp. 127–149 (1988).

Hilton, D., et al., "Cloning and characterization of a binding subunit of the interleukin–13 receptor that is also a component of the interleukin–4 receptor", PNAS–USA, 93: 497–501 (1996).

Kaushansky, K., et al., "Hematopoietic growth factors: understanding functional diversity in structural terms", Blood, 82(11): 3229–3240 (1993).

Kondo, M., et al., "Sharing of the interleukin–2 (IL–2) receptor g chain between receptors for IL–2 and IL–4", Science, 262: 1874–1877 (1993).

Kruse, N., et al., "Two distinct functional sites of human interleukin–4 are identified by variants impaired in either receptor binding or receptor activation", EMBO J., 12(13): 5121–5129 (1993).

Kruse, N., et al., "Conversion of human interleukin–4 into a high affinity antagonist by a single amino acid replacement", EMBO J., 11(9): 3237–3244 (1992).

Kruse, N., et al., "Site–directed mutagenesis reveals the importance of disulfide bridges and aromatic residues for structure and proliferative activity of human Interleukin–4", Febs Letters, 286(1–2): 58–60 (Jul. 1991).

(List continued on next page.)

Primary Examiner—Gary L. Kunz
Assistant Examiner—Robert S. Landsman
(74) Attorney, Agent, or Firm—John W. Mahoney; Melissa A. Shaw

(57) ABSTRACT

This invention realizes a less toxic IL-4 mutant that allows greater therapeutic use of interleukin 4. Further, the invention is directed to IL-4 muteins having single and double mutations represented by the designators R121E and T13D/R121E, numbered in accordance with wild type IL-4 (His= 1). The invention also includes polynucleotides coding for the muteins of the invention, vectors containing the polynucleotides, transformed host cells, pharmaceutical compositions comprising the muteins, and therapeutic methods of treatment.

4 Claims, 20 Drawing Sheets

OTHER PUBLICATIONS

Figure 2:
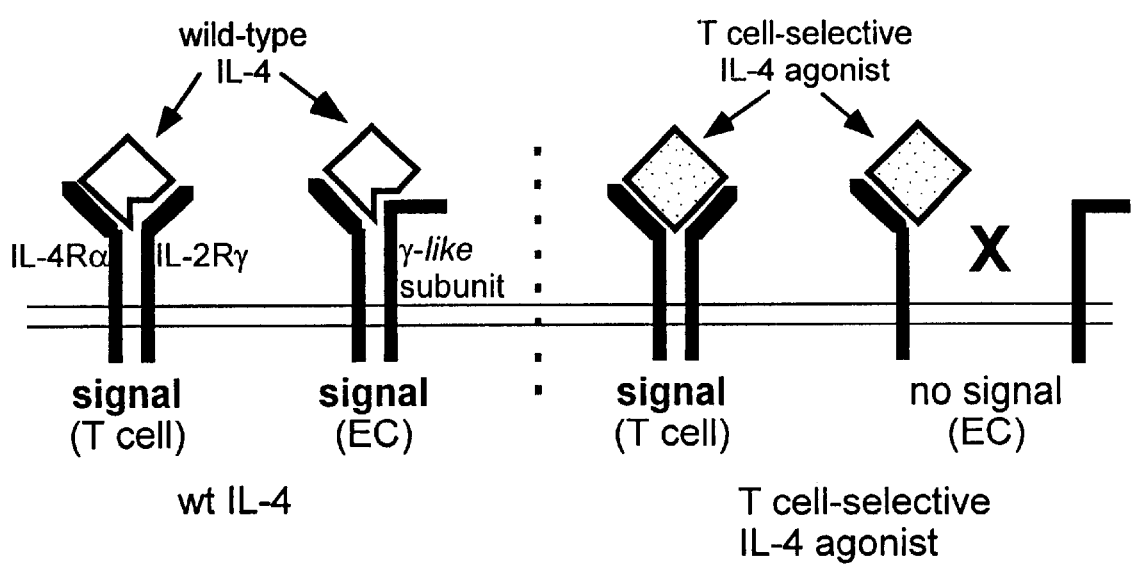
Figure 3A:
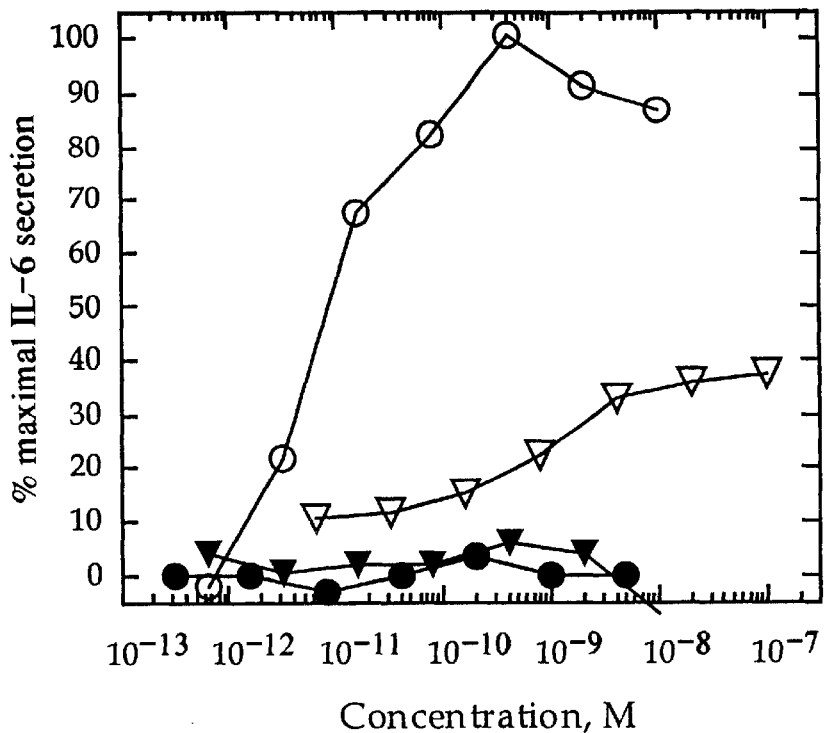
Figure 3B:
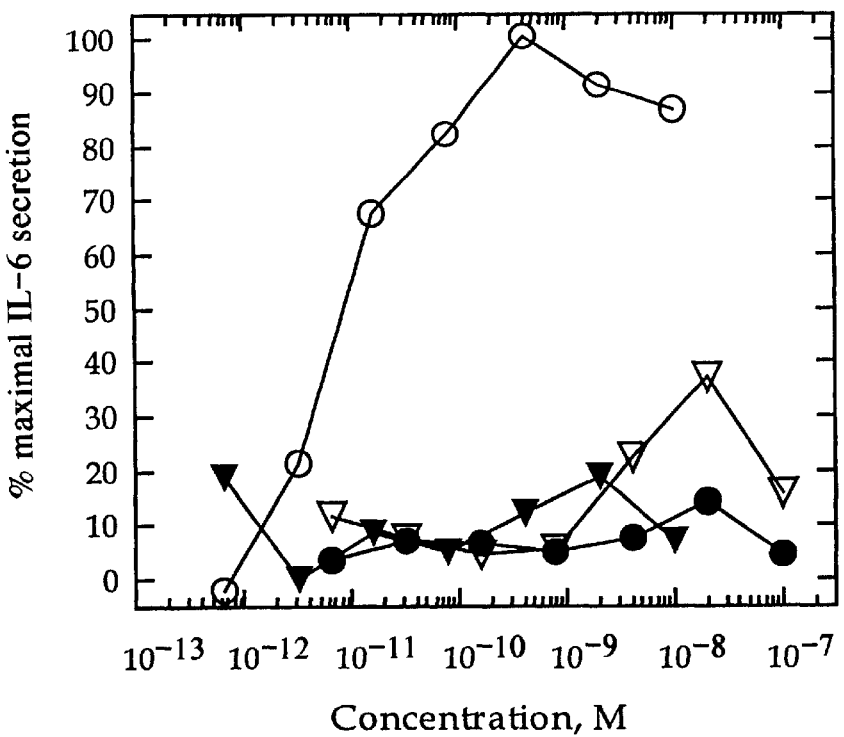
Figure 4A:
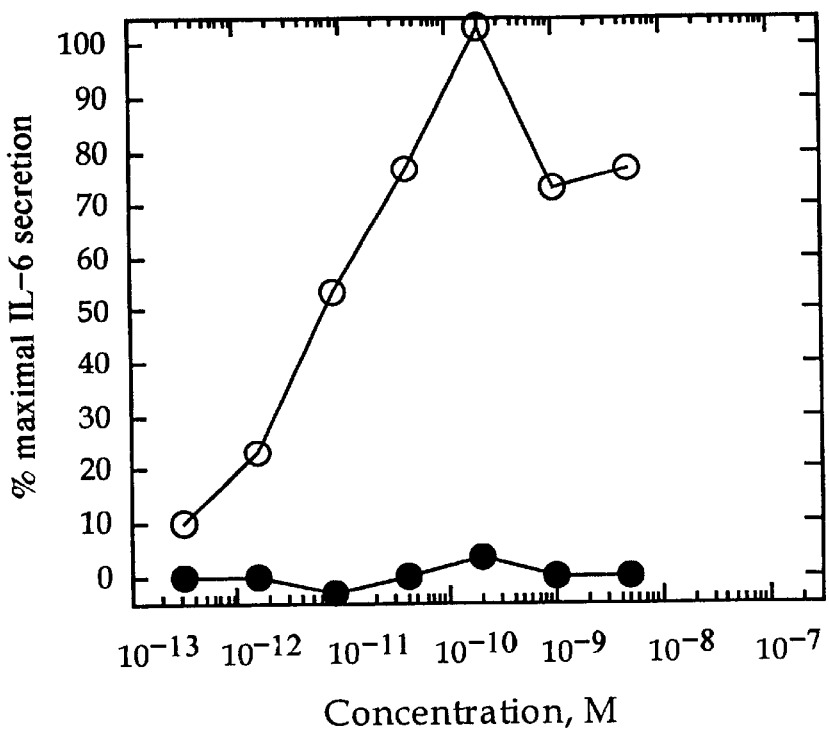
Figure 4B:
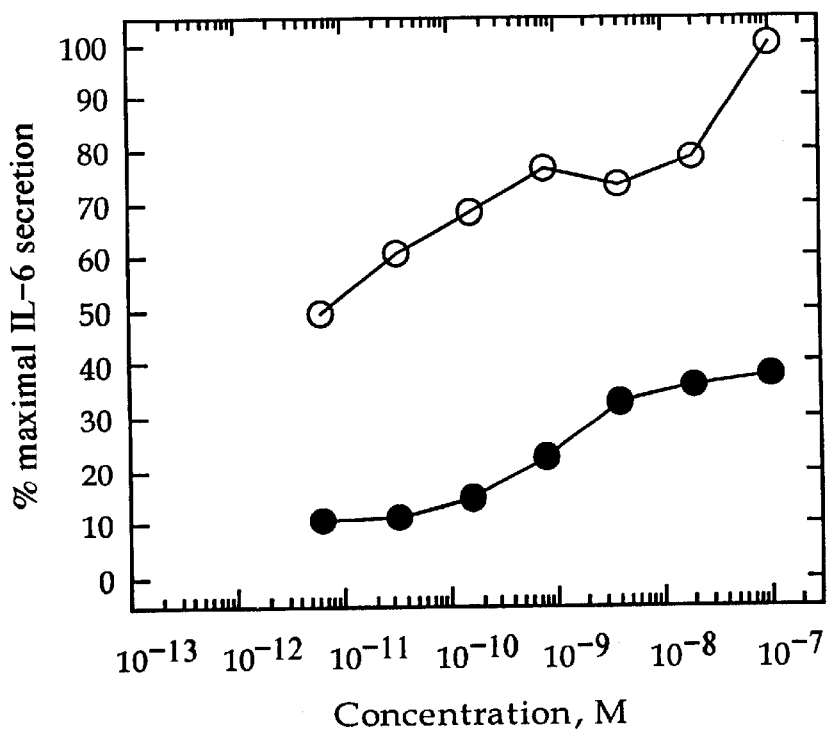
Figure 4C:
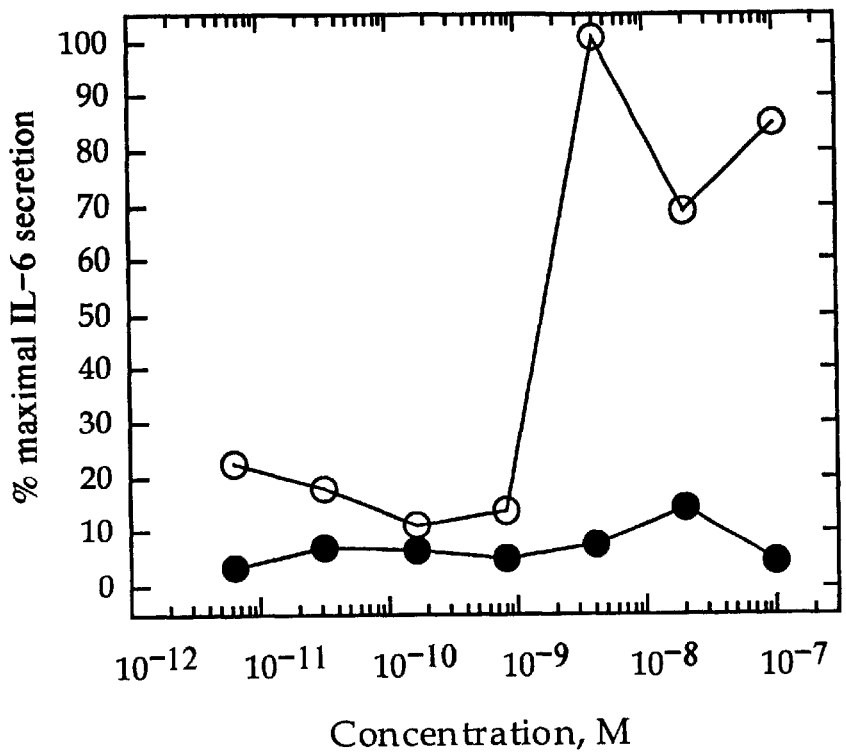
Figure 4D:
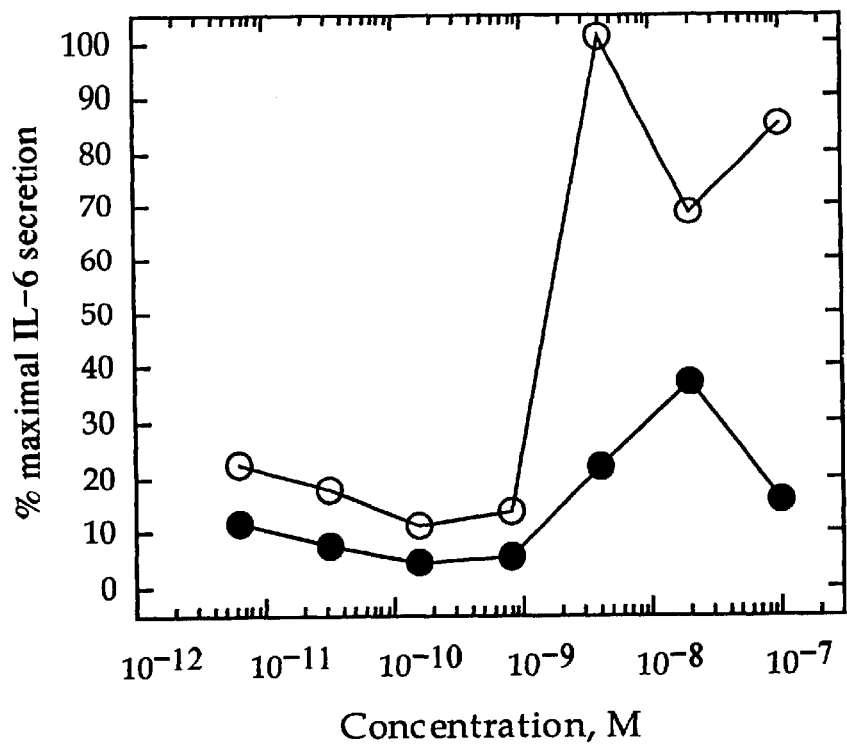
Figure 4E:
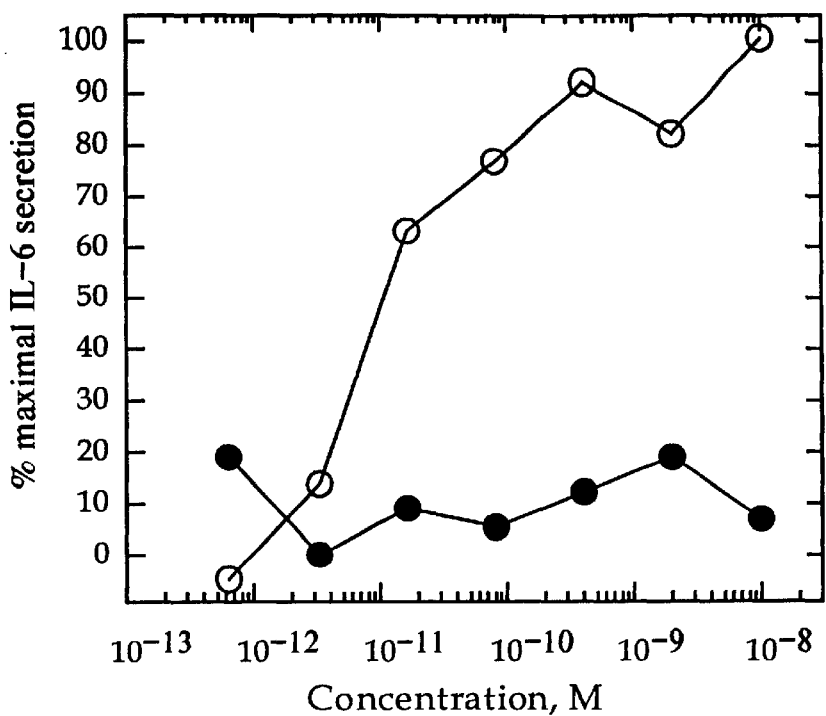
Figure 4F:
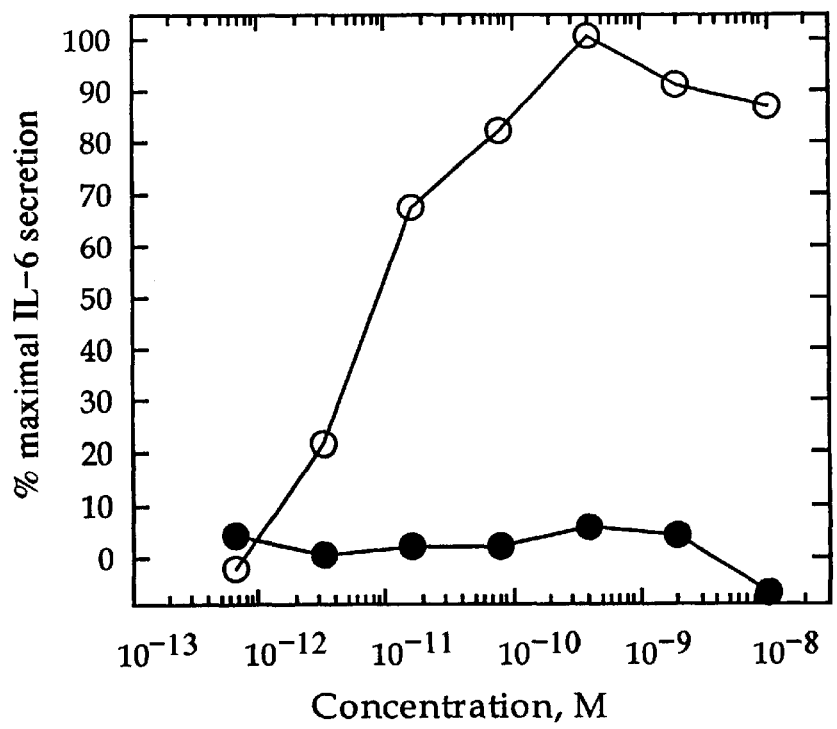
Figure 5A:
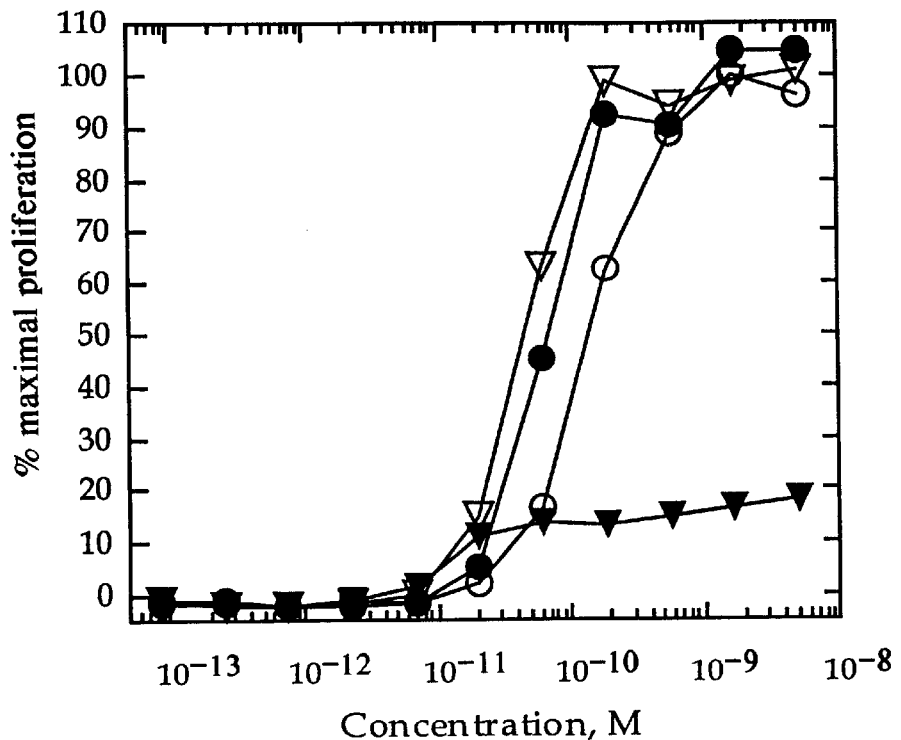
Figure 5B:
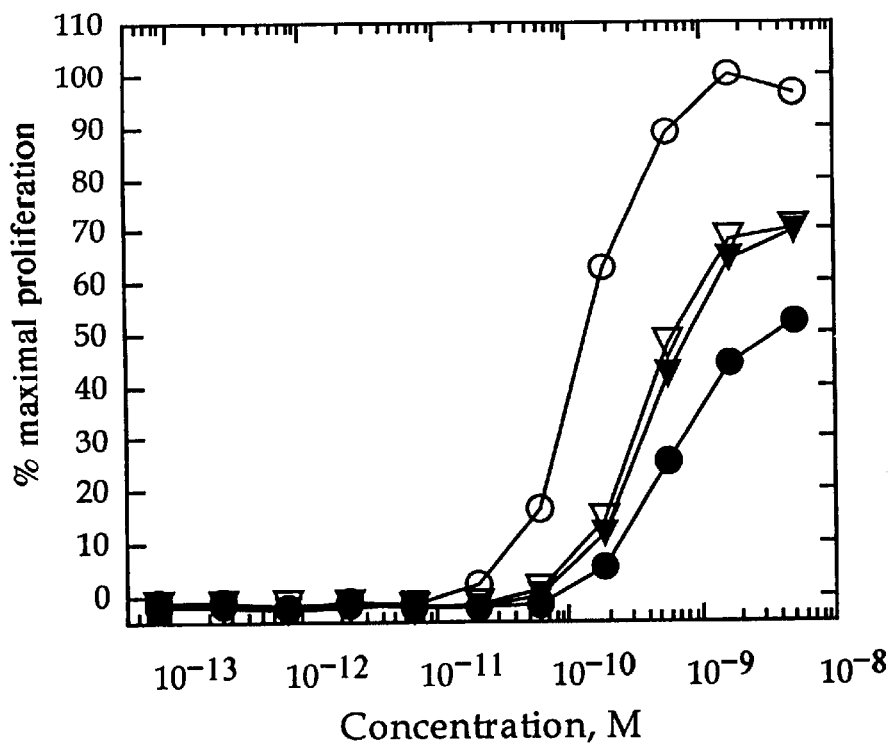
Figure 6A:
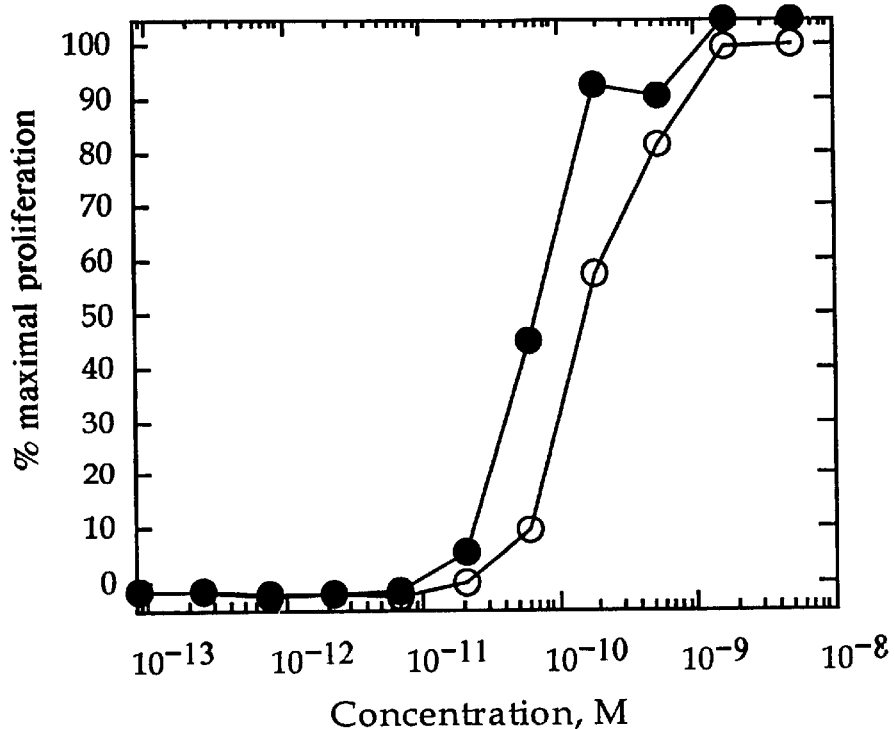
Figure 6B:
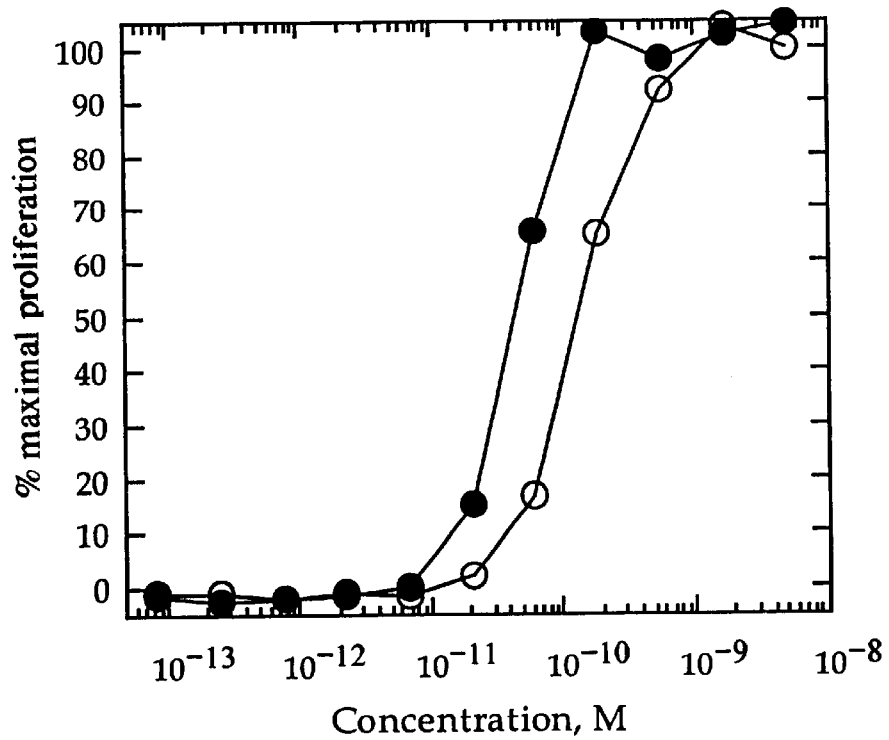
Figure 6C:
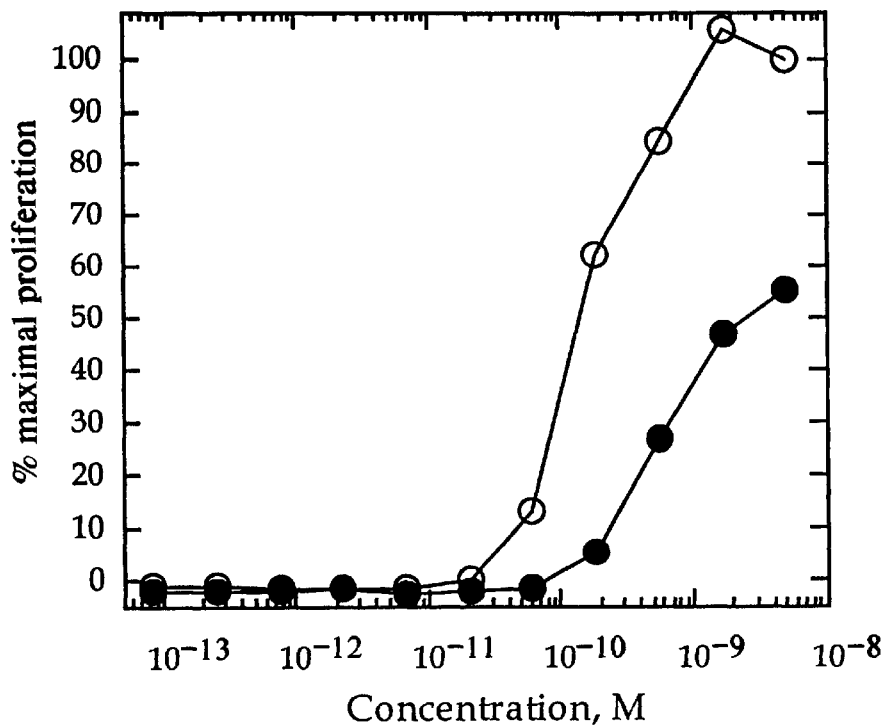
Figure 6D:
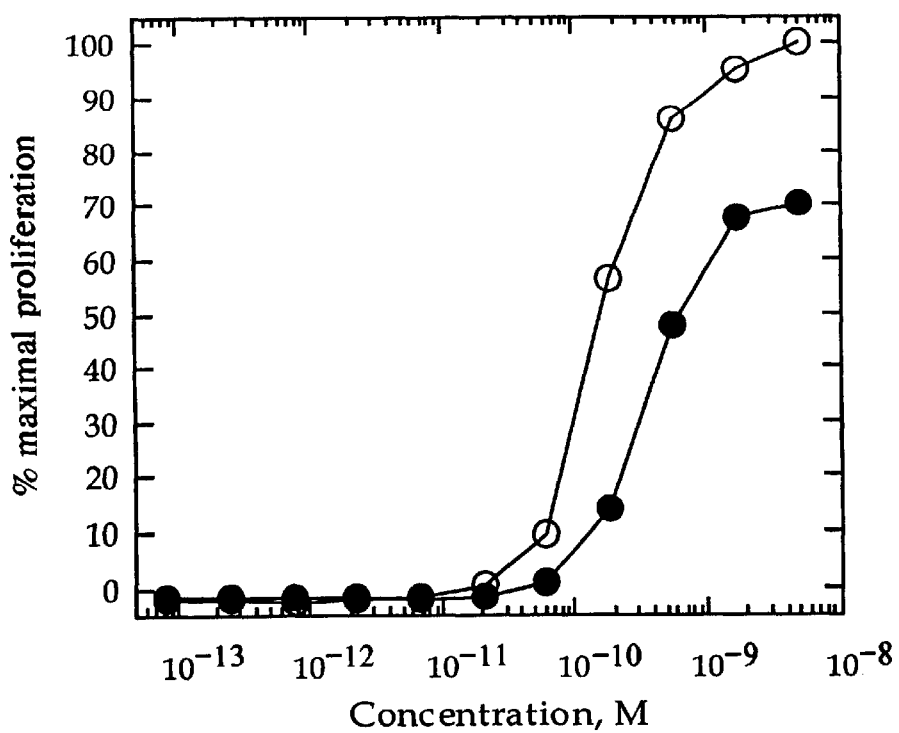
Figure 6E:
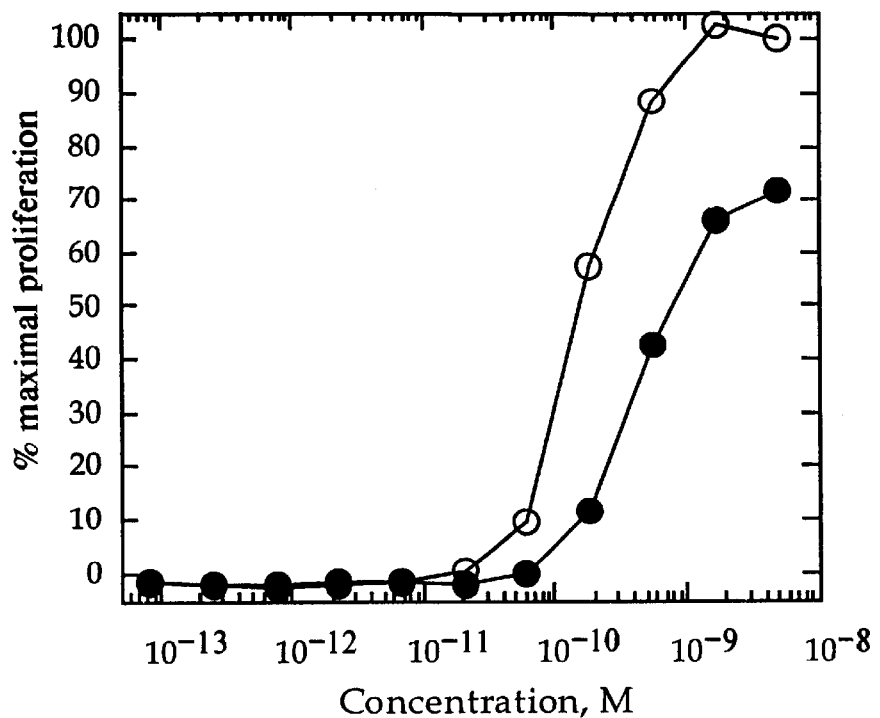
Figure 6F:
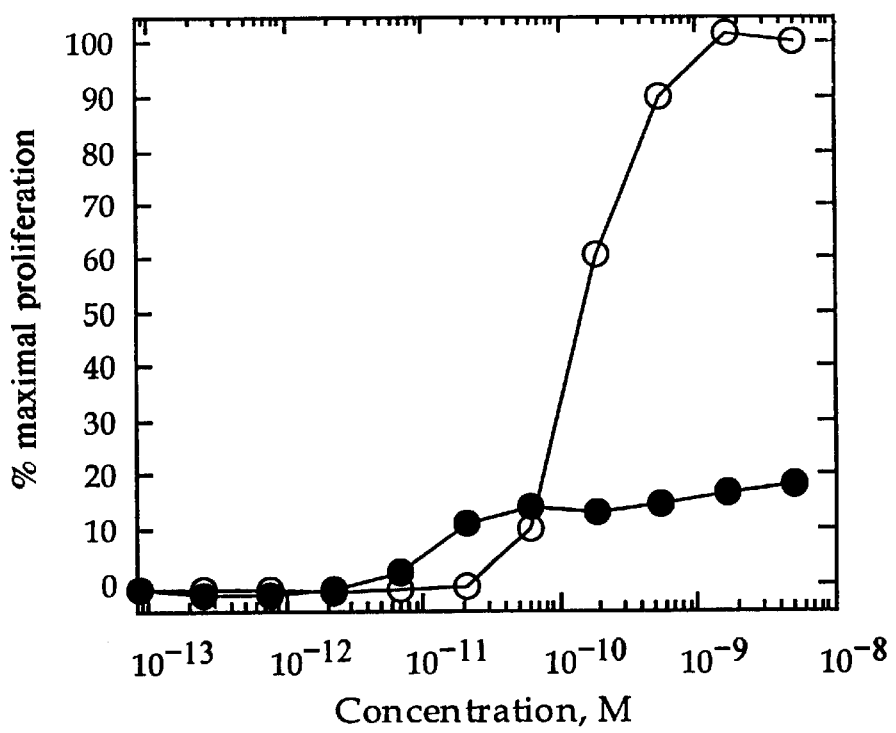
Figure 7:
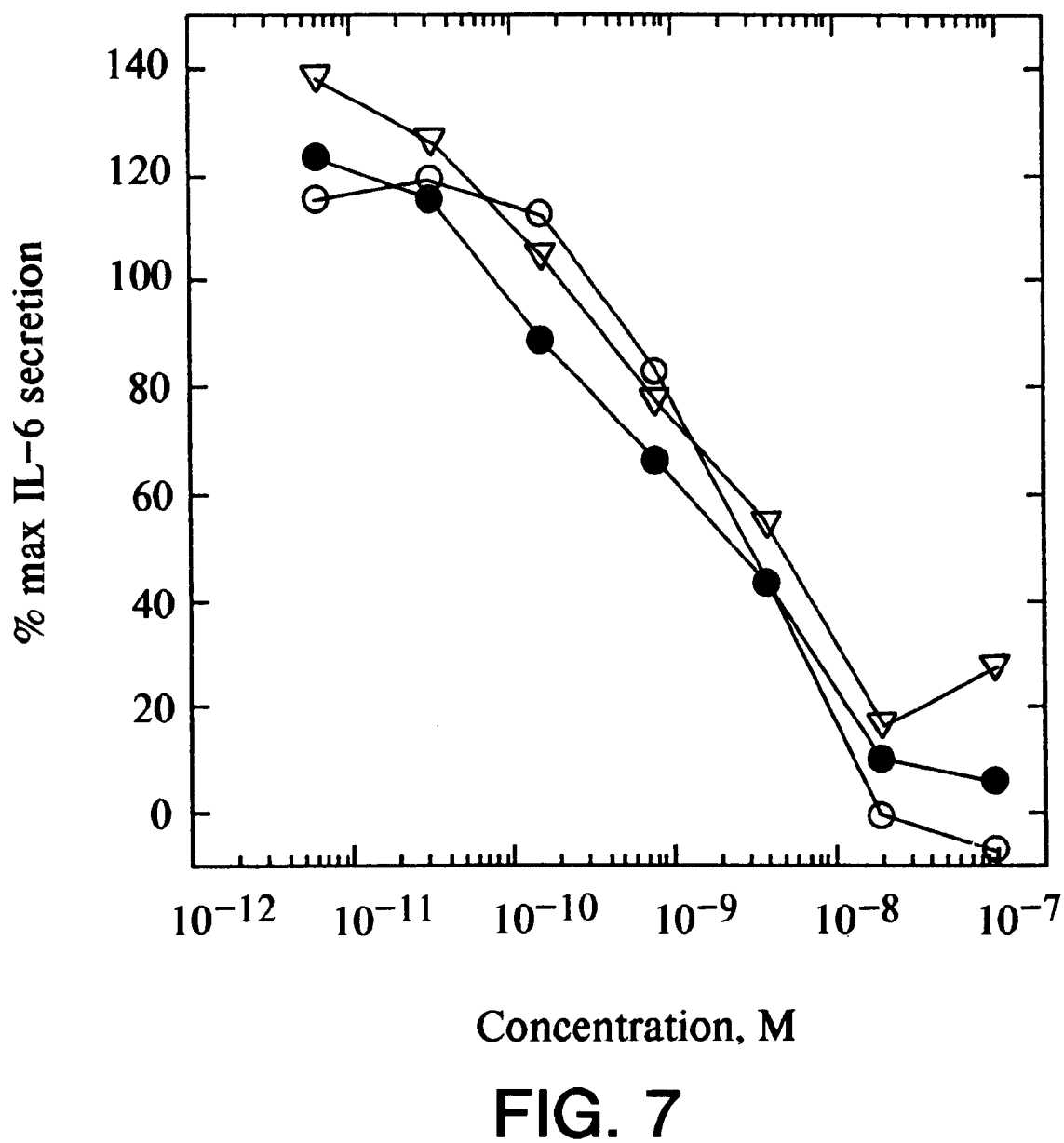
Figure 8A:
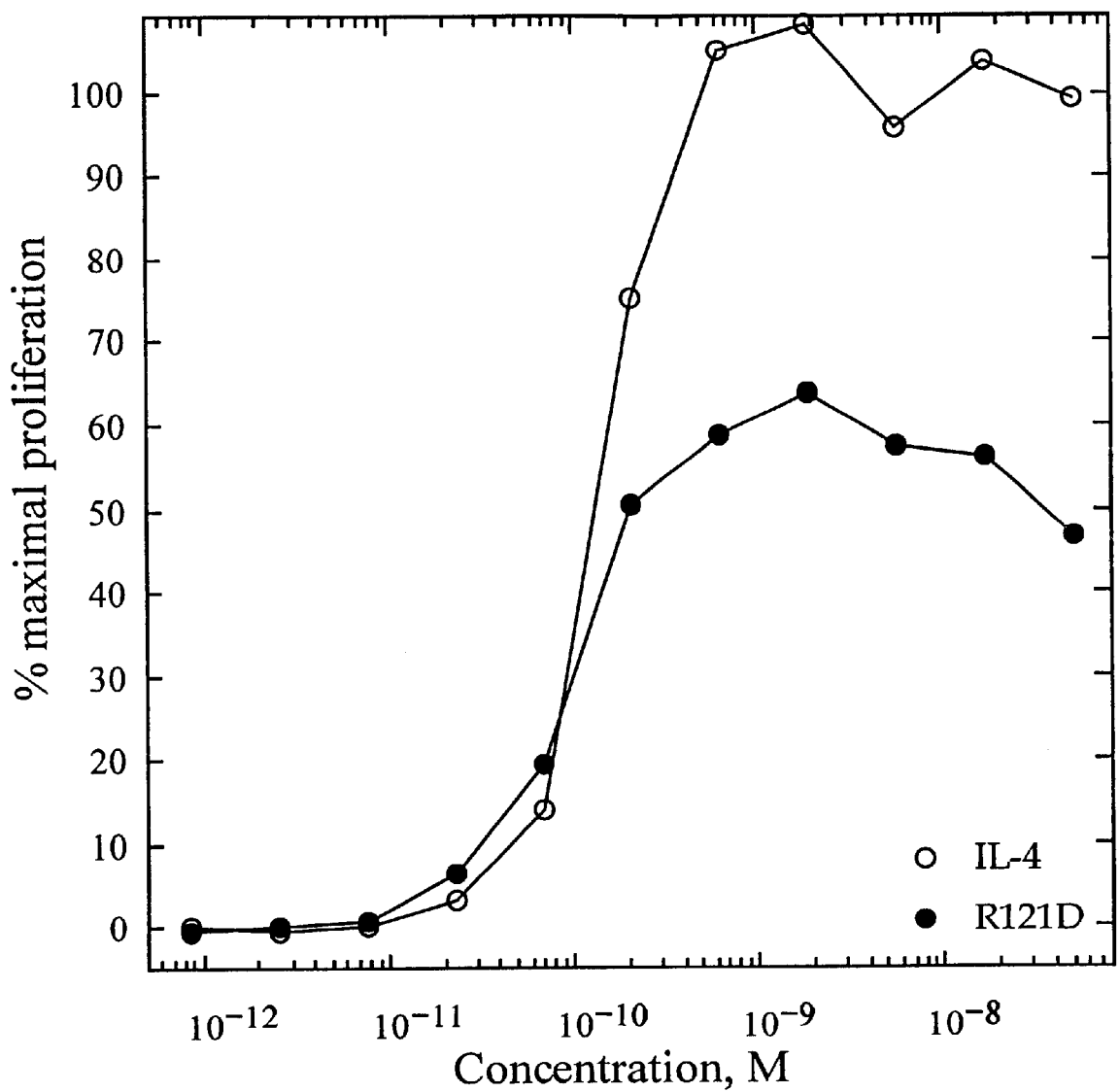
Figure 8B:
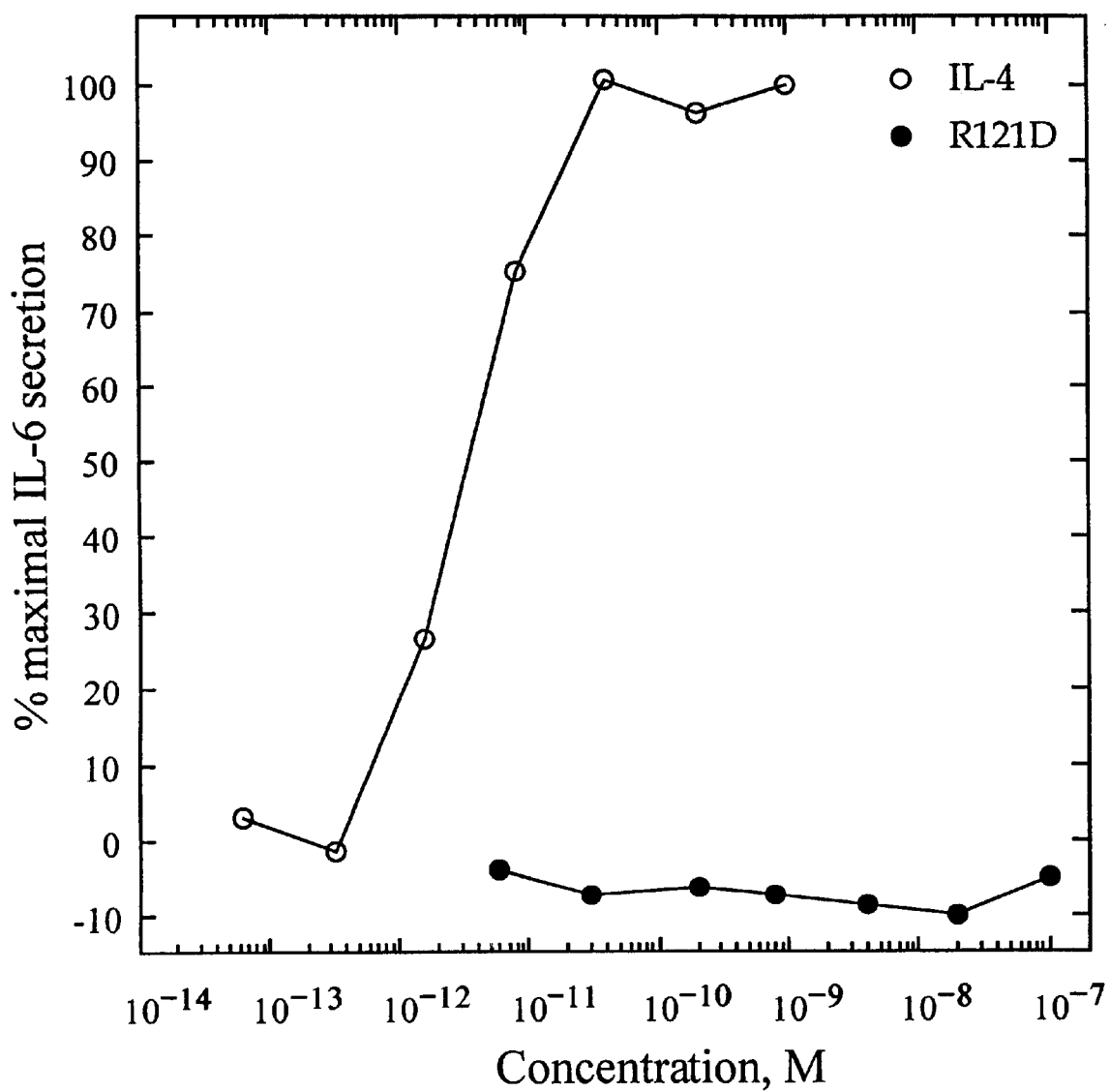
Figure 9A:
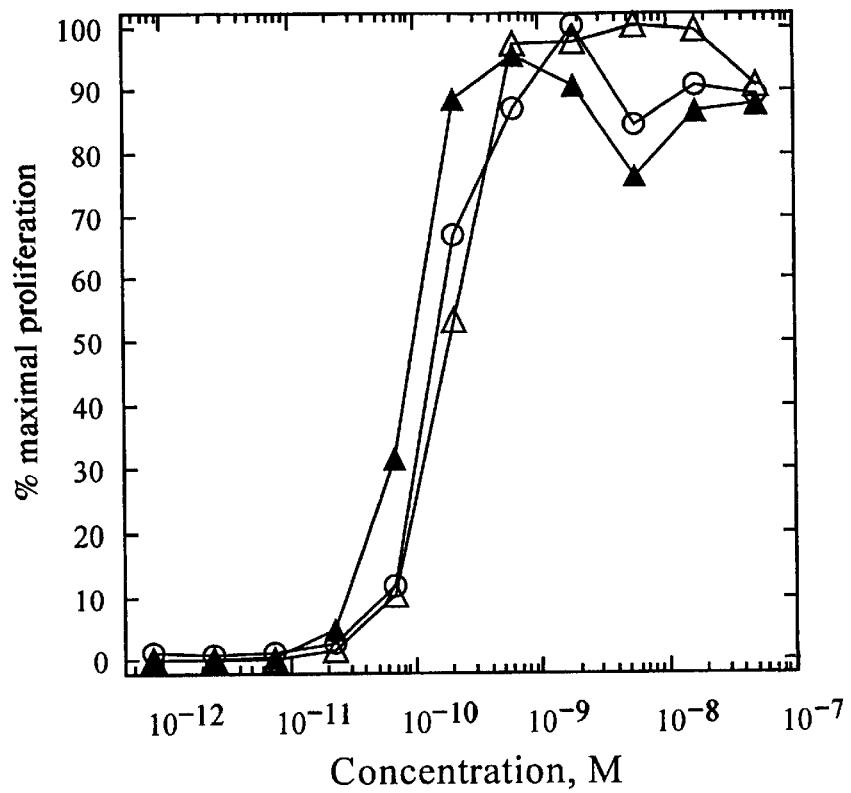
Figure 9B:
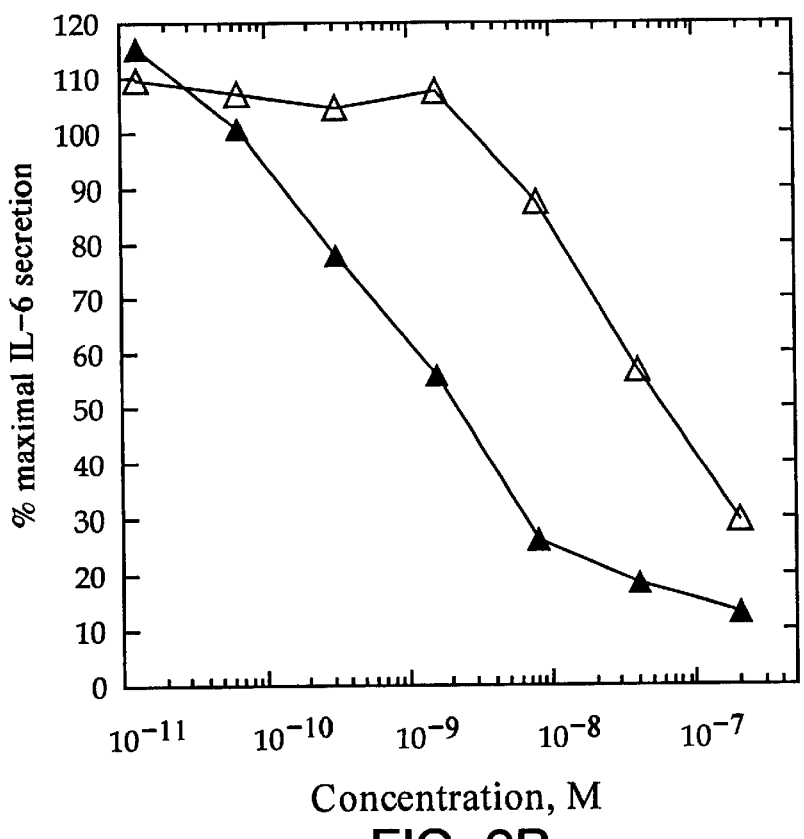
Figure 9C:
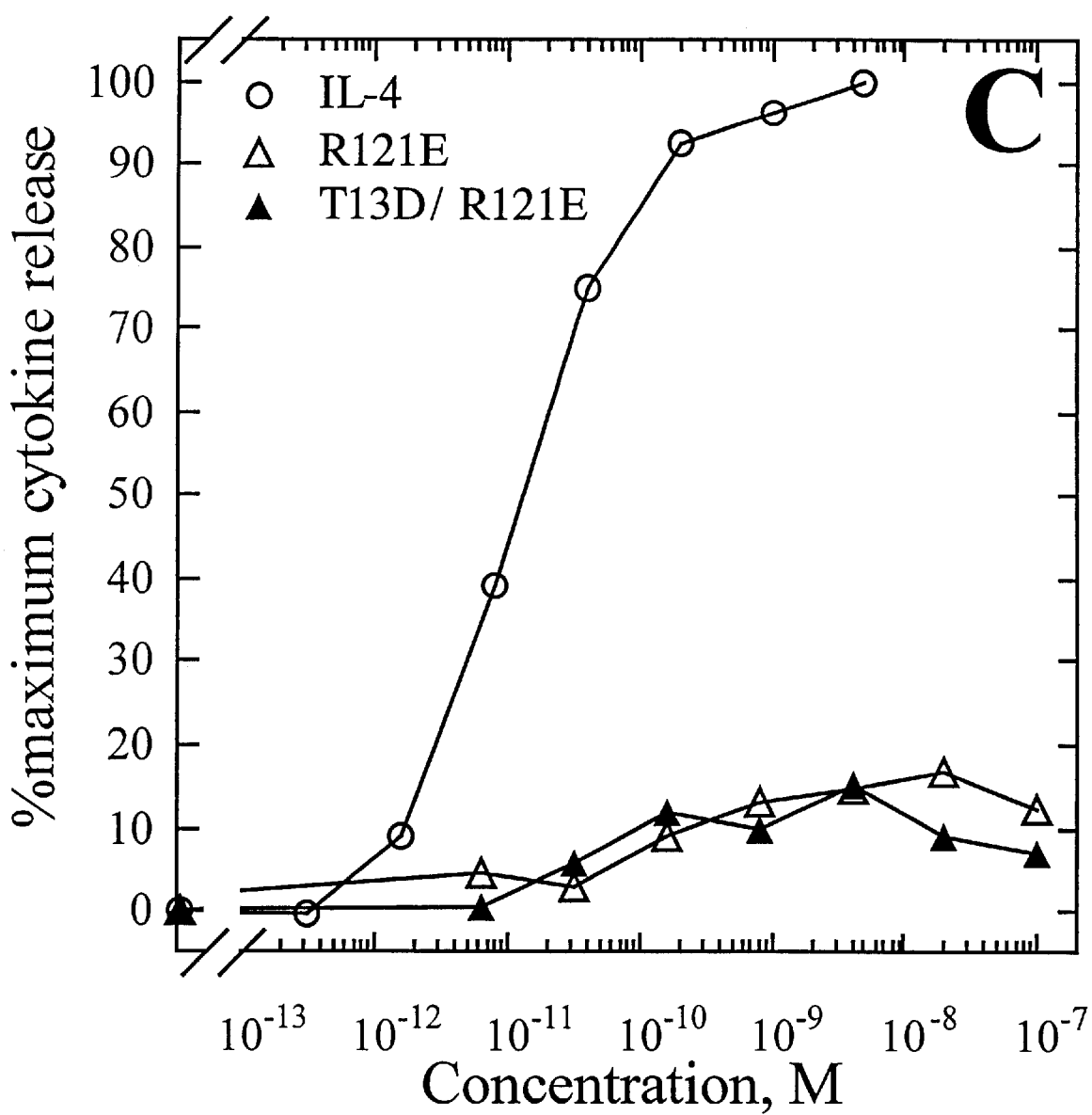

Lakkis, F., et al., "Phe496 and Leu497 are essential for receptor binding and cytotoxic action of the murine interleukin–4 receptor targeted fusion toxin $DAB_{389}$–mIL–4", Prot. Eng., 5(3): 241–248 (1992).

Lewis, C., et al., "Use of a novel mutagenesis strategy, optimized residue substitution, to decrease the off–rate of an anti–gp120 antibody", Mol. Immunol., 32(14): 1065–1072 (1995).

Liblau, R., et al., "Th1 and Th2 CD4+ T cells in the pathogenesis of organ–specific autoimmune diseases", Immunology Today, 16(1): 34–38 (1995).

Lopez, A., et al., "A human interleukin–3 analog with increased biological and binding activities", PNAS (USA), 89: 11842–11846 (1992).

Maher, D.W., et al., "Human interleukin–4: an immunomodulator with potential therapeutic applications", Progress in Growth Factor Research, 3: 43–56 (1991).

Margolin, K., et al., "Phase II studies of recombinant human interleukin–4 in advanced renal cancer and malignant melanoma", J. Immunotherapy, 15: 147–153 (1994).

Matthews, D., et al., "Function of the interleukin–2(IL–2) receptor g–chain in biologic responses of X–linked severe combined immunodeficient B cells to IL–2, IL–4, IL–13, and IL–15", Blood 85(1): 38–42 (1995).

Morrison, B., et al., "A receptor binding domain of mouse interleukin–4 defined by a solid–Phase binding assay and in vitro mutagenesis", J. Biol. Chem., 267(17): 11957–11963 (1992).

Müller, T., et al., "Human Interleukin–4 and Variant R88Q: Phasing X–ray Diffraction Data by Molecular Replacement Using X–ray and Nuclear Magnetic Resonance Models", J. Mol. Biol., 247: 360–372 (1995).

Ngo, J. T., et al., "Computational Complexity Protein Structure Prediction, and the Levinthal Paradox", in *The Protein Folding Problem and Tertiary Structure Prediction*, K. Mertz Jr. and S. Le Grand, eds. (Birkhäuser, Boston, 1994) pp. 433 and 492–495.

Obiri, N., et al., "Receptor for Interleukin 13", J. Biol. Chem., 270(15); 8797–8804 (1995).

Olins, P., et al., "Saturation mutagenesis of human interleukin–3", Biol. Chem., 270(40): 23754–23760 (1995).

Powers, R., et al., "Three–Dimensional Solution Structure of Human Interleukin–4 by Multidimensional Heteronuclear Magnetic Resonance Spectroscopy", Science, 256:1673–1677 (Jn. 1992)(.

Powrie, F., et al., "Cytokine regulation of T–cell function: potential for therapeutic intervention", Immunology Today, 14(6): 270–274 (1993).

Racke, M.K., et al., "Cytokine–induced immune deviation as a therapy for inflammatory autoimmune disease", J Exp. Med. (USA), 180(5): 1961–1966—Abstract (1994).

Russell, S., et al., "Interleukin–2 receptor g chain: a functional component of the interleukin–4 receptor", Science, 262: 1880–1883 (1993).

Savion, R., et al., "Rational design of a receptor super–antagonist of human interleukin–6", The EMBO Journal 13(24): 5863–5870 (1994).

Savion, R., et al., "Saturation mutagenesis of the human interleukin–6 receptor–binding site: implications for its three–dimensional structure", PNAS (USA), 90: 4067–4071 (1993).

Schnyder, B., et al., "Interleukin–4 (IL–4) and IL–13 bind to a shared heterodimeric complex on endothelial cells mediating vascular cell adhesion molecule–1 induction in the absence of the common g chain", Blood, 87(10): 4286–4295 (1996).

Tony, H–P., et al., "Design of human interleukin–4 antagonists inhibiting interleukin–4–dependent and interleukin–13–dependent responses in T–cells and B–cells with high efficiency", E. J. Biochem., pp. 659–665 (1994).

Walter, et al., "Crystal structure of a complex between interferon–g and its soluble high–affinity receptor", Nature, 376: 230–235 (1995).

Wlodawer, A., et al., "Hematopoietic cytokines: similarities and differences in the structures, with implications for receptor binding", Protein Science, 2: 1373–1382 (1993).

Zurawski, S., et al., "Receptors for interleukin–13 and interleukin–4 are complex and share a novel component that functions in signal transduction", The EMBO Journal, 12(7): 2663–2670 (1993).

SEQ ID NO:1:

```
                    Helix A →
His Lys Cys Asp Ile Thr Leu Gln Glu Ile Ile Lys Thr Leu Asn
1               5                   10                  15

Ser Leu Thr Glu Gln Lys Thr Leu Cys Thr Glu Leu Thr Val Thr
                20                  25                  30

Helix B →
Asp Ile Phe Ala Ala Ser Lys Asn Thr Thr Glu Lys Glu Thr Phe
                35                  40                  45

Cys Arg Ala Ala Thr Val Leu Arg Gln Phe Tyr Ser His His Glu
                50                  55                  60

Helix C →
Lys Asp Thr Arg Cys Leu Gly Ala Thr Ala Gln Gln Phe His Arg
                65                  70                  75

His Lys Gln Leu Ile Arg Phe Leu Lys Arg Leu Asp Arg Asn Leu
                80                  85                  90

Trp Gly Leu Ala Gly Leu Asn Ser Cys Pro Val Lys Glu Ala Asn
                95                  100                 105

Helix D →
Gln Ser Thr Leu Glu Asn Phe Leu Glu Arg Leu Lys Thr Ile Met
                110                 115                 120

Arg Glu Lys Tyr Ser Lys Cys Ser Ser
                125
```

FIG. 1

SEQUENCE LISTING

<160> NUMBER OF SEQ ID NOS: 42

<210> SEQ ID NO 1
<211> LENGTH: 129
<212> TYPE: PRT
<213> ORGANISM: Homo sapiens
<220> FEATURE:

<400> SEQUENCE: 1

His Lys Cys Asp Ile Thr Leu Gln Glu Ile Ile Lys Thr Leu Asn Ser
 1               5                   10                  15

Leu Thr Glu Gln Lys Thr Leu Cys Thr Glu Leu Thr Val Thr Asp Ile
            20                  25                  30

Phe Ala Ala Ser Lys Asn Thr Thr Glu Lys Glu Thr Phe Cys Arg Ala
        35                  40                  45

Ala Thr Val Leu Arg Gln Phe Tyr Ser His His Glu Lys Asp Thr Arg
    50                  55                  60

Cys Leu Gly Ala Thr Ala Gln Gln Phe His Arg His Lys Gln Leu Ile
65                  70                  75                  80

Arg Phe Leu Lys Arg Leu Asp Arg Asn Leu Trp Gly Leu Ala Gly Leu
                85                  90                  95

Asn Ser Cys Pro Val Lys Glu Ala Asn Gln Ser Thr Leu Glu Asn Phe
            100                 105                 110

Leu Glu Arg Leu Lys Thr Ile Met Arg Glu Lys Tyr Ser Lys Cys Ser
        115                 120                 125

Ser

<210> SEQ ID NO 2
<211> LENGTH: 462
<212> TYPE: DNA
<213> ORGANISM: Homo sapiens
<220> FEATURE:
<221> NAME/KEY: CDS
<222> LOCATION: (1)..(459)
<223> OTHER INFORMATION: Description: human IL-4 protein

<400> SEQUENCE: 2 atg ggt ctc acc tcc gaa ctg ctt ccc cct ctg ttc ttc ctg cta gca      48
Met Gly Leu Thr Ser Glu Leu Leu Pro Pro Leu Phe Phe Leu Leu Ala
 1               5                   10                  15 tgt gcc ggc aac ttt gtc cac gga cac aag tgc gat atc acc tta cag      96
Cys Ala Gly Asn Phe Val His Gly His Lys Cys Asp Ile Thr Leu Gln

```
                    20                      25                      30
gag atc atc aaa act ttg aac agc ctc aca gag cag aag act ctg tgc        144
Glu Ile Ile Lys Thr Leu Asn Ser Leu Thr Glu Gln Lys Thr Leu Cys
             35                      40                      45 acc gag ttg acc gta aca gac atc ttt gct gcc tcc aag aac aca act        192
Thr Glu Leu Thr Val Thr Asp Ile Phe Ala Ala Ser Lys Asn Thr Thr
     50                      55                      60 gag aag gaa acc ttc tgc agg gct gcg act gtg ctc cgg cag ttc tac        240
Glu Lys Glu Thr Phe Cys Arg Ala Ala Thr Val Leu Arg Gln Phe Tyr
 65                      70                      75                  80 agc cac cat gag aag gac act cgc tgc ctg ggt gcg act gca cag cag        288
Ser His His Glu Lys Asp Thr Arg Cys Leu Gly Ala Thr Ala Gln Gln
                     85                      90                      95 ttc cac agg cac aag cag ctg atc cga ttc ctg aaa cgg ctc gac agg        336
Phe His Arg His Lys Gln Leu Ile Arg Phe Leu Lys Arg Leu Asp Arg
                 100                     105                     110 aac ctc tgg ggc ctg gcg ggc ttg aat tcc tgt cct gtg aag gaa gcc        384
Asn Leu Trp Gly Leu Ala Gly Leu Asn Ser Cys Pro Val Lys Glu Ala
             115                     120                     125 aac cag agt acg ttg gaa aac ttc ttg gaa agg cta aag acg atc atg        432
Asn Gln Ser Thr Leu Glu Asn Phe Leu Glu Arg Leu Lys Thr Ile Met
 130                     135                     140 aga gag aaa tat tca aag tgt tcg agc tag                                462
Arg Glu Lys Tyr Ser Lys Cys Ser Ser
145                     150

<210> SEQ ID NO 3
<211> LENGTH: 462
<212> TYPE: DNA
<213> ORGANISM: Homo sapiens
<220> FEATURE:
<221> NAME/KEY: CDS
<222> LOCATION: (1)..(459)
<223> OTHER INFORMATION: Description: hIL-4/R121A

<400> SEQUENCE: 3 atg ggt ctc acc tcc gaa ctg ctt ccc cct ctg ttc ttc ctg cta gca         48
Met Gly Leu Thr Ser Glu Leu Leu Pro Pro Leu Phe Phe Leu Leu Ala
 1               5                      10                      15 tgt gcc ggc aac ttt gtc cac gga cac aag tgc gat atc acc tta cag         96
Cys Ala Gly Asn Phe Val His Gly His Lys Cys Asp Ile Thr Leu Gln
             20                      25                      30 gag atc atc aaa act ttg aac agc ctc aca gag cag aag act ctg tgc        144
Glu Ile Ile Lys Thr Leu Asn Ser Leu Thr Glu Gln Lys Thr Leu Cys
             35                      40                      45 acc gag ttg acc gta aca gac atc ttt gct gcc tcc aag aac aca act        192
Thr Glu Leu Thr Val Thr Asp Ile Phe Ala Ala Ser Lys Asn Thr Thr
     50                      55                      60 gag aag gaa acc ttc tgc agg gct gcg act gtg ctc cgg cag ttc tac        240
Glu Lys Glu Thr Phe Cys Arg Ala Ala Thr Val Leu Arg Gln Phe Tyr
 65                      70                      75                  80 agc cac cat gag aag gac act cgc tgc ctg ggt gcg act gca cag cag        288
Ser His His Glu Lys Asp Thr Arg Cys Leu Gly Ala Thr Ala Gln Gln
                     85                      90                      95 ttc cac agg cac aag cag ctg atc cga ttc ctg aaa cgg ctc gac agg        336
Phe His Arg His Lys Gln Leu Ile Arg Phe Leu Lys Arg Leu Asp Arg
                 100                     105                     110 aac ctc tgg ggc ctg gcg ggc ttg aat tcc tgt cct gtg aag gaa gcc        384
Asn Leu Trp Gly Leu Ala Gly Leu Asn Ser Cys Pro Val Lys Glu Ala
             115                     120                     125 aac cag agt acg ttg gaa aac ttc ttg gaa agg cta aag acg atc atg        432
```

```
Asn Gln Ser Thr Leu Glu Asn Phe Leu Glu Arg Leu Lys Thr Ile Met
        130                 135                 140 gct gag aaa tat tca aag tgt tcg agc tag                              462
Ala Glu Lys Tyr Ser Lys Cys Ser Ser
145                 150

<210> SEQ ID NO 4
<211> LENGTH: 462
<212> TYPE: DNA
<213> ORGANISM: Homo sapiens
<220> FEATURE:
<221> NAME/KEY: CDS
<222> LOCATION: (1)..(459)
<223> OTHER INFORMATION: Description: hIL-4/R121D

<400> SEQUENCE: 4 atg ggt ctc acc tcc gaa ctg ctt ccc cct ctg ttc ttc ctg cta gca     48
Met Gly Leu Thr Ser Glu Leu Leu Pro Pro Leu Phe Phe Leu Leu Ala
1               5                   10                  15 tgt gcc ggc aac ttt gtc cac gga cac aag tgc gat atc acc tta cag     96
Cys Ala Gly Asn Phe Val His Gly His Lys Cys Asp Ile Thr Leu Gln
            20                  25                  30 gag atc atc aaa act ttg aac agc ctc aca gag cag aag act ctg tgc    144
Glu Ile Ile Lys Thr Leu Asn Ser Leu Thr Glu Gln Lys Thr Leu Cys
        35                  40                  45 acc gag ttg acc gta aca gac atc ttt gct gcc tcc aag aac aca act    192
Thr Glu Leu Thr Val Thr Asp Ile Phe Ala Ala Ser Lys Asn Thr Thr
    50                  55                  60 gag aag gaa acc ttc tgc agg gct gcg act gtg ctc cgg cag ttc tac    240
Glu Lys Glu Thr Phe Cys Arg Ala Ala Thr Val Leu Arg Gln Phe Tyr
65                  70                  75                  80 agc cac cat gag aag gac act cgc tgc ctg ggt gcg act gca cag cag    288
Ser His His Glu Lys Asp Thr Arg Cys Leu Gly Ala Thr Ala Gln Gln
                85                  90                  95 ttc cac agg cac aag cag ctg atc cga ttc ctg aaa cgg ctc gac agg    336
Phe His Arg His Lys Gln Leu Ile Arg Phe Leu Lys Arg Leu Asp Arg
            100                 105                 110 aac ctc tgg ggc ctg gcg ggc ttg aat tcc tgt cct gtg aag gaa gcc    384
Asn Leu Trp Gly Leu Ala Gly Leu Asn Ser Cys Pro Val Lys Glu Ala
        115                 120                 125 aac cag agt acg ttg gaa aac ttc ttg gaa agg cta aag acg atc atg    432
Asn Gln Ser Thr Leu Glu Asn Phe Leu Glu Arg Leu Lys Thr Ile Met
    130                 135                 140 gac gag aaa tat tca aag tgt tcg agc tag                              462
Asp Glu Lys Tyr Ser Lys Cys Ser Ser
145                 150

<210> SEQ ID NO 5
<211> LENGTH: 462
<212> TYPE: DNA
<213> ORGANISM: Homo sapiens
<220> FEATURE:
<221> NAME/KEY: CDS
<222> LOCATION: (1)..(459)
<223> OTHER INFORMATION: Description: hIL-4/R121E

<400> SEQUENCE: 5 atg ggt ctc acc tcc caa ctg ctt ccc cct ctg ttc ttc ctg cta gca     48
Met Gly Leu Thr Ser Gln Leu Leu Pro Pro Leu Phe Phe Leu Leu Ala
1               5                   10                  15 tgt gcc ggc aac ttt gtc cac gga cac aag tgc gat atc acc tta cag     96
Cys Ala Gly Asn Phe Val His Gly His Lys Cys Asp Ile Thr Leu Gln
            20                  25                  30
```

```
gag atc atc aaa act ttg aac agc ctc aca gag cag aag act ctg tgc      144
Glu Ile Ile Lys Thr Leu Asn Ser Leu Thr Glu Gln Lys Thr Leu Cys
        35                  40                  45 acc gag ttg acc gta aca gac atc ttt gct gcc tcc aag aac aca act      192
Thr Glu Leu Thr Val Thr Asp Ile Phe Ala Ala Ser Lys Asn Thr Thr
 50                  55                  60 gag aag gaa acc ttc tgc agg gct gcg act gtg ctc cgg cag ttc tac      240
Glu Lys Glu Thr Phe Cys Arg Ala Ala Thr Val Leu Arg Gln Phe Tyr
 65                  70                  75                  80 agc cac cat gag aag gac act cgc tgc ctg ggt gcg act gca cag cag      288
Ser His His Glu Lys Asp Thr Arg Cys Leu Gly Ala Thr Ala Gln Gln
             85                  90                  95 ttc cac agg cac aag cag ctg atc cga ttc ctg aaa cgg ctc gac agg      336
Phe His Arg His Lys Gln Leu Ile Arg Phe Leu Lys Arg Leu Asp Arg
            100                 105                 110 aac ctc tgg ggc ctg gcg ggc ttg aat tcc tgt cct gtg aag gaa gcc      384
Asn Leu Trp Gly Leu Ala Gly Leu Asn Ser Cys Pro Val Lys Glu Ala
        115                 120                 125 aac cag agt acg ttg gaa aac ttc ttg gaa agg cta aag acg atc atg      432
Asn Gln Ser Thr Leu Glu Asn Phe Leu Glu Arg Leu Lys Thr Ile Met
    130                 135                 140 gaa gag aaa tat tca aag tgt tcg agc tag                              462
Glu Glu Lys Tyr Ser Lys Cys Ser Ser
145                 150
```

<210> SEQ ID NO 6
<211> LENGTH: 462
<212> TYPE: DNA
<213> ORGANISM: Homo sapiens
<220> FEATURE:
<221> NAME/KEY: CDS
<222> LOCATION: (1)..(459)
<223> OTHER INFORMATION: Description: hIL-4/R121F

<400> SEQUENCE: 6

```
atg ggt ctc acc tcc gaa ctg ctt ccc cct ctg ttc ttc ctg cta gca       48
Met Gly Leu Thr Ser Glu Leu Leu Pro Pro Leu Phe Phe Leu Leu Ala
 1               5                  10                  15 tgt gcc ggc aac ttt gtc cac gga cac aag tgc gat atc acc tta cag       96
Cys Ala Gly Asn Phe Val His Gly His Lys Cys Asp Ile Thr Leu Gln
             20                  25                  30 gag atc atc aaa act ttg aac agc ctc aca gag cag aag act ctg tgc      144
Glu Ile Ile Lys Thr Leu Asn Ser Leu Thr Glu Gln Lys Thr Leu Cys
        35                  40                  45 acc gag ttg acc gta aca gac atc ttt gct gcc tcc aag aac aca act      192
Thr Glu Leu Thr Val Thr Asp Ile Phe Ala Ala Ser Lys Asn Thr Thr
 50                  55                  60 gag aag gaa acc ttc tgc agg gct gcg act gtg ctc cgg cag ttc tac      240
Glu Lys Glu Thr Phe Cys Arg Ala Ala Thr Val Leu Arg Gln Phe Tyr
 65                  70                  75                  80 agc cac cat gag aag gac act cgc tgc ctg ggt gcg act gca cag cag      288
Ser His His Glu Lys Asp Thr Arg Cys Leu Gly Ala Thr Ala Gln Gln
             85                  90                  95 ttc cac agg cac aag cag ctg atc cga ttc ctg aaa cgg ctc gac agg      336
Phe His Arg His Lys Gln Leu Ile Arg Phe Leu Lys Arg Leu Asp Arg
            100                 105                 110 aac ctc tgg ggc ctg gcg ggc ttg aat tcc tgt cct gtg aag gaa gcc      384
Asn Leu Trp Gly Leu Ala Gly Leu Asn Ser Cys Pro Val Lys Glu Ala
        115                 120                 125 aac cag agt acg ttg gaa aac ttc ttg gaa agg cta aag acg atc atg      432
Asn Gln Ser Thr Leu Glu Asn Phe Leu Glu Arg Leu Lys Thr Ile Met
    130                 135                 140
```

```
ttt gag aaa tat tca aag tgt tcg agc tag                                    462
Phe Glu Lys Tyr Ser Lys Cys Ser Ser
145                 150

<210> SEQ ID NO 7
<211> LENGTH: 462
<212> TYPE: DNA
<213> ORGANISM: Homo sapiens
<220> FEATURE:
<221> NAME/KEY: CDS
<222> LOCATION: (1)..(459)
<223> OTHER INFORMATION: Description: hIL-4/R121H

<400> SEQUENCE: 7 atg ggt ctc acc tcc gaa ctg ctt ccc cct ctg ttc ttc ctg cta gca            48
Met Gly Leu Thr Ser Glu Leu Leu Pro Pro Leu Phe Phe Leu Leu Ala
 1               5                   10                  15 tgt gcc ggc aac ttt gtc cac gga cac aag tgc gat atc acc tta cag            96
Cys Ala Gly Asn Phe Val His Gly His Lys Cys Asp Ile Thr Leu Gln
            20                  25                  30 gag atc atc aaa act ttg aac agc ctc aca gag cag aag act ctg tgc           144
Glu Ile Ile Lys Thr Leu Asn Ser Leu Thr Glu Gln Lys Thr Leu Cys
        35                  40                  45 acc gag ttg acc gta aca gac atc ttt gct gcc tcc aag aac aca act           192
Thr Glu Leu Thr Val Thr Asp Ile Phe Ala Ala Ser Lys Asn Thr Thr
    50                  55                  60 gag aag gaa acc ttc tgc agg gct gcg act gtg ctc cgg cag ttc tac           240
Glu Lys Glu Thr Phe Cys Arg Ala Ala Thr Val Leu Arg Gln Phe Tyr
65                  70                  75                  80 agc cac cat gag aag gac act cgc tgc ctg ggt gcg act gca cag cag           288
Ser His His Glu Lys Asp Thr Arg Cys Leu Gly Ala Thr Ala Gln Gln
                85                  90                  95 ttc cac agg cac aag cag ctg atc cga ttc ctg aaa cgg ctc gac agg           336
Phe His Arg His Lys Gln Leu Ile Arg Phe Leu Lys Arg Leu Asp Arg
            100                 105                 110 aac ctc tgg ggc ctg gcg ggc ttg aat tcc tgt cct gtg aag gaa gcc           384
Asn Leu Trp Gly Leu Ala Gly Leu Asn Ser Cys Pro Val Lys Glu Ala
        115                 120                 125 aac cag agt acg ttg gaa aac ttc ttg gaa agg cta aag acg atc atg           432
Asn Gln Ser Thr Leu Glu Asn Phe Leu Glu Arg Leu Lys Thr Ile Met
    130                 135                 140 cac gag aaa tat tca aag tgt tcg agc tag                                   462
His Glu Lys Tyr Ser Lys Cys Ser Ser
145                 150

<210> SEQ ID NO 8
<211> LENGTH: 462
<212> TYPE: DNA
<213> ORGANISM: Homo sapiens
<220> FEATURE:
<221> NAME/KEY: CDS
<222> LOCATION: (1)..(459)
<223> OTHER INFORMATION: Description: hIL-4/R121I

<400> SEQUENCE: 8 atg ggt ctc acc tcc gaa ctg ctt ccc cct ctg ttc ttc ctg cta gca            48
Met Gly Leu Thr Ser Glu Leu Leu Pro Pro Leu Phe Phe Leu Leu Ala
 1               5                   10                  15 tgt gcc ggc aac ttt gtc cac gga cac aag tgc gat atc acc tta cag            96
Cys Ala Gly Asn Phe Val His Gly His Lys Cys Asp Ile Thr Leu Gln
            20                  25                  30 gag atc atc aaa act ttg aac agc ctc aca gag cag aag act ctg tgc           144
Glu Ile Ile Lys Thr Leu Asn Ser Leu Thr Glu Gln Lys Thr Leu Cys
```

|          |          |          |          |          |          |          |          |          |          |          |          |          |          |          |          |     |
|----------|----------|----------|----------|----------|----------|----------|----------|----------|----------|----------|----------|----------|----------|----------|----------|-----|
|          |          | 35       |          |          |          | 40       |          |          |          | 45       |          |          |          |          |          |     |

```
acc gag ttg acc gta aca gac atc ttt gct gcc tcc aag aac aca act      192
Thr Glu Leu Thr Val Thr Asp Ile Phe Ala Ala Ser Lys Asn Thr Thr
         50                  55                  60 gag aag gaa acc ttc tgc agg gct gcg act gtg ctc cgg cag ttc tac      240
Glu Lys Glu Thr Phe Cys Arg Ala Ala Thr Val Leu Arg Gln Phe Tyr
 65              70                  75                  80 agc cac cat gag aag gac act cgc tgc ctg ggt gcg act gca cag cag      288
Ser His His Glu Lys Asp Thr Arg Cys Leu Gly Ala Thr Ala Gln Gln
                     85                  90                  95 ttc cac agg cac aag cag ctg atc cga ttc ctg aaa cgg ctc gac agg      336
Phe His Arg His Lys Gln Leu Ile Arg Phe Leu Lys Arg Leu Asp Arg
                 100                 105                 110 aac ctc tgg ggc ctg gcg ggc ttg aat tcc tgt cct gtg aag gaa gcc      384
Asn Leu Trp Gly Leu Ala Gly Leu Asn Ser Cys Pro Val Lys Glu Ala
             115                 120                 125 aac cag agt acg ttg gaa aac ttc ttg gaa agg cta aag acg atc atg      432
Asn Gln Ser Thr Leu Glu Asn Phe Leu Glu Arg Leu Lys Thr Ile Met
         130                 135                 140 ata gag aaa tat tca aag tgt tcg agc tag                              462
Ile Glu Lys Tyr Ser Lys Cys Ser Ser
145                 150
```

<210> SEQ ID NO 9
<211> LENGTH: 462
<212> TYPE: DNA
<213> ORGANISM: Homo sapiens
<220> FEATURE:
<221> NAME/KEY: CDS
<222> LOCATION: (1)..(459)
<223> OTHER INFORMATION: Description:  hIL-4/R121K

<400> SEQUENCE: 9

```
atg ggt ctc acc tcc gaa ctg ctt ccc cct ctg ttc ttc ctg cta gca       48
Met Gly Leu Thr Ser Glu Leu Leu Pro Pro Leu Phe Phe Leu Leu Ala
 1               5                  10                  15 tgt gcc ggc aac ttt gtc cac gga cac aag tgc gat atc acc tta cag       96
Cys Ala Gly Asn Phe Val His Gly His Lys Cys Asp Ile Thr Leu Gln
                 20                  25                  30 gag atc atc aaa act ttg aac agc ctc aca gag cag aag act ctg tgc      144
Glu Ile Ile Lys Thr Leu Asn Ser Leu Thr Glu Gln Lys Thr Leu Cys
             35                  40                  45 acc gag ttg acc gta aca gac atc ttt gct gcc tcc aag aac aca act      192
Thr Glu Leu Thr Val Thr Asp Ile Phe Ala Ala Ser Lys Asn Thr Thr
         50                  55                  60 gag aag gaa acc ttc tgc agg gct gcg act gtg ctc cgg cag ttc tac      240
Glu Lys Glu Thr Phe Cys Arg Ala Ala Thr Val Leu Arg Gln Phe Tyr
 65              70                  75                  80 agc cac cat gag aag gac act cgc tgc ctg ggt gcg act gca cag cag      288
Ser His His Glu Lys Asp Thr Arg Cys Leu Gly Ala Thr Ala Gln Gln
                     85                  90                  95 ttc cac agg cac aag cag ctg atc cga ttc ctg aaa cgg ctc gac agg      336
Phe His Arg His Lys Gln Leu Ile Arg Phe Leu Lys Arg Leu Asp Arg
                 100                 105                 110 aac ctc tgg ggc ctg gcg ggc ttg aat tcc tgt cct gtg aag gaa gcc      384
Asn Leu Trp Gly Leu Ala Gly Leu Asn Ser Cys Pro Val Lys Glu Ala
             115                 120                 125 aac cag agt acg ttg gaa aac ttc ttg gaa agg cta aag acg atc atg      432
Asn Gln Ser Thr Leu Glu Asn Phe Leu Glu Arg Leu Lys Thr Ile Met
         130                 135                 140 aaa gag aaa tat tca aag tgt tcg agc tag                              462
```

-continued

```
Lys Glu Lys Tyr Ser Lys Cys Ser Ser
145                 150

<210> SEQ ID NO 10
<211> LENGTH: 462
<212> TYPE: DNA
<213> ORGANISM: Homo sapiens
<220> FEATURE:
<221> NAME/KEY: CDS
<222> LOCATION: (1)..(459)
<223> OTHER INFORMATION: Description:  hIL-4/R121N

<400> SEQUENCE: 10 atg ggt ctc acc tcc gaa ctg ctt ccc cct ctg ttc ttc ctg cta gca      48
Met Gly Leu Thr Ser Glu Leu Leu Pro Pro Leu Phe Phe Leu Leu Ala
1               5                   10                  15 tgt gcc ggc aac ttt gtc cac gga cac aag tgc gat atc acc tta cag      96
Cys Ala Gly Asn Phe Val His Gly His Lys Cys Asp Ile Thr Leu Gln
                20                  25                  30 gag atc atc aaa act ttg aac agc ctc aca gag cag aag act ctg tgc     144
Glu Ile Ile Lys Thr Leu Asn Ser Leu Thr Glu Gln Lys Thr Leu Cys
            35                  40                  45 acc gag ttg acc gta aca gac atc ttt gct gcc tcc aag aac aca act     192
Thr Glu Leu Thr Val Thr Asp Ile Phe Ala Ala Ser Lys Asn Thr Thr
        50                  55                  60 gag aag gaa acc ttc tgc agg gct gcg act gtg ctc cgg cag ttc tac     240
Glu Lys Glu Thr Phe Cys Arg Ala Ala Thr Val Leu Arg Gln Phe Tyr
65                  70                  75                  80 agc cac cat gag aag gac act cgc tgc ctg ggt gcg act gca cag cag     288
Ser His His Glu Lys Asp Thr Arg Cys Leu Gly Ala Thr Ala Gln Gln
                85                  90                  95 ttc cac agg cac aag cag ctg atc cga ttc ctg aaa cgg ctc gac agg     336
Phe His Arg His Lys Gln Leu Ile Arg Phe Leu Lys Arg Leu Asp Arg
            100                 105                 110 aac ctc tgg ggc ctg gcg ggc ttg aat tcc tgt cct gtg aag gaa gcc     384
Asn Leu Trp Gly Leu Ala Gly Leu Asn Ser Cys Pro Val Lys Glu Ala
        115                 120                 125 aac cag agt acg ttg gaa aac ttc ttg gaa agg cta aag acg atc atg     432
Asn Gln Ser Thr Leu Glu Asn Phe Leu Glu Arg Leu Lys Thr Ile Met
130                 135                 140 aac gag aaa tat tca aag tgt tcg agc tag                             462
Asn Glu Lys Tyr Ser Lys Cys Ser Ser
145                 150

<210> SEQ ID NO 11
<211> LENGTH: 462
<212> TYPE: DNA
<213> ORGANISM: Homo sapiens
<220> FEATURE:
<221> NAME/KEY: CDS
<222> LOCATION: (1)..(459)
<223> OTHER INFORMATION: Description:  hIL-4/R121P

<400> SEQUENCE: 11 atg ggt ctc acc tcc caa ctg ctt ccc cct ctg ttc ttc ctg cta gca      48
Met Gly Leu Thr Ser Gln Leu Leu Pro Pro Leu Phe Phe Leu Leu Ala
1               5                   10                  15 tgt gcc ggc aac ttt gtc cac gga cac aag tgc gat atc acc tta cag      96
Cys Ala Gly Asn Phe Val His Gly His Lys Cys Asp Ile Thr Leu Gln
                20                  25                  30 gag atc atc aaa act ttg aac agc ctc aca gag cag aag act ctg tgc     144
Glu Ile Ile Lys Thr Leu Asn Ser Leu Thr Glu Gln Lys Thr Leu Cys
            35                  40                  45
```

```
acc gag ttg acc gta aca gac atc ttt gct gcc tcc aag aac aca act        192
Thr Glu Leu Thr Val Thr Asp Ile Phe Ala Ala Ser Lys Asn Thr Thr
    50                  55                  60 gag aag gaa acc ttc tgc agg gct gcg act gtg ctc cgg cag ttc tac        240
Glu Lys Glu Thr Phe Cys Arg Ala Ala Thr Val Leu Arg Gln Phe Tyr
65                  70                  75                  80 agc cac cat gag aag gac act cgc tgc ctg ggt gcg act gca cag cag        288
Ser His His Glu Lys Asp Thr Arg Cys Leu Gly Ala Thr Ala Gln Gln
                85                  90                  95 ttc cac agg cac aag cag ctg atc cga ttc ctg aaa cgg ctc gac agg        336
Phe His Arg His Lys Gln Leu Ile Arg Phe Leu Lys Arg Leu Asp Arg
            100                 105                 110 aac ctc tgg ggc ctg gcg ggc ttg aat tcc tgt cct gtg aag gaa gcc        384
Asn Leu Trp Gly Leu Ala Gly Leu Asn Ser Cys Pro Val Lys Glu Ala
        115                 120                 125 aac cag agt acg ttg gaa aac ttc ttg gaa agg cta aag acg atc atg        432
Asn Gln Ser Thr Leu Glu Asn Phe Leu Glu Arg Leu Lys Thr Ile Met
    130                 135                 140 cca gag aaa tat tca aag tgt tcg agc tag                                462
Pro Glu Lys Tyr Ser Lys Cys Ser Ser
145                 150

<210> SEQ ID NO 12
<211> LENGTH: 462
<212> TYPE: DNA
<213> ORGANISM: Homo sapiens
<220> FEATURE:
<221> NAME/KEY: CDS
<222> LOCATION: (1)..(459)
<223> OTHER INFORMATION: Description: hIL-4/R121T

<400> SEQUENCE: 12 atg ggt ctc acc tcc gaa ctg ctt ccc cct ctg ttc ttc ctg cta gca        48
Met Gly Leu Thr Ser Glu Leu Leu Pro Pro Leu Phe Phe Leu Leu Ala
1               5                   10                  15 tgt gcc ggc aac ttt gtc cac gga cac aag tgc gat atc acc tta cag        96
Cys Ala Gly Asn Phe Val His Gly His Lys Cys Asp Ile Thr Leu Gln
            20                  25                  30 gag atc atc aaa act ttg aac agc ctc aca gag cag aag act ctg tgc       144
Glu Ile Ile Lys Thr Leu Asn Ser Leu Thr Glu Gln Lys Thr Leu Cys
        35                  40                  45 acc gag ttg acc gta aca gac atc ttt gct gcc tcc aag aac aca act       192
Thr Glu Leu Thr Val Thr Asp Ile Phe Ala Ala Ser Lys Asn Thr Thr
    50                  55                  60 gag aag gaa acc ttc tgc agg gct gcg act gtg ctc cgg cag ttc tac       240
Glu Lys Glu Thr Phe Cys Arg Ala Ala Thr Val Leu Arg Gln Phe Tyr
65                  70                  75                  80 agc cac cat gag aag gac act cgc tgc ctg ggt gcg act gca cag cag       288
Ser His His Glu Lys Asp Thr Arg Cys Leu Gly Ala Thr Ala Gln Gln
                85                  90                  95 ttc cac agg cac aag cag ctg atc cga ttc ctg aaa cgg ctc gac agg       336
Phe His Arg His Lys Gln Leu Ile Arg Phe Leu Lys Arg Leu Asp Arg
            100                 105                 110 aac ctc tgg ggc ctg gcg ggc ttg aat tcc tgt cct gtg aag gaa gcc       384
Asn Leu Trp Gly Leu Ala Gly Leu Asn Ser Cys Pro Val Lys Glu Ala
        115                 120                 125 aac cag agt acg ttg gaa aac ttc ttg gaa agg cta aag acg atc atg       432
Asn Gln Ser Thr Leu Glu Asn Phe Leu Glu Arg Leu Lys Thr Ile Met
    130                 135                 140 act gag aaa tat tca aag tgt tcg agc tag                               462
Thr Glu Lys Tyr Ser Lys Cys Ser Ser
145                 150
```

<210> SEQ ID NO 13
<211> LENGTH: 462
<212> TYPE: DNA
<213> ORGANISM: Homo sapiens
<220> FEATURE:
<221> NAME/KEY: CDS
<222> LOCATION: (1)..(459)
<223> OTHER INFORMATION: Description: hIL-4/R121W

<400> SEQUENCE: 13

| atg | ggt | ctc | acc | tcc | gaa | ctg | ctt | ccc | cct | ctg | ttc | ttc | ctg | cta | gca | 48 |
| Met | Gly | Leu | Thr | Ser | Glu | Leu | Leu | Pro | Pro | Leu | Phe | Phe | Leu | Leu | Ala | |
| 1 | | | | 5 | | | | | 10 | | | | | 15 | | |

| tgt | gcc | ggc | aac | ttt | gtc | cac | gga | cac | aag | tgc | gat | atc | acc | tta | cag | 96 |
| Cys | Ala | Gly | Asn | Phe | Val | His | Gly | His | Lys | Cys | Asp | Ile | Thr | Leu | Gln | |
| | | | 20 | | | | | 25 | | | | | 30 | | | |

| gag | atc | atc | aaa | act | ttg | aac | agc | ctc | aca | gag | cag | aag | act | ctg | tgc | 144 |
| Glu | Ile | Ile | Lys | Thr | Leu | Asn | Ser | Leu | Thr | Glu | Gln | Lys | Thr | Leu | Cys | |
| | | 35 | | | | | 40 | | | | | 45 | | | | |

| acc | gag | ttg | acc | gta | aca | gac | atc | ttt | gct | gcc | tcc | aag | aac | aca | act | 192 |
| Thr | Glu | Leu | Thr | Val | Thr | Asp | Ile | Phe | Ala | Ala | Ser | Lys | Asn | Thr | Thr | |
| | 50 | | | | | 55 | | | | | 60 | | | | | |

| gag | aag | gaa | acc | ttc | tgc | agg | gct | gcg | act | gtg | ctc | cgg | cag | ttc | tac | 240 |
| Glu | Lys | Glu | Thr | Phe | Cys | Arg | Ala | Ala | Thr | Val | Leu | Arg | Gln | Phe | Tyr | |
| 65 | | | | | 70 | | | | | 75 | | | | | 80 | |

| agc | cac | cat | gag | aag | gac | act | cgc | tgc | ctg | ggt | gcg | act | gca | cag | cag | 288 |
| Ser | His | His | Glu | Lys | Asp | Thr | Arg | Cys | Leu | Gly | Ala | Thr | Ala | Gln | Gln | |
| | | | | 85 | | | | | 90 | | | | | 95 | | |

| ttc | cac | agg | cac | aag | cag | ctg | atc | cga | ttc | ctg | aaa | cgg | ctc | gac | agg | 336 |
| Phe | His | Arg | His | Lys | Gln | Leu | Ile | Arg | Phe | Leu | Lys | Arg | Leu | Asp | Arg | |
| | | | 100 | | | | | 105 | | | | | 110 | | | |

| aac | ctc | tgg | ggc | ctg | gcg | ggc | ttg | aat | tcc | tgt | cct | gtg | aag | gaa | gcc | 384 |
| Asn | Leu | Trp | Gly | Leu | Ala | Gly | Leu | Asn | Ser | Cys | Pro | Val | Lys | Glu | Ala | |
| | | 115 | | | | | 120 | | | | | 125 | | | | |

| aac | cag | agt | acg | ttg | gaa | aac | ttc | ttg | gaa | agg | cta | aag | acg | atc | atg | 432 |
| Asn | Gln | Ser | Thr | Leu | Glu | Asn | Phe | Leu | Glu | Arg | Leu | Lys | Thr | Ile | Met | |
| | 130 | | | | | 135 | | | | | 140 | | | | | |

| tgg | gag | aaa | tat | tca | aag | tgt | tcg | agc | tag | | | | | | | 462 |
| Trp | Glu | Lys | Tyr | Ser | Lys | Cys | Ser | Ser | | | | | | | | |
| 145 | | | | | 150 | | | | | | | | | | | |

<210> SEQ ID NO 14
<211> LENGTH: 462
<212> TYPE: DNA
<213> ORGANISM: Homo sapiens
<220> FEATURE:
<221> NAME/KEY: CDS
<222> LOCATION: (1)..(459)
<223> OTHER INFORMATION: Description: hIL-4/Y124A

<400> SEQUENCE: 14

| atg | ggt | ctc | acc | tcc | gaa | ctg | ctt | ccc | cct | ctg | ttc | ttc | ctg | cta | gca | 48 |
| Met | Gly | Leu | Thr | Ser | Glu | Leu | Leu | Pro | Pro | Leu | Phe | Phe | Leu | Leu | Ala | |
| 1 | | | | 5 | | | | | 10 | | | | | 15 | | |

| tgt | gcc | ggc | aac | ttt | gtc | cac | gga | cac | aag | tgc | gat | atc | acc | tta | cag | 96 |
| Cys | Ala | Gly | Asn | Phe | Val | His | Gly | His | Lys | Cys | Asp | Ile | Thr | Leu | Gln | |
| | | | 20 | | | | | 25 | | | | | 30 | | | |

| gag | atc | atc | aaa | act | ttg | aac | agc | ctc | aca | gag | cag | aag | act | ctg | tgc | 144 |
| Glu | Ile | Ile | Lys | Thr | Leu | Asn | Ser | Leu | Thr | Glu | Gln | Lys | Thr | Leu | Cys | |
| | | 35 | | | | | 40 | | | | | 45 | | | | |

| acc | gag | ttg | acc | gta | aca | gac | atc | ttt | gct | gcc | tcc | aag | aac | aca | act | 192 |
| Thr | Glu | Leu | Thr | Val | Thr | Asp | Ile | Phe | Ala | Ala | Ser | Lys | Asn | Thr | Thr | |
| | 50 | | | | | 55 | | | | | 60 | | | | | | |

```
gag aag gaa acc ttc tgc agg gct gcg act gtg ctc cgg cag ttc tac      240
Glu Lys Glu Thr Phe Cys Arg Ala Ala Thr Val Leu Arg Gln Phe Tyr
 65              70                  75                  80 agc cac cat gag aag gac act cgc tgc ctg ggt gcg act gca cag cag      288
Ser His His Glu Lys Asp Thr Arg Cys Leu Gly Ala Thr Ala Gln Gln
                 85                  90                  95 ttc cac agg cac aag cag ctg atc cga ttc ctg aaa cgg ctc gac agg      336
Phe His Arg His Lys Gln Leu Ile Arg Phe Leu Lys Arg Leu Asp Arg
             100                 105                 110 aac ctc tgg ggc ctg gcg ggc ttg aat tcc tgt cct gtg aag gaa gcc      384
Asn Leu Trp Gly Leu Ala Gly Leu Asn Ser Cys Pro Val Lys Glu Ala
         115                 120                 125 aac cag agt acg ttg gaa aac ttc ttg gaa agg cta aag acg atc atg      432
Asn Gln Ser Thr Leu Glu Asn Phe Leu Glu Arg Leu Lys Thr Ile Met
     130                 135                 140 gca gag aaa gca tca aag tgt tcg agc tag                              462
Ala Glu Lys Ala Ser Lys Cys Ser Ser
145                 150
```

<210> SEQ ID NO 15
<211> LENGTH: 462
<212> TYPE: DNA
<213> ORGANISM: Homo sapiens
<220> FEATURE:
<221> NAME/KEY: CDS
<222> LOCATION: (1)..(459)
<223> OTHER INFORMATION: Description: IL-4/Y124Q

<400> SEQUENCE: 15

```
atg ggt ctc acc tcc caa ctg ctt ccc cct ctg ttc ttc ctg cta gca       48
Met Gly Leu Thr Ser Gln Leu Leu Pro Pro Leu Phe Phe Leu Leu Ala
 1               5                  10                  15 tgt gcc ggc aac ttt gtc cac gga cac aag tgc gat atc acc tta cag       96
Cys Ala Gly Asn Phe Val His Gly His Lys Cys Asp Ile Thr Leu Gln
             20                  25                  30 gag atc atc aaa act ttg aac agc ctc aca gag cag aag act ctg tgc      144
Glu Ile Ile Lys Thr Leu Asn Ser Leu Thr Glu Gln Lys Thr Leu Cys
         35                  40                  45 acc gag ttg acc gta aca gac atc ttt gct gcc tcc aag aac aca act      192
Thr Glu Leu Thr Val Thr Asp Ile Phe Ala Ala Ser Lys Asn Thr Thr
     50                  55                  60 gag aag gaa acc ttc tgc agg gct gcg act gtg ctc cgg cag ttc tac      240
Glu Lys Glu Thr Phe Cys Arg Ala Ala Thr Val Leu Arg Gln Phe Tyr
 65              70                  75                  80 agc cac cat gag aag gac act cgc tgc ctg ggt gcg act gca cag cag      288
Ser His His Glu Lys Asp Thr Arg Cys Leu Gly Ala Thr Ala Gln Gln
                 85                  90                  95 ttc cac agg cac aag cag ctg atc cga ttc ctg aaa cgg ctc gac agg      336
Phe His Arg His Lys Gln Leu Ile Arg Phe Leu Lys Arg Leu Asp Arg
             100                 105                 110 aac ctc tgg ggc ctg gcg ggc ttg aat tcc tgt cct gtg aag gaa gcc      384
Asn Leu Trp Gly Leu Ala Gly Leu Asn Ser Cys Pro Val Lys Glu Ala
         115                 120                 125 aac cag agt acg ttg gaa aac ttc ttg gaa agg cta aag acg atc atg      432
Asn Gln Ser Thr Leu Glu Asn Phe Leu Glu Arg Leu Lys Thr Ile Met
     130                 135                 140 aga gag aaa caa tca aag tgt tcg agc tag                              462
Arg Glu Lys Gln Ser Lys Cys Ser Ser
145                 150
```

-continued

```
<210> SEQ ID NO 16
<211> LENGTH: 462
<212> TYPE: DNA
<213> ORGANISM: Homo sapiens
<220> FEATURE:
<221> NAME/KEY: CDS
<222> LOCATION: (1)..(459)
<223> OTHER INFORMATION: Description:  IL-4/Y124R

<400> SEQUENCE: 16 atg ggt ctc acc tcc caa ctg ctt ccc cct ctg ttc ttc ctg cta gca      48
Met Gly Leu Thr Ser Gln Leu Leu Pro Pro Leu Phe Phe Leu Leu Ala
1               5                   10                  15 tgt gcc ggc aac ttt gtc cac gga cac aag tgc gat atc acc tta cag      96
Cys Ala Gly Asn Phe Val His Gly His Lys Cys Asp Ile Thr Leu Gln
                20                  25                  30 gag atc atc aaa act ttg aac agc ctc aca gag cag aag act ctg tgc     144
Glu Ile Ile Lys Thr Leu Asn Ser Leu Thr Glu Gln Lys Thr Leu Cys
            35                  40                  45 acc gag ttg acc gta aca gac atc ttt gct gcc tcc aag aac aca act     192
Thr Glu Leu Thr Val Thr Asp Ile Phe Ala Ala Ser Lys Asn Thr Thr
        50                  55                  60 gag aag gaa acc ttc tgc agg gct gcg act gtg ctc cgg cag ttc tac     240
Glu Lys Glu Thr Phe Cys Arg Ala Ala Thr Val Leu Arg Gln Phe Tyr
65                  70                  75                  80 agc cac cat gag aag gac act cgc tgc ctg ggt gcg act gca cag cag     288
Ser His His Glu Lys Asp Thr Arg Cys Leu Gly Ala Thr Ala Gln Gln
                85                  90                  95 ttc cac agg cac aag cag ctg atc cga ttc ctg aaa cgg ctc gac agg     336
Phe His Arg His Lys Gln Leu Ile Arg Phe Leu Lys Arg Leu Asp Arg
                100                 105                 110 aac ctc tgg ggc ctg gcg ggc ttg aat tcc tgt cct gtg aag gaa gcc     384
Asn Leu Trp Gly Leu Ala Gly Leu Asn Ser Cys Pro Val Lys Glu Ala
            115                 120                 125 aac cag agt acg ttg gaa aac ttc ttg gaa agg cta aag acg atc atg     432
Asn Gln Ser Thr Leu Glu Asn Phe Leu Glu Arg Leu Lys Thr Ile Met
        130                 135                 140 aga gag aaa cga tca aag tgt tcg agc tag                             462
Arg Glu Lys Arg Ser Lys Cys Ser Ser
145                 150

<210> SEQ ID NO 17
<211> LENGTH: 462
<212> TYPE: DNA
<213> ORGANISM: Homo sapiens
<220> FEATURE:
<221> NAME/KEY: CDS
<222> LOCATION: (1)..(459)
<223> OTHER INFORMATION: Description:  IL-4/Y124S

<400> SEQUENCE: 17 atg ggt ctc acc tcc caa ctg ctt ccc cct ctg ttc ttc ctg cta gca      48
Met Gly Leu Thr Ser Gln Leu Leu Pro Pro Leu Phe Phe Leu Leu Ala
1               5                   10                  15 tgt gcc ggc aac ttt gtc cac gga cac aag tgc gat atc acc tta cag      96
Cys Ala Gly Asn Phe Val His Gly His Lys Cys Asp Ile Thr Leu Gln
                20                  25                  30 gag atc atc aaa act ttg aac agc ctc aca gag cag aag act ctg tgc     144
Glu Ile Ile Lys Thr Leu Asn Ser Leu Thr Glu Gln Lys Thr Leu Cys
            35                  40                  45 acc gag ttg acc gta aca gac atc ttt gct gcc tcc aag aac aca act     192
Thr Glu Leu Thr Val Thr Asp Ile Phe Ala Ala Ser Lys Asn Thr Thr
        50                  55                  60
```

-continued

```
gag aag gaa acc ttc tgc agg gct gcg act gtg ctc cgg cag ttc tac      240
Glu Lys Glu Thr Phe Cys Arg Ala Ala Thr Val Leu Arg Gln Phe Tyr
 65                  70                  75                  80 agc cac cat gag aag gac act cgc tgc ctg ggt gcg act gca cag cag      288
Ser His His Glu Lys Asp Thr Arg Cys Leu Gly Ala Thr Ala Gln Gln
             85                  90                  95 ttc cac agg cac aag cag ctg atc cga ttc ctg aaa cgg ctc gac agg      336
Phe His Arg His Lys Gln Leu Ile Arg Phe Leu Lys Arg Leu Asp Arg
        100                 105                 110 aac ctc tgg ggc ctg gcg ggc ttg aat tcc tgt cct gtg aag gaa gcc      384
Asn Leu Trp Gly Leu Ala Gly Leu Asn Ser Cys Pro Val Lys Glu Ala
    115                 120                 125 aac cag agt acg ttg gaa aac ttc ttg gaa agg cta aag acg atc atg      432
Asn Gln Ser Thr Leu Glu Asn Phe Leu Glu Arg Leu Lys Thr Ile Met
130                 135                 140 aga gag aaa tca tca aag tgt tcg agc tag                              462
Arg Glu Lys Ser Ser Lys Cys Ser Ser
145                 150
```

<210> SEQ ID NO 18
<211> LENGTH: 462
<212> TYPE: DNA
<213> ORGANISM: Homo sapiens
<220> FEATURE:
<221> NAME/KEY: CDS
<222> LOCATION: (1)..(459)
<223> OTHER INFORMATION: Description: IL-4/Y124T

<400> SEQUENCE: 18

```
atg ggt ctc acc tcc caa ctg ctt ccc cct ctg ttc ttc ctg cta gca       48
Met Gly Leu Thr Ser Gln Leu Leu Pro Pro Leu Phe Phe Leu Leu Ala
  1               5                  10                  15 tgt gcc ggc aac ttt gtc cac gga cac aag tgc gat atc acc tta cag       96
Cys Ala Gly Asn Phe Val His Gly His Lys Cys Asp Ile Thr Leu Gln
             20                  25                  30 gag atc atc aaa act ttg aac agc ctc aca gag cag aag act ctg tgc      144
Glu Ile Ile Lys Thr Leu Asn Ser Leu Thr Glu Gln Lys Thr Leu Cys
         35                  40                  45 acc gag ttg acc gta aca gac atc ttt gct gcc tcc aag aac aca act      192
Thr Glu Leu Thr Val Thr Asp Ile Phe Ala Ala Ser Lys Asn Thr Thr
     50                  55                  60 gag aag gaa acc ttc tgc agg gct gcg act gtg ctc cgg cag ttc tac      240
Glu Lys Glu Thr Phe Cys Arg Ala Ala Thr Val Leu Arg Gln Phe Tyr
 65                  70                  75                  80 agc cac cat gag aag gac act cgc tgc ctg ggt gcg act gca cag cag      288
Ser His His Glu Lys Asp Thr Arg Cys Leu Gly Ala Thr Ala Gln Gln
             85                  90                  95 ttc cac agg cac aag cag ctg atc cga ttc ctg aaa cgg ctc gac agg      336
Phe His Arg His Lys Gln Leu Ile Arg Phe Leu Lys Arg Leu Asp Arg
        100                 105                 110 aac ctc tgg ggc ctg gcg ggc ttg aat tcc tgt cct gtg aag gaa gcc      384
Asn Leu Trp Gly Leu Ala Gly Leu Asn Ser Cys Pro Val Lys Glu Ala
    115                 120                 125 aac cag agt acg ttg gaa aac ttc ttg gaa agg cta aag acg atc atg      432
Asn Gln Ser Thr Leu Glu Asn Phe Leu Glu Arg Leu Lys Thr Ile Met
130                 135                 140 aga gag aaa aca tca aag tgt tcg agc tag                              462
Arg Glu Lys Thr Ser Lys Cys Ser Ser
145                 150
```

<210> SEQ ID NO 19
<211> LENGTH: 462

-continued

```
<212> TYPE: DNA
<213> ORGANISM: Homo sapiens
<220> FEATURE:
<221> NAME/KEY: CDS
<222> LOCATION: (1)..(459)
<223> OTHER INFORMATION: Description:  IL-4/Y124A/S125A

<400> SEQUENCE: 19 atg ggt ctc acc tcc caa ctg ctt ccc cct ctg ttc ttc ctg cta gca      48
Met Gly Leu Thr Ser Gln Leu Leu Pro Pro Leu Phe Phe Leu Leu Ala
 1               5                  10                  15 tgt gcc ggc aac ttt gtc cac gga cac aag tgc gat atc acc tta cag      96
Cys Ala Gly Asn Phe Val His Gly His Lys Cys Asp Ile Thr Leu Gln
                 20                  25                  30 gag atc atc aaa act ttg aac agc ctc aca gag cag aag act ctg tgc     144
Glu Ile Ile Lys Thr Leu Asn Ser Leu Thr Glu Gln Lys Thr Leu Cys
             35                  40                  45 acc gag ttg acc gta aca gac atc ttt gct gcc tcc aag aac aca act     192
Thr Glu Leu Thr Val Thr Asp Ile Phe Ala Ala Ser Lys Asn Thr Thr
         50                  55                  60 gag aag gaa acc ttc tgc agg gct gcg act gtg ctc cgg cag ttc tac     240
Glu Lys Glu Thr Phe Cys Arg Ala Ala Thr Val Leu Arg Gln Phe Tyr
 65                  70                  75                  80 agc cac cat gag aag gac act cgc tgc ctg ggt gcg act gca cag cag     288
Ser His His Glu Lys Asp Thr Arg Cys Leu Gly Ala Thr Ala Gln Gln
                 85                  90                  95 ttc cac agg cac aag cag ctg atc cga ttc ctg aaa cgg ctc gac agg     336
Phe His Arg His Lys Gln Leu Ile Arg Phe Leu Lys Arg Leu Asp Arg
            100                 105                 110 aac ctc tgg ggc ctg gcg ggc ttg aat tcc tgt cct gtg aag gaa gcc     384
Asn Leu Trp Gly Leu Ala Gly Leu Asn Ser Cys Pro Val Lys Glu Ala
        115                 120                 125 aac cag agt acg ttg gaa aac ttc ttg gaa agg cta aag acg atc atg     432
Asn Gln Ser Thr Leu Glu Asn Phe Leu Glu Arg Leu Lys Thr Ile Met
    130                 135                 140 aga gag aaa gct gct aag tgt tcg agc tag                             462
Arg Glu Lys Ala Ala Lys Cys Ser Ser
145                 150

<210> SEQ ID NO 20
<211> LENGTH: 462
<212> TYPE: DNA
<213> ORGANISM: Homo sapiens
<220> FEATURE:
<221> NAME/KEY: CDS
<222> LOCATION: (1)..(459)
<223> OTHER INFORMATION: Description:  IL-4/T13D/R121E

<400> SEQUENCE: 20 atg ggt ctc acc tcc caa ctg ctt ccc cct ctg ttc ttc ctg cta gca      48
Met Gly Leu Thr Ser Gln Leu Leu Pro Pro Leu Phe Phe Leu Leu Ala
 1               5                  10                  15 tgt gcc ggc aac ttt gtc cac gga cac aag tgc gat atc acc tta cag      96
Cys Ala Gly Asn Phe Val His Gly His Lys Cys Asp Ile Thr Leu Gln
                 20                  25                  30 gag atc atc aaa gat ttg aac agc ctc aca gag cag aag act ctg tgc     144
Glu Ile Ile Lys Asp Leu Asn Ser Leu Thr Glu Gln Lys Thr Leu Cys
             35                  40                  45 acc gag ttg acc gta aca gac atc ttt gct gcc tcc aag aac aca act     192
Thr Glu Leu Thr Val Thr Asp Ile Phe Ala Ala Ser Lys Asn Thr Thr
         50                  55                  60 gag aag gaa acc ttc tgc agg gct gcg act gtg ctc cgg cag ttc tac     240
Glu Lys Glu Thr Phe Cys Arg Ala Ala Thr Val Leu Arg Gln Phe Tyr
```

```
agc cac cat gag aag gac act cgc tgc ctg ggt gcg act gca cag cag        288
Ser His His Glu Lys Asp Thr Arg Cys Leu Gly Ala Thr Ala Gln Gln
                 85                  90                  95 ttc cac agg cac aag cag ctg atc cga ttc ctg aaa cgg ctc gac agg        336
Phe His Arg His Lys Gln Leu Ile Arg Phe Leu Lys Arg Leu Asp Arg
            100                 105                 110 aac ctc tgg ggc ctg gcg ggc ttg aat tcc tgt cct gtg aag gaa gcc        384
Asn Leu Trp Gly Leu Ala Gly Leu Asn Ser Cys Pro Val Lys Glu Ala
        115                 120                 125 aac cag agt acg ttg gaa aac ttc ttg gaa agg cta aag acg atc atg        432
Asn Gln Ser Thr Leu Glu Asn Phe Leu Glu Arg Leu Lys Thr Ile Met
    130                 135                 140 gaa gag aaa tat tca aag tgt tcg agc tag                                462
Glu Glu Lys Tyr Ser Lys Cys Ser Ser
145                 150

<210> SEQ ID NO 21
<211> LENGTH: 462
<212> TYPE: DNA
<213> ORGANISM: Homo sapiens
<220> FEATURE:
<221> NAME/KEY: CDS
<222> LOCATION: (1)..(459)
<223> OTHER INFORMATION: Description: hIL-4/R121T/E122F/Y124Q

<400> SEQUENCE: 21 atg ggt ctc acc tcc caa ctg ctt ccc cct ctg ttc ttc ctg cta gca         48
Met Gly Leu Thr Ser Gln Leu Leu Pro Pro Leu Phe Phe Leu Leu Ala
  1               5                  10                  15 tgt gcc ggc aac ttt gtc cac gga cac aag tgc gat atc acc tta cag         96
Cys Ala Gly Asn Phe Val His Gly His Lys Cys Asp Ile Thr Leu Gln
             20                  25                  30 gag atc atc aaa act ttg aac agc ctc aca gag cag aag act ctg tgc        144
Glu Ile Ile Lys Thr Leu Asn Ser Leu Thr Glu Gln Lys Thr Leu Cys
         35                  40                  45 acc gag ttg acc gta aca gac atc ttt gct gcc tcc aag aac aca act        192
Thr Glu Leu Thr Val Thr Asp Ile Phe Ala Ala Ser Lys Asn Thr Thr
     50                  55                  60 gag aag gaa acc ttc tgc agg gct gcg act gtg ctc cgg cag ttc tac        240
Glu Lys Glu Thr Phe Cys Arg Ala Ala Thr Val Leu Arg Gln Phe Tyr
 65                  70                  75                  80 agc cac cat gag aag gac act cgc tgc ctg ggt gcg act gca cag cag        288
Ser His His Glu Lys Asp Thr Arg Cys Leu Gly Ala Thr Ala Gln Gln
                 85                  90                  95 ttc cac agg cac aag cag ctg atc cga ttc ctg aaa cgg ctc gac agg        336
Phe His Arg His Lys Gln Leu Ile Arg Phe Leu Lys Arg Leu Asp Arg
            100                 105                 110 aac ctc tgg ggc ctg gcg ggc ttg aat tcc tgt cct gtg aag gaa gcc        384
Asn Leu Trp Gly Leu Ala Gly Leu Asn Ser Cys Pro Val Lys Glu Ala
        115                 120                 125 aac cag agt acg ttg gaa aac ttc ttg gaa agg cta aag acg atc atg        432
Asn Gln Ser Thr Leu Glu Asn Phe Leu Glu Arg Leu Lys Thr Ile Met
    130                 135                 140 acc ttc aaa cag tca aag tgt tcg agc tag                                462
Thr Phe Lys Gln Ser Lys Cys Ser Ser
145                 150

<210> SEQ ID NO 22
<211> LENGTH: 24
<212> TYPE: DNA
<213> ORGANISM: Homo sapiens
```

-continued

```
<220> FEATURE:
<221> NAME/KEY:
<222> LOCATION: (1)..(24)
<223> OTHER INFORMATION: Description: 5' PCR Primer, IL-4

<400> SEQUENCE: 22
cgcggatcca tgggtctcac ctcc                                           24

<210> SEQ ID NO 23
<211> LENGTH: 29
<212> TYPE: DNA
<213> ORGANISM: Homo sapiens
<220> FEATURE:
<221> NAME/KEY:
<222> LOCATION: (1)..(29)
<223> OTHER INFORMATION: Description: 3' PCR Primer, IL-4

<400> SEQUENCE: 23
cgctctagac tagctcgaac actttgaat                                      29

<210> SEQ ID NO 24
<211> LENGTH: 28
<212> TYPE: DNA
<213> ORGANISM: Homo sapiens
<220> FEATURE:
<221> NAME/KEY:
<222> LOCATION: (1)..(28)
<223> OTHER INFORMATION: Description: Mutagenesis Primer, IL-4/R121A

<400> SEQUENCE: 24
ctaaagacga tcatggctga gaaatatt                                       28

<210> SEQ ID NO 25
<211> LENGTH: 30
<212> TYPE: DNA
<213> ORGANISM: Homo sapiens
<220> FEATURE:
<221> NAME/KEY:
<222> LOCATION: (1)..(30)
<223> OTHER INFORMATION: Description: Mutagenesis Primer, IL-4/R121D

<400> SEQUENCE: 25
gctaaagacg atcatggacg agaaatattc                                     30

<210> SEQ ID NO 26
<211> LENGTH: 30
<212> TYPE: DNA
<213> ORGANISM: Homo sapiens
<220> FEATURE:
<221> NAME/KEY:
<222> LOCATION: (1)..(30)
<223> OTHER INFORMATION: Description: Mutagenesis Primer, IL-4/R121E

<400> SEQUENCE: 26
gctaaagacg atcatggaag agaaatattc                                     30

<210> SEQ ID NO 27
<211> LENGTH: 28
<212> TYPE: DNA
<213> ORGANISM: Homo sapiens
<220> FEATURE:
<221> NAME/KEY:
<222> LOCATION: (1)..(28)
<223> OTHER INFORMATION: Description: Mutagenesis Primer, IL-4/R121F

<400> SEQUENCE: 27
ctaaagacga tcatgtttga gaaatatt                                       28
```

<210> SEQ ID NO 28
<211> LENGTH: 28
<212> TYPE: DNA
<213> ORGANISM: Homo sapiens
<220> FEATURE:
<221> NAME/KEY:
<222> LOCATION: (1)..(28)
<223> OTHER INFORMATION: Description: Mutagenesis Primer, IL-4/R121H

<400> SEQUENCE: 28
ctaaagacga tcatgcacga gaaatatt                                    28

<210> SEQ ID NO 29
<211> LENGTH: 28
<212> TYPE: DNA
<213> ORGANISM: Homo sapiens
<220> FEATURE:
<221> NAME/KEY:
<222> LOCATION: (1)..(28)
<223> OTHER INFORMATION: Description: Mutagenesis Primer, IL-4/R121I

<400> SEQUENCE: 29
ctaaagacga tcatgataga gaaatatt                                    28

<210> SEQ ID NO 30
<211> LENGTH: 28
<212> TYPE: DNA
<213> ORGANISM: Homo sapiens
<220> FEATURE:
<221> NAME/KEY:
<222> LOCATION: (1)..(28)
<223> OTHER INFORMATION: Description: Mutagenesis Primer, IL-4/R121K

<400> SEQUENCE: 30
ctaaagacga tcatgaaaga gaaatatt                                    28

<210> SEQ ID NO 31
<211> LENGTH: 28
<212> TYPE: DNA
<213> ORGANISM: Homo sapiens
<220> FEATURE:
<221> NAME/KEY:
<222> LOCATION: (1)..(28)
<223> OTHER INFORMATION: Description: Mutagenesis Primer, IL-4/R121N

<400> SEQUENCE: 31
ctaaagacga tcatgaacga gaaatatt                                    28

<210> SEQ ID NO 32
<211> LENGTH: 30
<212> TYPE: DNA
<213> ORGANISM: Homo sapiens
<220> FEATURE:
<221> NAME/KEY:
<222> LOCATION: (1)..(30)
<223> OTHER INFORMATION: Description: Mutagenesis Primer, IL-4/R121P

<400> SEQUENCE: 32
gctaaagacg atcatgccag agaaatattc                                  30

<210> SEQ ID NO 33
<211> LENGTH: 28
<212> TYPE: DNA
<213> ORGANISM: Homo sapiens
<220> FEATURE:
<221> NAME/KEY:
<222> LOCATION: (1)..(28)
<223> OTHER INFORMATION: Description: Mutagenesis Primer, IL-4/R121T

```
<400> SEQUENCE: 33
ctaaagacga tcatgactga gaaatatt                                          28

<210> SEQ ID NO 34
<211> LENGTH: 28
<212> TYPE: DNA
<213> ORGANISM: Homo sapiens
<220> FEATURE:
<221> NAME/KEY: primer_bind
<222> LOCATION: (1)..(28)
<223> OTHER INFORMATION: Description: Mutagenesis Primer, IL-4/R121W

<400> SEQUENCE: 34
ctaaagacga tcatgtggga gaaatatt                                          28

<210> SEQ ID NO 35
<211> LENGTH: 28
<212> TYPE: DNA
<213> ORGANISM: Homo sapiens
<220> FEATURE:
<221> NAME/KEY:
<222> LOCATION: (1)..(28)
<223> OTHER INFORMATION: Description: Mutagenesis Primer, IL-4/Y124A

<400> SEQUENCE: 35
atcatgagag agaaagcatc aaagtgtt                                          28

<210> SEQ ID NO 36
<211> LENGTH: 28
<212> TYPE: DNA
<213> ORGANISM: Homo sapiens
<220> FEATURE:
<221> NAME/KEY:
<222> LOCATION: (1)..(28)
<223> OTHER INFORMATION: Description: Mutagenesis Primer, IL-4/Y124Q

<400> SEQUENCE: 36
atcatgagag agaaacaatc aaagtgtt                                          28

<210> SEQ ID NO 37
<211> LENGTH: 28
<212> TYPE: DNA
<213> ORGANISM: Homo sapiens
<220> FEATURE:
<221> NAME/KEY:
<222> LOCATION: (1)..(28)
<223> OTHER INFORMATION: Description: Mutagenesis Primer, IL-4/Y124R

<400> SEQUENCE: 37
atcatgagag agaaacgatc aaagtgtt                                          28

<210> SEQ ID NO 38
<211> LENGTH: 28
<212> TYPE: DNA
<213> ORGANISM: Homo sapiens
<220> FEATURE:
<221> NAME/KEY:
<222> LOCATION: (1)..(28)
<223> OTHER INFORMATION: Description: Mutagenesis Primer, IL-4/Y124S

<400> SEQUENCE: 38
atcatgagag agaaatcatc aaagtgtt                                          28

<210> SEQ ID NO 39
<211> LENGTH: 28
<212> TYPE: DNA
```

```
<213> ORGANISM: Homo sapiens
<220> FEATURE:
<221> NAME/KEY:
<222> LOCATION: (1)..(28)
<223> OTHER INFORMATION: Description: Mutagenesis Primer, IL-4/Y124T

<400> SEQUENCE: 39
atcatgagag agaaaacatc aaagtgtt                              28

<210> SEQ ID NO 40
<211> LENGTH: 33
<212> TYPE: DNA
<213> ORGANISM: Homo sapiens
<220> FEATURE:
<221> NAME/KEY:
<222> LOCATION: (1)..(33)
<223> OTHER INFORMATION: Description: Mutagenesis Primer,
      IL-4/Y124A/S125A

<400> SEQUENCE: 40
cgatcatgag agagaaagct gctaagtgtt cga                        33

<210> SEQ ID NO 41
<211> LENGTH: 28
<212> TYPE: DNA
<213> ORGANISM: Homo sapiens
<220> FEATURE:
<221> NAME/KEY:
<222> LOCATION: (1)..(28)
<223> OTHER INFORMATION: Description: Mutagenesis Primer,
      IL-4/T13D:T13D substitution

<400> SEQUENCE: 41
caggagatca tcaaagattt gaacagcc                              28

<210> SEQ ID NO 42
<211> LENGTH: 34
<212> TYPE: DNA
<213> ORGANISM: Homo sapiens
<220> FEATURE:
<221> NAME/KEY:
<222> LOCATION: (1)..(34)
<223> OTHER INFORMATION: Description: Mutagenesis Primer,
      IL-4/R121T/E122F/Y124Q

<400> SEQUENCE: 42
gctaaagacg atcatgacct tcaaacagtc aaag                       34
```

T-CELL SELECTIVE INTERLEUKIN-4 AGONISTS

CROSS-REFERENCE TO RELATED APPLICATIONS

This application is a continuation-in-part of U.S. application Ser. No. 08/874,697, filed Jun. 13, 1997 now U.S. Pat. No. 5,986,059, which claims the benefit of U.S. Provisional Application Nos. 60/036,746, filed Jan. 27, 1997, and 60/019,748, filed Jun. 14, 1996.

BACKGROUND

1. Field of the Invention

The invention is generally related to the fields of pharmacology and immunology. More specifically, the invention is directed to novel compositions of matter for selectively activating T cells, and having reduced activation of Endothelial cells or fibroblasts. The novel compositions include variants of the cytokine family, and in particular human Interleukin-4 (IL-4).

2. Description of Related Art

Interleukin 4 (IL-4) is a pleiotropic cytokine, having activities on cells of the immune system, endothelium, and those of fibroblastic nature. Reported in vitro effects of IL-4 administration include proliferation of B cells, immunoglobulin class switching in B cells. In T cells, IL-4 stimulates T cell proliferation after preactivation with mitogens and down-regulates IFN-γ production. In monocytes, IL-4 induces class II MHC molecules expression, release of lipopolysaccharide-induced tPA, and CD23 expression. In Endothelial cells (EC), IL4 induces expression of VCAM-1 and IL-6 release, and decreases ICAM-1 expression (Maher, D W, et al., Human Interleukin-4: An Immunomodulator with Potential Therapeutic Applications, *Progress in Growth Factor Research*, 3:43–56 (1991)).

Because of its ability to stimulate proliferation of T cells activated by exposure to IL-2, IL-4 therapy has been pursued. For instance, IL-4 has demonstrated anti-neoplastic activity in animal models of renal carcinomas, and has induced tumor regression in mice (Bosco, M., et al., Low Doses of IL-4 Injected Perilymphatically in Tumor-bearing Mice Inhibit the Growth of Poorly and Apparently Nonimmunogenic Tumors and Induce a Tumor Specific Immune Memory, *J. Immunol.*, 145:3136–43 (1990)). However, its toxicity limits dosage in humans (Margolih, K., et al., Phase II Studies of Human Recombinant Interleukin-4 in Advanced Renal Cancer and Malignant Melanoma, *J. Immunotherapy*, 15:147–153 (1994)).

Because of its immunoregulatory activity, a number of clinical applications are suggested for IL-4. Among these clinical applications are disorders caused by imbalances of the immune system, particularly those caused by imbalances of T helper (Th) cell responses to antigen. These diseases include certain autoimmune diseases, rheumatic diseases, dermatological diseases, and infectious diseases. A large body of experimental work has established that Th cells fall into two broad classes, designated Th1 and Th2 (Mosmann, T. R., Cherwinski, H., Bond, M. W., Giedlin, M. A. and Coffinan, R. L., Two types of murine helper T cell clone. I. Definition according to profiles of lymphokine activities and secreted proteins, *J. Immunol.*, 136:2348–2357(1986); Mosmann, T. R., Cytokines, differentiation and functions of subsets of CD4 and CD8 T cells, *Behring Inst. Mitt.*, 1–6 (1995)). These T cell classes are defined by the cytokines they express: Th1 cells make IL-2, INF-γ, and TNF-α, while Th2 i cells make IL-4 and IL-5. Th1 and Th2 cells are formed from naive CD4+ T cells. Differentiation into Th1 or Th2 subsets depends on the cytokine present during antigen stimulation: IFN-γ and IL-12 direct differentiation of naive cells to the Th1 phenotype, while IL-4 directs differentiation to the Th2 phenotype. While the Th1 and Th2 subsets may represent extremes along a continuum of Th cell phenotypes (for example, Th0 cells, which express low levels of both INF-γ and IL-4, have been described), this classification nevertheless is the major paradigm in the field of immunology for describing the character of the immune response.

It has been observed that certain organ-specific autoimmune diseases are associated with a predominantly Th1 T cell response against autoantigen (Liblau R S; Singer S M; McDevitt H O, Th1 and Th2 CD4$^+$ T cells in the pathogenesis of organ-specific autoimmune diseases, *Immunol. Today*, 16:34–38 (1995)). One such autoimmune disease is insulin-dependent diabetes (IDDM), a disorder characterized by T cell-mediated destruction of pancreatic β cells. Several lines of evidence suggest that Th1-type cells are primarily responsible for the pancreatic β cell destruction (reviewed in Tisch, R. et al., Review: Insulin-dependent Diabetes Mellitus, *Ceil*, 85:291–297 (1996)). Administration of IL-4 to NOD mice, which serves as an animal model of IDDM, down-regulates the Th1 cell population and significantly delays the onset of diabetes (Rapoport, et al., IL-4 Reverses T cell Proliferation Unresponsiveness and Prevents the Onset of Diabetes in NOD Mice, *J. Exp. Med.*, 178:87–99 (1993)). Another such autoimmune disease is multiple sclerosis (MS), a disease which is characterized by an autoiimune attack upon the myelin sheath surrounding nerve cells. Studies in humans with MS have demonstrated that exacerbation of MS is associated with the presence of autoantigen-specific Th1 and Th0 cells and that remission is associated with the presence of autoantigen-specific Th2 and Th0 cells (Correale, J. et al., Patterns of cytokine secretion by autoreactive proteolipid protein-specific T cell clones during the course of multiple sclerosis, *J. Immunol.*, 154:2959–2968 (1995)). Mice with experimental autoimmune encephalomyelitis (EAE), an animal model for MS, also exhibit the Th1 cell polarization (Cua, D J, Hinton, D R, and Stohlmarn S A, *J. Immunol.*, 155:4052–4059 (1995)). Indirect evidence from a study in the EAE model suggests that IL-4 plays a critical role in disease attenuation resulting from treatment with a tolerogenic peptide (Brocke, S. et al. Treatment of experimental encephalomyelitis with a peptide analogue of myelin basic protein, *Nature*, 379:343–346 (1996)).

Other autoimmune diseases such as Rheumatoid Arthritis (RA) are also targets for IL-4 based therapies. Animal models of RA have shown a disequilibrium of cell profiles tilting towards Th1 cells, and in mice that overexpress TNF-α, anti-TNF-α antibodies have demonstrated disease attenuation, suggesting that IL4 therapies that result in down-regulation of Th1 cell populations may have an anti-TNF-α effect also. (See Feldmann, M, et al., Review: Rheumatoid Arthritis, *Cell*, 85:307–310 (1996)).

Psoriasis vulgaris is a chronic dermatologic disorder characterized by infiltration of affected skin with monocytes and T cells. Several reports indicate that psoriatic skin lesional T cells and PBL are predominantly of the Th1 phenotype (Uyemura K; Yamamura M; Fivenson D F; Modlin R L; Nickoloff B J, The cytokine network in lesional and lesion-free psoriatic skin is characterized by a T-helper type 1 cell-mediated response, *J Invest Dermatol.*, 101:701–705 (1993); Schlaak J F; Buslau M; Jochum W; Hermann E; Girndt M; Gallati H; Meyer zum Buschenfelde K H; Fleischer B, T cells involved in psoriasis vulgaris belong to the Th1 subset, *J Invest Dermatol*, 102:145–149 (1994)). Furthermore, monomethylfumarate, a drug which has been reported to be of clinical benefit to patients with psoriasis, has been shown to selectively stimulate Th2 cytokine secretion from PBMC (de Jong R; Bezemer A C; Zomerdyik T P; van de Pouw-Kraan T; Ottenhoff T H, Nibbering PH, Selective stimulation of T helper 2 cytokine responses by the anti-psoriasis agent monomethylfimarate, *Eur J Immunol*, 26:2067–2074 (1996)). Therefore, IL-4 would be expected to reverse the Th polarization and be of clinical benefit in psoriasis.

Certain infectious diseases are associated with polarized Th cell responses to the infectious agent. Th2 responses have in some cases been associated with resistance to the infectious agent. An example is *Borrelia burgdorfei*, the infectious agent for Lyme disease. Humans infected with *B. burgdorferi* exhibit a predominantly Th1-like cytokine profile (Oksi J, Savolainen J; Pene J, Bousquet J; Laippala P; Viljanen M K, Decreased interleukin-4 and increased gamma interferon production by peripheral blood mononuclear cells of patients with Lyme borreliosis, *Infect. Immun.*, 64:3620–3623 (1996)). In a mouse model of *B. burgdoreri*-induced arthritis, resistance to disease is associated with IL-4 production while susceptibility is associated with INF-γ production (Matyniak J E; Reiner S L, T helper phenotype and genetic susceptibility in experimental Lyme disease, *J Exp Med*, 181(3):1251–1254 (1995); Keane-Myers A; Nickell S P, Role of IL-4 and IFN-gamma in modulation of immunity to *Borrelia burgdorferi* in mice, *J Immunol*, 155:2020–2028 (1995)). Treatment of *B. burgdorferi*-infected mice with IL-4 augments resistance to the infection (Keane-Myers A; Maliszewski C R; Finkelman F D; Nickell S P, Recombinant IL-4 treatment augments resistance to *Borrelia burgdorferi* infections in both normal susceptible and antibody-deficient susceptible mice, *J Immunol.*, 156:2488–2494(1996)).

IL-4 has been reported to have a direct effect on inhibiting the growth of lymphomas and leukemias (Akashi, K, The role of interleukin-4 in the negative regulation of leukemia cell growth, *Leuk Lymphoma*, 9:205–9 (1993)). For example, IL-4 has been reported to induce apoptosis in cells from patients with acute lymphoblastic leukemia (Manabe, A, et al., Interleukin-4 induces programmed cell death (apoptosis) in cases of high-risk acute lymphoblastic leukemia, *Blood*, 83:1731–7 (1994)), and inhibits the growth of cells from patients with non-Hodgkin's B cell lymphoma (Defrance, T, et al., Antiproliferative effects of interleuiin-4 on freshly isolated non-Hodgkin malignant B-lymphoma cells, *Blood*, 79:990–6 (1992)).

IL-4 has also been reported to exhibit activities which suggests that it would be of clinical benefit in osteoarthritis. Osteoarthritis is a disease in which the degradation of cartilage is the primary pathology (Sack, K E, Osteoarthritis, A continuing challenge, *West J Med*, 163:579–86 (1995); Oddis, C V, New perspectives on osteoarthritis, *Am J Med*, 100:10S–15S (1996)). IL-4 inhibits TNF-α and IL-1 beta production by monocytes and synoviocytes from osteoarthritic patients (Benmrups, A, Hilton, A, Meager, A and Hamilton, J A, Reduction of tumor necrosis factor alpha and interleukin-1 beta levels in human synovial tissue by interleukin-4 and glucocorticoid, *Rheumatol Int*, 12:217–20 (1993); Seitz, M, et al., Production of interleukin-1 receptor antagonist, inflammatory chemotactic proteins, and prostaglandin E by rheumatoid and osteoarthritic synoviocytes-regulation by IFN-gamma and IL-4, *J Immunol*, 152:2060–5 (1994)). Additionally, IL-4 has been reported to directly block the degradation of cartilage in ex vivo cartilage explants (Yeh, L A, Augustine, A J, Lee, P, Riviere, L R and Sheldon, A, Interleukin-4, an inhibitor of cartilage breakdown in bovine articular cartilage explants, *J Rheumatol*, 22:1740–6 (1995)). These activities suggest that IL-4 would be of clinical benefit in osteoarthritis.

However, the clinical use of IL-4 has been limited due to its acute toxicity, which is manifested as a vascular leak syndrome (Margolin, K, et al., Phase II Studies of Human Recombinant Interleukin-4 in Advanced Renal Cancer and Malignant Melanoma, *J. Immunotherapy*, 15:147–153 (1994)). There is no art in the literature which describes the mechanism of the acute toxic effect of IL-4, nor that describes analogs or mutants of IL-4 that retain immunoregulatory activities but have reduced acute toxicity.

IL-4 mutant proteins ("muteins") are known. The IL-4 mutein IL-4/Y124D is a T cell antagonist (Kruse N, Tony H P, Sebald W, Conversion of human interleukin-4 into a high affinity antagonist by a single amino acid replacement, *Embo J*, 11:3237–44 (1992)).

Therapeutic uses of IL-4 found in patents or patent applications include the following: the use of IL-4 for potentiation of anticancer effects of chemotherapeutic agents, particularly Hodgkin's Disease and non-Hodgkins Lymphoma (see WO 9607422); the use of antigenic fragments of IL-4 to generate antibodies to treat IL-4 related diseases by suppressing or imitating the binding activity of IL-4 (see WO 9524481), and to detect, measure and immunopurify IL4 (see WO 9317106); for inducing the differentiation of precursor B cells to Immunoglobulin secreting cells, the mature B cells being useful for restoring immune function in immune-compromised patients (see WO 9404658); when used in combination with IL-10, as a therapy for treatment of leukemia, lymphoma, inflammatory bowel disease and delayed type hypersensitivity (e.g. ulcerative colitis and Crohn's Disease)(see WO 9404180); treatment of HIV infection by administering IL-4 to inhibit viral replication in monocytes and macrophages, and to increase their cytotoxicity towards some tumor cells (see WO 9404179); for stimulation of skin fibroblast proliferation for treating wounds in diabetic and immuno-compromised patients (see WO 9211861); for enhancing the primary immune response when administering bacterial, toxoid, and viral vaccines, especially tetanus toxoid vaccine (see WO 9211030); for inhibition of IL-2 induced proliferation of B cell malignancies, especially chronic lymphocytic leukemia, non-Hodgkin's malignant lymphoma (see WO 9210201); use of IL-4 to treat melanomas, renal and basal cell carcinomas (see WO 9204044).

The patent literature discloses IL-4 proteins and some muteins, but none directed to an IL-4 therapy with reduced side effects. Lee et al. U.S. Pat. No. 5,017,691 ("the '691 patent") is directed to mammalian proteins and muteins of human IL-4 which disclose both B-cell growth factor activity and T cell growth factor activity. It discloses nucleic acids coding for polypeptides exhibiting IL-4 activity, as well as the polypeptides themselves and methods for their production. Muteins to the wild-type IL-4 at amino acid positions are disclosed that retain their ability to stimulate both B- and T cell proliferation in vitro. However, nothing in Lee suggests any T cell selective IL-4 muteins, anticipated activation of EC's or the endothelial cell leakiness which accompanies administration of IL-4. Thus, IL-4 itself is not enabling as a therapeutic modality because of the dose-limiting toxicity.

U.S. Pat. No. 5,013,824 describes hIL-4 peptide derivatives comprising from 6 to 40 amino acids of the native hIL-4. Also disclosed are immunogens comprising conjugates of the peptides and carriers. Carriers include erythrocytes, bacteriophages, proteins, synthetic particles or any substance capable of eliciting antibody production against the conjugated peptide. No muteins of IL-4 are disclosed.

WO96/04306-A2 discloses single-muteins that are antagonists and partial agonists of hIL-2 and hIL-13. No data regarding IL-4 is disclosed. WO95/27052 discloses splice mutants of IL-2 and IL-4 containing exons 1, 2 and 4.

There exists a need for an improved IL-4 molecule which has reduced toxicity and is more generally tolerated.

SUMMARY OF THE INVENTION

The invention is directed to human IL-4 muteins numbered in accordance with wild-type IL-4 having T cell activating activity, but having reduced endothelial cell activating activity. In particular, human IL-4 muteins wherein the surface-exposed residues of the D helix of the wild-type IL-4 are mutated whereby the resulting mutein causes T cell proliferation, and causes reduced IL-6 secretion from HUVECs, relative to wild-type IL-4. This invention realizes a less toxic IL-4 mutein that allows greater therapeutic use of this interleukin.

Further, the invention is directed to IL-4 muteins having single, double and triple mutations represented by the designators R121A, R121D, R121E, R121F, R121H, R121I, R121K, R121N, R121P, R121T, R121W; Y124A, Y124Q, Y124R, Y124S, Y124T; Y124A/S125A, T13D/R121E; and R121T/E122F/Y124Q, when numbered in accordance with wild type IL-4 (His=1). The invention also includes polynucleotides coding for the muteins of the invention, vectors containing the polynucleotides, transformed host cells, pharmaceutical compositions comprising the muteins, and therapeutic methods of treatment.

The invention is also directed to a vector comprising the polynucleotide encoding a mutein of this invention, the vector directing the expression of a human IL-4 mutein having T cell activating activity but having reduced endothelial cell activating activity, the vector being capable of enabling transfection of a target organism and subsequent in vivo expression of said human IL-4 mutein coded for by said polynucleotide.

The invention is also directed to a method of selecting a human IL-4 mutein numbered in accordance with wild-type IL-4 having T cell activating activity but having reduced endothelial cell activating activity, comprising mutating the surface-exposed residues of the D helix of the wild-type IL-4 whereby the resulting mutein causes T cell proliferation, and causes reduced IL-6 secretion from HUVECs, relative to wild-type.

The invention is also directed to a method of treating a patient afflicted with an IL-4 treatable condition by administering a therapeutically effective amount of a human IL-4 mutein numbered in accordance with wild-type IL-4 having T cell activating activity but having reduced endothelial cell activating activity. This method is applicable wherein the IL-4 treatable condition is an autoimmune disorder, cancer, infectious disease, cartilage disorder, and psoriatic disorders.

BRIEF DESCRIPTION OF THE DRAWINGS

FIG. 1 is an amino acid sequence (SEQ ID NO:1) of mature wild-type human IL-4 used in this study. Helices are underlined and labeled sequentially A, B, C, and D. Positions that, when mutated yielded cell-selective IL-4 agonists, are indicated in bold type.

FIG. 2 is a graphical presentation of the T cell selective agonist concept.

FIGS. 3A and 3B is a composite dose response curve for selective agonist muteins in the HUVEC IL-6 secretion assay. Panel A: ○, wild-type IL-4; ●, R121E; ▽, R121P; ▼, R121T/E122F/Y124Q. Panel B: ○, wild-type IL-4; ●, Y124Q; ▽, Y124R; ▼, Y124A/S125A.

FIGS. 4A–4F and are individual dose response curves of selective agonist muteins in the HUVEC IL-6 secretion assay. Panel A: ○, wild-type IL-4; ●, R121E. Panel B: ○, wild-type IL-4; ●, R121P. Panel C: ○, wild-type IL-4; ●, Y124Q. Panel D: ○, wild-type IL-4; ●, Y124R. Panel E: ○, wild-type IL-4; ●, Y124A/S125A. Panel F: ○, wild-type IL-4; ●, R121T/E122F/Y124Q.

FIGS. 5A and 5B is a composite dose-response curve for selective agonist muteins for the biological response of IL-4 muteins in 1° T cell proliferation assays. Panel A: ○, wild-type IL-4; ●, R121E; ▽, R121P; ▼, R121T/E122F/Y124Q. Panel B: ○, wild-type IL-4; ●, Y124Q; ▽, Y124R; ▼, Y124A/S125A.

FIGS. 6A–6F are individual dose response curves of the 1° T cell proliferation assay. Panel A: ○, wild-type L-4; ●, R121E. Panel B: ○, wild-type IL-4; ●, R121P. Panel C: ○, wild-type IL-4; ●, Y124Q. Panel D: ○, wild-type IL-4; ●, Y124R. Panel E: ○, wild-type IL-4; ●, Y124A/S125A. Panel F: ○, wild-type IL-4; ●, R121T/E122F/Y124Q.

FIG. 7 are individual dose response curves showing the antagonism of IL-4-induced IL-6 secretion on HUVEC by the T cell-selective agonist IL-4 muteins R121E (●) and Y124Q (▽). The dose response of the IL-4 antagonist R121D/Y124D (○) is included as a control.

FIGS. 8A and 8B are individual dose response curves: Panel A shows the biological response of the R121D mutein in a 1° T cell proliferation assay (○=IL-4,●=R121D); Panel B shows the inability of R121D to induce IL-6 secretion on HUVEC (○=IL4, ●=R121D).

FIG. 9A are the individual dose response curves for IL-4 (○) and the T cell-selective agonist muteins R121E (Δ) and T13D/R121E (▲) in the 1° T cell proliferation assay.

FIG. 9B are individual dose response curves showing the antagonism of IL-4-induced IL-6 secretion on HUVEC by the T cell-selective IL-4 agonist muteins R121E (Δ) and T13D/R121E (▲).

FIG. 9C is an individual dose response curve showing % maximum cytokine release versus concentration. In the HUVEC assay shown, T13D/R121E (▲) exhibited nominal activity comparable to that seen with R121E (Δ). In this assay, measurement of monocyte chemoattractant protein 1 (MCP-1) in the media by ELISA was used instead of IL-6 to measure activity.

FIGS. 10A through 10D are graphs that show the change in Day 1 levels of fibrinogen and APTT as a function of exposure to test article.

FIGS. 11A–B are graphs of percentages of CD23+ and CD4+IL-4R+ over CD4+ lymphocytes in the peripheral blood during Phase II of the safety pharmacology study. Each point plotted corresponds to the average±s.d. of observations from 2 animals.

FIGS. 12A–12C are charts showing FACS analysis for CD4+, showing lymphocytes in the circulation, Phase I (FIG. 12A), Phase II (FIG. 12B). FIG. 12C is a histogram of the effects of vehicle, 10 and 30 $\mu$g/kg wild-type IL-4, and 10, 30, 100 and 300 $\mu$g/kg IL-4[T13D/R121E].

DESCRIPTION OF THE PREFERRED EMBODIMENTS

A. Background

IL-4 has been shown to mediate a variety of cellular responses in vitro, including various effects on B cells, T cells, and monocytes, as well as endothelial cells (Maher D W, Davis I, Boyd A W, Morstyn G: Human interleulin-4: an immunomodulator with potential therapeutic applications. *Prog Growth Factor Res* 3:43–56, 1991; Powrie F, Coffman R L: Cytokine regulation of T cell function: potential for therapeutic intervention. *Immunol Today* 14:2704, 1993). In particular, upregulation of vascular cell adhesion molecule-1 (VCAM-1; (Swerlick R A, Lee K H, Li L J, Sepp N T, Caughman S W, Lawley T J: Regulation of vascular cell adhesion molecule 1 on human dermal micro vascular endothelial cells. *J Immunol* 149:698–705, 1992)) and induction of IL-6 (Colotta F, Sironi M, Borre A, Luini W, Maddalena F, Mantovani A: Interleukin 4 amplifies monocyte chemotactic protein and interleukin 6 production by endothelial cells. *Cytokine* 4:24–8, 1992) and monocyte chemoattractant protein-1 (MCP-1; Colotta F, Sironi M, Borre A, Luini W, Maddalena F, Mantovani A: Interleukin 4 amplifies monocyte chemotactic protein and interleukin 6 production by endothelial cells. *Cytokine* 4:24–8, 1992; Rollins B J, Pober J S: Interleukin-4 induces the synthesis and secretion of MCP-1/JE by human endothelial cells. *Am J Pathol* 138:1315–9, 1991)) are direct effects of IL-4 on cultured endothelial cells; the upregulation of VCAM-1 is correlated with the increased adhesion of lymphocytes both in vitro (Carlos T M, Schwartz B R, Kovach N L, Yee E, Rosa M, Osborn L, Chi-Rosso G, Newman B, Lobb R, Rosso M, et al.: Vascular cell adhesion molecule-1 mediates lymphocyte adherence to cytokine-activated cultured human endothelial cells. *Blood* 76:965–70, 1990; Thornhill M H, Wellicome S M, Mahiouz D L, Lanchbury J S, Kyan-Aung U, Haskard D O: Tumor necrosis factor combines with IL-4 or IFN-gamma to selectively enhance endothelial cell adhesiveness for T cells. The contribution of vascular cell adhesion molecule-1-dependent and -independent binding mechanisms. *J Immunol* 146:592–8, 1991) and in vivo (Briscoe D M, Cotran R S, Pober J S: Effects of tumor necrosis factor, lipopolysaccharide, and IL-4 on the expression of vascular cell adhesion molecule-1 in vivo. Correlation with CD3+ T cell infiltration. *J Immunol* 149:2954–60, 1992).

The IL-4 mutein IL-4/Y124D (substitution of Aspartic acid for Tyrosine at position 124) is a T cell antagonist (Kruse N, Tony H P, Sebald W: Conversion of human interleukin-4 into a high affinity antagonist by a single amino acid replacement. *Embo J* 11:3237–44, 1992). In vivo experiments performed by the inventors have demonstrated that IL-4/Y124D exhibits acute toxicity similar to that of wild-type IL-4 in monkeys, a previously undescribed observation. The cellular events associated with both wild-type IL-4- and IL-4/Y124D-mediated toxicity include upregulation of VCAM-1, upregulation of MCP-1 in serum, increases in circulating monocytes together with a concomitant decrease in circulating lymphocytes, and an increase in hematocrit. Similar cellular trafficking has been observed in clinical trials using IL-4 in humans (Wong H L, Lotze M T, Wahl L M, Wahl S M: Administration of recombinant IL-4 to humans regulates gene expression, phenotype, and function in circulating monocytes. *J Immunol* 148:2118–25, 1992). Due to its properties as an antagonist of T cells, these results suggest that the toxicities demonstrated by IL-4/Y124D are due to agonist activities on and are mediated through cells other than T cells. The observed in vivo toxicities using IL-4/Y124D and the known effects of IL-4 on endothelial cells are consistent with the mechanism that in vivo IL-4 toxicity is mediated through direct effects of IL-4 on the vascular endothelium.

Through these (and related) investigations, the inventors have discovered that a new IL-4 receptor may exist on endothelial cells ("EC"). This possibility led to efforts to synthesize IL-4 muteins that would selectively activate T cells, but not EC. While T cells express an IL-4 receptor composed of IL-4Rα and IL-2Rγ sub units, the inventors have discovered that human umbilical vein endothelial cells (HUVEC), express IL-4Rα but not IL-2Rγ. Crosslinking studies have shown that two receptor chains are expressed at the cell surface of HUVEC: the molecular weight of one is consistent with IL-4Rα, and a second, lower molecular weight chain. These results suggest that a novel IL-4 receptor component similar in function to IL-2Rγ, but differing in sequence, is expressed on HUVECs. The differences in the specific molecular structures between these two receptors were thus exploited to generate an IL-4 variant that is selective for one receptor over the other (e.g., a T cell selective agonist).

FIG. 2 demonstrates graphically the selective agonist concept. It shows the T cell IL-4 receptor comprising the IL-4Rα/IL-2Rγ sub unit, and an Endothelial cell IL-4 receptor comprising the IL-4Rα/γ-like receptor subunit. Although depicted here together for purposes of illustration only, the two receptors for IL-4 are expressed on different cell types. The T cell receptor is composed of IL-4Rα and IL-2Rγ; IL-4 binding induces receptor heterodimer formation that results in cellular signalling. IL-4 induced receptor heterodimer formation occurs in a similar manner on EC's, except that the receptor for IL-4 is composed of IL-4Rα and a γ-like receptor component The γ-like receptor component is different from IL-2Rγ. T cell-selective IL-4 agonists are those variants of IL-4 that retain their ability to interact with the T cell receptor IL-4Rα/IL-2Rγ, but are unable to induce heterodimerization, and thus signalling, of the non-T cell receptor IL-4Rα/γ-like sub unit. Such T cell-selective IL-4 agonists retain their ability to interact with IL-4Rα; it is their ability to discriminate between IL-2Rγ and the γ-like sub unit that gives them their cell-selective activation properties.

The two components of the T cell receptor, IL-4-Rα and IL-2Rγ, contact different regions of the IL-4 molecule, and therefor the inventors have focussed on a small region of IL-4 to modify. Hypothesizing that the novel receptor sub unit would contact the same region of IL4 as does IL-2Rγ, the inventors made a number of substitutions in the D-Helix, particularly residues 121, 124 and 125.

The D-helix has been implicated in interactions with both IL-2Rγ and with the putative novel receptor on HUVEC (specifically, the IL-4 mutein R121D/Y124D is a HUVEC antagonist). Muteins containing modifications to the D-helix of IL-4 (residues 110 to 126; His=1) were screened for their ability to stimulate either T cell proliferation or human umbilical vein endothelial cell (HUVEC) secretion of IL-6. Muteins that induced a differential response on T cells relative to HUVEC were further characterized through further mutagenesis.

An initial scan of the D helix was undertaken to determine the potential areas of interaction. Additionally, alanine scanning substitutions of the AB loop were also generated, as this region is suggested to be involved in the interaction of the cytokine ligand and the D-helix interacting receptor sub unit. In particular, surface-exposed residues Glu-110, Asn- 111, Glu-114, Arg-115, Lys-117, Thr-118, Arg-121, Glu-122, Tyr-124, Ser-125, and Lys-126 were targeted for investigation and are preferred targets for mutation analysis. Sites 118–126 are more preferred, and sites 121–125 are most preferred. Comparisons between IL-2, IL-4, IL-7 and IL-15 in this region also identify differences between IL-4 and IL-2, IL-7 and IL-15, possibly suggesting specific residues responsible for the HUVEC receptor interaction. Specific substitutions derived from an alignment between IL-2 and IL-4 were introduced into IL-4. These included: Arg-115 to Phe; Lys-117 to Asn; Glu-122 to Phe; Lys-126 to Ile; and three simultaneous changes Arg-121 to Thr, Glu-122 to Phe, and Tyr-124 to Gln.

Mutations were introduced using site-directed mutagenesis on wild-type human IL-4 cDNA. Correct clones were subcloned to an expression vector suitable for expression in a heterologous system (e.g., *E. coli*, baculovirus, or CHO cells). Purified proteins were tested in T cell proliferation and HUVEC cytokine secretion assays (IL-6). Different responses generated by individual muteins between these assays, either in $EC_{50}$ or maximal response (plateau) indicate mutations that effect these activities. Specifically, muteins that stimulate a relatively stronger response in the T cell assay (vs. wild-type IL-4) as compared to the response on HUVEC (vs. wild-type IL-4) will suggest positions that are more important to the interaction of IL-4 with IL-2Rγ than the interaction of IL-4 with the novel HUVEC IL-4 receptor. Further analysis and mutagenesis (e.g. combinatorial changes, substitution with all amino acids) of the identified positions will produce an IL-4 mutein with selective agonist properties for the T cell IL-4 receptor. This protein will also be a selective antagonist for IL-4-induced HUVEC responses.

B. Definitions

Described herein are novel muteins and a mechanism for deriving novel IL-4 muteins with selective agonist properties on T cells and reduced toxicity. A similar strategy may be used to identify a T cell-selective antagonist.

As used herein, "wild type IL-4" means IL-4, whether native or recombinant, having the 129 normally occurring amino acid sequence of native human IL-4, as shown, e.g., in FIG. 1.

As used herein, "IL-4 mutein" means a polypeptide wherein specific substitutions to the human mature interleuldin-4 protein have been made. Specifically disclosed herein, the arginine residue (R) at position 121 ("Arg-121"), when numbered in accordance with wild type IL-4, is substituted with alanine (A), aspartate (D), glutamate (E), phenylalanine (F), histidine (H), isoleucine (I), lysine (K), asparagine (N) proline (P), threonine (T) or tryptophan (W); or the glutamate (E) residue at position 122 is substituted with phenylalanine (F); or the tyrosine residue at position 124 is substituted with alanine (A), glutamine (Q), arginine (R) serine (S) or threonine (T); or the serine (S) residue at position 125 is substituted with alanine (A). Our most preferred IL-4 muteins have an amino acid sequence identical to wild type IL-4 at the other, non-substituted residues. However, the IL-4 muteins of this invention may also be characterized by amino acid insertions, deletions, substitutions and modifications at one or more sites in or at the other residues of the native IL-4 polypeptide chain. In accordance with this invention any such insertions, deletions, substitutions and modifications result in an IL-4 mutein that retains a T cell-selective activity while having reduced ability to activate endothelial cells.

We prefer conservative modifications and substitutions at other positions of IL-4 (i.e., those that have a minimal effect on the secondary or tertiary structure of the mutein). Such conservative substitutions include those described by Dayhoff in *The Atlas of Protein Sequence and Structure* 5 (1978), and by Argos in *EMBO J.*, 8:779–785 (1989). For example, amino acids belonging to one of the following groups represent conservative changes:

ala, pro, gly, gin, asn, ser, thr;

cys, ser, tyr, thr;

val, ile, leu, met, ala, phe;

lys, arg, his;

phe, tyr, trp, his; and asp, glu.

We also prefer modifications or substitutions that do not introduce sites for additional intermolecular crosslinking or incorrect disulfide bond formation. For example, IL-4 is known to have six cys residues, at wild-type positions 3, 24, 46, 65, 99 and 127.

By "numbered in accordance with wild type IL-4" we mean identifying a chosen amino acid with reference to the position at which that amino acid normally occurs in wild type IL-4. Where insertions or deletions are made to the IL-4 mutein, one of skill in the art will appreciate that the ser (S) normally occurring at position 125, when numbered in accordance with wild type IL-4, may be shifted in position in the mutein. However, the location of the shifted ser (S) can be readily determined by inspection and correlation of the flanking amino acids with those flanking ser in wild type IL-4.

The IL-4 muteins of the present invention can be produced by any suitable method known in the art. Such methods include constructing a DNA sequence encoding the IL-4 muteins of this invention and expressing those sequences in a suitably transformed host. This method will produce recombinant muteins of this invention. However, the muteins of this invention may also be produced, albeit less preferably, by chemical synthesis or a combination of chemical synthesis and recombinant DNA technology.

In one embodiment of a recombinant method for producing a mutein of this invention, a DNA sequence is constructed by isolating or synthesizing a DNA sequence encoding the wild type IL-4 and then changing the codon for arg121 to a codon for alanine (A), aspartate (D), glutamate (E), phenylalanine (F), histidine (H), isoleucine (I), lysine (K), asparagine (N) proline (P), threonine (T) or tryptophan (W) by site-specific mutagenesis. This technique is well known. See, e.g., Mark et al., "Site-specific Mutagenesis Of The Human Fibroblast Interferon Gene", *Proc. Natl. Acad. Sci. USA* 81, pp. 5662–66 (1984); U.S. Pat. No. 4,588,585, incorporated herein by reference.

Another method of constructing a DNA sequence encoding the IL-4 muteins of this invention would be chemical synthesis. For example, a gene which encodes the desired IL-4 mutein may be synthesized by chemical means using an oligonucleotide synthesizer. Such oligonucleotides are designed based on the amino acid sequence of the desired IL-4 mutein, and preferably selecting those codons that are favored in the host cell in which the recombinant mutein will be produced. In this regard, it is well recognized that the genetic code is degenerate—that an amino acid may be coded for by more than one codon. For example, phe (F) is coded for by two codons, TTC or TTT, tyr (Y) is coded for by TAC or TAT and his (H) is coded for by CAC or CAT. Trp (W) is coded for by a single codon, TGG. Accordingly, it will be appreciated that for a given DNA sequence encoding a particular IL-4 mutein, there will be many DNA degenerate sequences that will code for that IL-4 mutein. For example, it will be appreciated that in addition to the preferred DNA sequence for mutein R121E shown in SEQ ID NO:3, there will be many degenerate DNA sequences that code for the IL-4 mutein shown. These degenerate DNA sequences are considered within the scope of this invention. Therefore, "degenerate variants thereof" in the context of this invention means all DNA sequences that code for a particular mutein.

The DNA sequence encoding the IL-4 mutein of this invention, whether prepared by site directed mutagenesis, synthesis or other methods, may or may not also include DNA sequences that encode a signal sequence. Such signal sequence, if present, should be one recognized by the cell chosen for expression of the IL-4 mutein. It may be prokaryotic, eukaryotic or a combination of the two. It may also be the signal sequence of native IL-4. The inclusion of a signal sequence depends on whether it is desired to secrete the IL-4 mutein from the recombinant cells in which it is made. If the chosen cells are prokaryotic, it generally is preferred that the DNA sequence not encode a signal sequence. If the chosen cells are eukaryotic, it generally is preferred that a signal sequence be encoded and most preferably that the wild-type IL-4 signal sequence be used.

Standard methods may be applied to synthesize a gene encoding an IL-4 mutein according to this invention. For example, the complete amino acid sequence may be used to construct a back-translated gene. A DNA oligomer containing a nucleotide sequence coding for IL-4 mutein may be synthesized. For example, several small oligonucleotides coding for portions of the desired polypeptide may be synthesized and then ligated. The individual oligonucleotides typically contain 5' or 3' overhangs for complementary assembly.

Once assembled (by synthesis, siteairected mutagenesis or another method), the DNA sequences encoding an IL-4 mutein of this invention will be inserted into an expression vector and operatively linked to an expression control sequence appropriate for expression of the IL-4 mutein in the desired transformed host. Proper assembly may be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

The choice of expression control sequence and expression vector will depend upon the choice of host. A wide variety of expression host/vector combinations may be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *E.coli*, including col E1, pCR1, pER32z, pMB9 and their derivatives, wider host range plasmids, such as RP4, phage DNAs, e.g., the numerous derivatives of phage lambda, e.g., NM989, and other DNA phages, such as M13 and filamentous single stranded DNA phages. Useful expression vectors for yeast cells include the $2\mu$ plasmid and derivatives thereof. Useful vectors for insect cells include pVL 941. We prefer pFastBac™ 1 (GibcoBRL, Gaithersburg, Md.). Cate et al., "Isolation Of The Bovine And Human Genes For Mullerian Inhibiting Substance And Expression Of The Human Gene In Animal Cells", Cell, 45, pp. 685–98 (1986).

In addition, any of a wide variety of expression control sequences may be used in these vectors. Such useful expression control sequences include the expression control sequences associated with structurl genes of the foregoing expression vectors. Examples of useful expression control sequences include, for example, the early and late promoters of SV40 or adenovirus, the lac system, the trp system, the TAC or IRC system, the major operator and promoter regions of phage lambda, for example PL, the control regions of fd coat protein, the promoter for 3-phosphoglycerate kinase or other glycolytic enzymes, the promoters of acid phosphatase, e.g., PhoA, the promoters of the yeast α-mating system, the polyhedron promotor of Baculovims, and other sequences known to control the expression of genes of prokaryotic or eukaryotic cells or their viruses, and various combinations thereof Any suitable host may be used to produce the IL-4 muteins of this invention, including bacteria, fungi (including yeasts), plant, insect, mammal, or other appropriate animal cells or cell lines, as well as transgenic animals or plants. More particularly, these hosts may include well known eukaryotic and prokaryotic hosts, such as strains of *E.coli*, Pseudomonas, Bacillus, Streptomyces, fungi, yeast, insect cells such as *Spodoptera frugiperda* (*Sf*9), animal cells such as Chinese hamster ovary (CHO) and mouse cells such as NS/O, African green monkey cells such as COS 1, COS 7, BSC 1, BSC 40, and BNT 10, and human cells, as well as plant cells in tissue culture. For animal cell expression, we prefer CHO cells and COS 7 cells in cultures and particularly the CHO cell line CHO (D HFR−).

It should of course be understood that not all vectors and expression control sequences will function equally well to express the DNA sequences described herein. Neither will all hosts function equally well with the same expression system. However, one of skill in the art may make a selection among these vectors, expression control sequences and hosts without undue experimentation. For example, in selecting a vector, the host must be considered because the vector must replicate in it. The vector's copy number, the ability to control that copy number, and the expression of any other proteins encoded by the vector, such as antibiotic markers, should also be considered. For example, preferred vectors for use in this invention include those that allow the DNA encoding the IL-4 muteins to be amplified in copy number. Such amplifiable vectors are well known in the art. They include, for example, vectors able to be amplified by DHFR amplification (see, e.g., Kaufman, U.S. Pat. No. 4,470,461, Kaufman and Sharp, "Construction Of A Modular Dihydrafolate Reductase cDNA Gene: Analysis Of Signals Utilized For Efficient Expression", Mol. Cell. Biol., 2, pp. 1304–19 (1982)) or glutamine synthetase ("GS") amplification (see, e.g., U.S. Pat. No. 5,122,464 and European published application 338,841).

In selecting an expression control sequence, a variety of factors should also be considered. These include, for example, the relative strength of the sequence, its controllability, and its compatibility with the actual DNA sequence encoding the IL-4 mutein of this invention, particularly as regards potential secondary structures. Hosts should be selected by consideration of their compatibility with the chosen vector, the toxicity of the product coded for by the DNA sequences of this invention, their secretion characteristics, their ability to fold the polypeptides correctly, their fermentation or culture requirements, and the ease of purification of the products coded for by the DNA sequences.

Within these parameters, one of skill in the art may select various vector/expression control sequence/host combinations that will express the desired DNA sequences on fermentation or in large scale animal culture, for example, using CHO cells or COS 7 cells.

The IL-4 muteins obtained according to the present invention may be glycosylated or unglycosylated depending on the host organism used to produce the mutein. If bacteria are chosen as the host then the IL-4 mutein produced will be unglycosylated. Eukaryotic cells, on the other hand, will glycosylate the IL-4 muteins, although perhaps not in the same way as native IL-4 is glycosylated.

The IL-4 mutein produced by the transformed host can be purified according to any suitable method. Various methods are known for purifying IL-4. See, e.g., U.S. Pat. Nos. 5,013,824; 5,017,691; and WO9604306-A2. We prefer immunoaffinity purification. See, e.g., Okamura et al., "Human Fibroblastoid Interferon: Immunosorbent Column Chromatography And N-Terminal Amino Acid Sequence", *Biochem.*, 19, pp. 3831–35 (1980).

The biological activity of the IL-4 muteins of this invention can be assayed by any suitable method known in the art Such assays include antibody neutralization of antiviral activity, induction of protein kinase, oligoadenylate 2,5-A synthetase or phosphodiesterase activities, as described in EP-B1-41313. Such assays also include immunomodulatory assays (see, e.g., U.S. Pat. No. 4,753,795), growth inhibition assays, T cell proliferation, induction of IL-6 (MCP-1 or VCAM-1) on EC and measurement of binding to cells that express interleukin-4 receptors. See also Spits H, Yssel H. Takebe Y. et al., Recombinant Interleukin-4 Promotes the Growth of Human T Cells, *J. IMMUNOL* 139:1142–47 (1987).

The IL-4 mutein of this invention will be administered at a dose approximately paralleling that or greater than employed in therapy with wild type native or recombinant IL-4. An effective amount of the IL-4 mutein is preferably administered. An "effective amount" means an amount capable of preventing or lessening the severity or spread of the condition or indication being treated. It will be apparent to those of skill in the art that the effective amount of IL-4 mutein will depend, inter alia, upon the disease, the dose, the administration schedule of the IL-4 mutein, whether the IL-4 mutein is administered alone or in conjunction with other therapeutic agents, the serun half-life of the composition, and the general health of the patient.

The IL-4 mutein is preferably administered in a composition including a pharmaceutically acceptable carrier. "Pharmaceutically acceptable carrier" means a carrier that does not cause any untoward effect in patients to whom it is administered. Such pharmaceutically acceptable carriers are well known in the art. We prefer 2% HSA/PBS at pH 7.0.

The IL-4 muteins of the present invention can be formulated into pharmaceutical compositions by well known methods. See, e.g., Remington's Pharmacautical Science by E. W. Martin, hereby incorporated by reference, describes suitable formulations. The pharmaceutical composition of the IL-4 mutein may be formulated in a variety of forms, including liquid, gel, lyophilized, or any other suitable form. The preferred form will depend upon the particular indication being treated and will be apparent to one of skill in the art.

The IL-4 mutein pharmaceutical composition may be administered orally, by aerosol, intravenously, intramuscularly, intraperitoneally, intradermally or subcutaneously or in any other acceptable manner. The preferred mode of administration will depend upon the particular indication being treated and will be apparent to one of skill in the art. The pharmaceutical composition of the IL-4 mutein may be administered in conjunction with other therapeutic agents. These agents may be incorporated as part of the same pharmaceutical composition or may be administered separately from the IL-4 mutein, either concurrently or in accordance with any other acceptable treatment schedule. In addition, the IL-4 mutein pharmaceutical composition may be used as an adjunct to other therapies.

Accordingly, this invention provides compositions and methods for treating immune disorders, cancers or tumors, abnormal cell growth, or for immunomodulation in any suitable animal, preferably a mammal, most preferably human. As previously noted in the Background section, IL-4 has many effects. Some of these are stimulation of T cell proliferation, T-helper cell differentiation, induction of human B-cell activation and proliferation, and lymphokine-directed immunoglobulin class switching. Effects on the lymphoid system include increasing the expression of MHC class II antigen (Noelle, R., et al., Increased Expression of Ia Antigens on resting B cells: a New Role for B Cell Growth Factor, *PNAS USA*, 81:6149–53 (1984)), and CD 23 on B cells (Kikutani, H., et al., Molecular Structure of Human Lymphocyte Receptor for Immunoglobulin, *Cell* 47:65761 (1986)). T-helper cell type 1 (Th1) and type 2 (Th2) are involved in the immune response. Stimulated Th2 cells secrete IL-4 and block Th1 progression. Thus, any Th1-implicated disease is amenable to treatment by IL-4 or analogs thereof.

Also contemplated is use of the DNA sequences encoding the IL-4 muteins of this invention in gene therapy applications. Gene therapy applications contemplated include treatment of those diseases in which IL-4 is expected to provide an effective therapy due to its immunomodulatory activity, e.g., Multiple Sclerosis (MS), Insulin-dependent Diabetes Mellitus (IDDM), Rheumatoid Arthritis (RA), Systemic Lupus Erythematosus (SLE), uveitis, orchitis, primary biliary cirrhosis, malaria, leprosy, Lyme Disease, contact dermatitis, psoriasis, B cell lymphoma, acute lymphoblastic leukemia, non-Hodgkins lymphoma, cancer, osteoarthritis and diseases that are otherwise responsive to IL-4 or infectious agents sensitive to IL-4-mediated immune response.

Local delivery of IL-4 muteins using gene therapy may provide the therapeutic agent to the target area. Both in vitro and in vivo gene therapy methodologies are contemplated. Several methods for transferring potentially therapeutic genes to defined cell populations are known. See, e.g., Mulligan, "The Basic Science Of Gene Therapy", *Science*, 260: 926–31 (1993). These methods include:

1) Direct gene transfer. See, e.g., Wolff et al, "Direct Gene transfer Into Mouse Muscle In Vivo", *Science*. 247:1465–68 (1990);

2) Liposome-mediated DNA transfer. See, e.g., Caplen at al., "Liposome-mediated CFTR Gene Transfer To The Nasal Epithelium Of Patients With Cystic Fibrosis", *Nature Med.* 3: 39–46 (1995); Crystal, "The Gene As A Drug", *Nature Med.* 1:15–17 (1995); Gao and Huang, "A Novel Cationic Liposome Reagenit For Efficient Transfection Of Mammalian Cells", *Biochem. Biophys. Res. Comm.*, 179:280–85 (1991);

3) Retrovirus-mediated DNA transfer. See, e.g., Kay et al., "In Vivo Gene Therapy Of Hemophilia B: Sustained Partial Correction In Factor IX-Deficient Dogs", *Science*, 262:117–19 (1993); Anderson, "Human Gene Therapy", *Science* 256:808–13 (1992).

4) DNA Virus-mediated DNA transfer. Such DNA viruses include adenoviruses (preferably Ad-2 or Ad-5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., Ali et al., "The Use Of DNA Viruses As Vectors For Gene Therapy", *Gene Therapy*, 1:367–84 (1994); U.S. Pat. No. 4,797,368, incorporated herein by reference, and U.S. Pat. No. 5,139,941, incorporated herein by reference.

The choice of a particular vector system for transferring the gene of interest will depend on a variety of factors. One important factor is the nature of the target cell population. Although retroviral vectors have been extensively studied and used in a number of gene therapy applications, these vectors are generally unsuited for infecting non-dividing cells. In addition, retroviruses have the potential for oncogenicity.

Adenoviruses have the advantage that they have a broad host range, can infect quiescent or terminally differentiated cells, such as neurons or hepatocytes, and appear essentially non-oncogenic. See, e.g., Ali et al., supra, p. 367. Adenoviruses do not appear to integrate into the host genome. Because they exist extrachromosomally, the risk of insertional mutagenesis is greatly reduced. Ali et al., supra, p. 373.

Adeno-associated viruses exhibit similar advantages as adenoviral-based vectors. However, AAVs exhibit site-specific integration on human chromosome 19. Ali et aL, supra, p.377.

In a preferred embodiment, the IL-4 mutein-encoding DNA of this invention is used in gene therapy for autoimmune diseases such as MS, IDDM, and RA, infectious diseases such as Lyme Disease and Leprosy, cancers, such as non-Hodgkins lymphoma and ALL, cartiledgenous disorders such as osteoarthritis, and psoriatic conditions, such as psoriasis.

According to this embodiment, gene therapy with DNA encoding the IL-4 muteins of this invention is provided to a patient in need thereof, concurrent with, or immediately after diagnosis.

This approach takes advantage of the selective activity of the IL-4 muteins of this invention to prevent undesired autoimmune stimulation. The skilled artisan will appreciate that any suitable gene therapy vector containing IL-4 mutein DNA may be used in accordance with this embodiment. The techniques for constructing such a vector are known. See, e.g., Ohno et al., supra, p. 784; Chang et al., supra, p. 522. Introduction of the IL-4 mutein DNA-containing vector to the target site may be accomplished using known techniques, e.g., as described in Ohno et al., supra, p. 784.

In order that this invention may be better understood, the following examples are set forth. These examples are for the purpose of illustration only, and are not to be construed as limiting the scope of the invention in any manner.

EXAMPLES

Generally

The amino acid sequence of mature human IL-4 used in this study is shown below. Amino acids at which substitutions yielded T cell selective agonists are indicated in bold type:

```
His Lys Cys Asp Ile Thr Leu Gln Glu Ile Ile Lys Thr Leu Asn (SEQ ID NO:1)
1               5                   10                  15

Ser Leu Thr Glu Gln Lys Thr Leu Cys Thr Glu Leu Thr Val Thr
                20                  25                  30

Asp Ile Phe Ala Ala Ser Lys Asn Thr Thr Glu Lys Glu Thr Phe
                35                  40                  45

Cys Arg Ala Ala Thr Val Leu Arg Gln Phe Tyr Ser His His Glu
                50                  55                  60

Lys Asp Thr Arg Cys Leu Gly Ala Thr Ala Gln Gln Phe His Arg
                65                  70                  75

His Lys Gln Leu Ile Arg Phe Leu Lys Arg Leu Asp Arg Asn Leu
                80                  85                  90

Trp Gly Leu Ala Gly Leu Asn Ser Cys Pro Val Lys Glu Ala Asn
                95                  100                 105

Gln Ser Thr Leu Glu Asn Phe Leu Glu Arg Leu Lys Thr Ile Met
                110                 115                 120

Arg Clu Lys Tyr Ser Lys Cys Ser Ser
                125
```

Muteins were expressed in a baculovirus system, purified to homogeneity, and evaluated in biological assays that reflected different IL-4 receptor usage. Two assays were used to test for selective agonist activity, IL-4induced HUVEC IL-6 secretion assay, and 1° T cell proliferation assay for positive IL-4 activity. Compounds that have the ability to induce 1° T cell proliferation, yet have a reduced ability to induce IL-6 secretion, are T cell selective IL-4 agonists and come within the scope of this invention. More specifically, human umbilical vein endothelial cells (HUVEC) were used to assess activity through the alternate IL-4 receptor (IL-4Rα/γ-like receptor component).

Example 1

Production of Muteins

Muteins were generated by site-directed mutagenesis using primers containing codons corresponding to the desired mutation essentially as described by Kunkel T A, Roberts J D, and Zakour R A, "Rapid and efficient site-specific mutagenesis without phenotypic selection" (1987),

*Methods Enzymol* 154: 367–382. Briefly, human IL-4 cDNA containing the restriction enzyme sites Bam HI and Xba I was subcloned into the M13 phage vector M13 mp19 (New England Biolabs, Beverly, Mass.) using the same sites. Wild-type IL-4 cDNA was obtained using Polymerase Chain Reaction ("PCR") from a cDNA pool generated from mRNA isolated from human peripheral blood lymphocytes induced 24 hours with phorbol 12-myristate 13-acetate (10 ng/ml). The PCR primers used were, for the 5' end of the IL-4 open reading frame,

5'-CGC GGA TCC ATG GGT CTC ACC TCC-3' (SEQ ID NO:22);

and for the 3' end of the IL-4 open reading frame,

5'-CGC TCT AGA CTA GCT CGA ACA CTT TGA AT-3' (SEQ ID NO:23).

Restriction enzyme sites BamHI (5'-end) and XbaI (3'-end) were incorporated into each oligonucleotide and are indicated by italics. The PCR conditions used were 1 minute at 94° C., 1 minute at 58.7° C., and 1 minute at 72° C. for 25 cycles. The correct IL-4 cDNA sequence so obtained was confirmed by sequencing using the Sequenase® sequencing kit (Amersham Life Sciences, Arlington Heights, Ill.) as described by the manufacturer. Uracil-containing single strand DNA (U-DNA) was obtained by transforming the *E. coli* strain CJ236 (Bio-Rad Laboratories, Hercules, Calif.) with IL-4 cDNA-containing M13 mp19. Site-directed mutagenesis utilized in general primers containing 15 nucleotides homologous to the template U-DNA 5' to the codon(s) targeted for mutagenesis, nucleotides that incorporate the desired change, and an additional 10 nucleotides homologous to the template U-DNA 3' of the last altered nucleotide. The specific primers used were:

Regions of mutated nucleotides are underlined. Primers were phosphorylated using T4 polynucleotide kinase (New England Biolabs, Beverly, Mass.) using the manufacturer's protocol. After annealing of the primer to the U-DNA template and extension with T7 DNA polymerase (Bio-Rad Laboratories, Hercules, Calif.), cells of the *E. coli* strain DH5α™ (GibcoBRL, Gaithersburg, Md.) were transformed with 5 μl of reaction mixture and plated in LB medium containing 0.7% agar. After incubation at 37° C., plaques were expanded by picking a single plaque and transferring to 2 mls of LB media and grown overnight at 37° C. Single strand DNA was isolated using an M13 purification kit (Qiagen, Inc., Chatsworth, Calif.) per manufacturer's protocol, and clones containing the desired mutation were identified by sequencing the single stranded DNA using the Sequenase® sequencing kit (Amersham Life Sciences, Arlington Heights, Ill.) per manufacturer's protocol. IL-4 mutein cDNA from Replicative Form DNA corresponding to plaques containing the correct mutated sequence was isolated using Bam HI and Xha I, and subcloned to the plasmid vector pFastBac™1 (GibcoBRL, Gaithersburg, Md.). After subcloning, recombininant baculovirus DNA (hereafter referred to as Bacmid) was generated by transforming pFastBac™1 containing the mutein cDNA to the *E. coli* strain DH10Bac™ (GibcoBRL, Gaithersburg, Md.) as described by the manufacturer. Muteins were expressed in Spodoptera frugiperda (S*f*) 9 cells using the Bac-to-Bac (GibcoBRL, Gaithersburg, Md.) baculovirus expression system. All insect cell incubations occurred at 28° C. Briefly, 2 ml cultures of Sη9 cells were transfected with 5 μl of recombinant Bacmid using CellFECTIN (GibcoBRL, Gaithersburg, Md.). The supernatant was harvested 60 hours post-transfection, and used to infect a 100–200 ml culture of

```
R121A:            CTAAAGACGA TCATGGCTGA GAAATATT        (SEQ ID NO:24)

R121D:            GCTAAAGACG ATCATGGACG AGAAATATTC      (SEQ ID NO:25)

R121E:            GCTAAAGACG ATCATGGAAG AGAAATATTC      (SEQ ID NO:26)

R121F:            CTAAAGACGA TCATGTTTGA GAAATATT        (SEQ ID NO:27)

R121H:            CTAAAGACGA TCATGCACGA GAAATATT        (SEQ ID NO:28)

R121I:            CTAAAGACGA TCATGATAGA GAAATATT        (SEQ ID NO:29)

R121K:            CTAAAGACGA TCATGAAAGA GAAATATT        (SEQ ID NO:30)

R121N:            CTAAAGACGA TCATGAACGA GAAATATT        (SEQ ID NO:31)

R121P:            GCTAAAGACG ATCATGCCAG AGAAATATTC      (SEQ ID NO:32)

R121T:            CTAAAGACGA TCATGACTGA GAAATATT        (SEQ ID NO:33)

R121W:            CTAAAGACGA TCATGTGGGA GAAATATT        (SEQ ID NO:34)

Y124A:            ATCATGAGAG AGAAAGCATC AAAGTGTT        (SEQ ID NO:35)

Y124Q:            ATCATGAGAG AGAAACAATC AAAGTGTT        (SEQ ID NO:36)

Y124R:            ATCATGAGAG AGAAACGATC AAAGTGTT        (SEQ ID NO:37)

Y124S:            ATCATGAGAG AGAAATCATC AAAGTGTT        (SEQ ID NO:38)

Y124T:            ATCATGAGAG AGAAAACATC AAAGTGTT        (SEQ ID NO:39)

Y124A/S125A:      CGATCATGAG AGAAAGCT GCTAAGTGTT CGA    (SEQ ID NO:40)

T13D:             CAGGAGATCA TCAAAGATTT GAACAGCC        (SEQ ID NO:41)

R121T/E122F/Y124Q: GCTAAAGACG ATCATGACCT TCAAACAGTC AAAG (SEQ ID NO:42)
```

1×10⁶ Sf9 cells/ml in Grace's media (GibcoBRL, Gaithersburg, Md.). Per manufacturer's protocol, the supernatants were harvested 48–60 hrs post-infection by centrifugation at 5000 rpm for 10 minutes in a Sorvall® RC-5B centrifuge using a GSA rotor (Dupont Instument Co., Willmington, Del.) and assayed for virus titre (typically, >1×10⁸ plaque forming units/ml was obtained). For protein production, 2–3×10⁶ Sf9 cells/ml in 500 mls of SF900 II media (GibcoBRL, Gaithersburg, Md.) were infected at a multiplicity of infection between 4–10 and the supernatant was harvested 60–72 hrs post-infection by centrifugation at 5000 rpm for 10 minutes in a Sorvall® RC-5B centrifuge using a GSA rotor (Dupont Instrument Co., Willmington, Del.) and filtered through a sterile 0.2 μM filter unit.

Example 2

Purification of Muteins

Anti-human IL-4 monoclonal antibodies C400.1 and C400.17 were generated using standard protocols from mice using recombinant human IL-4 (Genzyme Diagnostics, Cambridge, Mass.) as immunogen, were produced as ascites fluid, purified, and coupled to CNBr-activated Sepharose (Pharmacia, Uppsala, Sweden) as per manufacturer's protocol. Sf9 cell supernatants generated from infection of Sf 9 cells by recombinant baculovirus containing the respective IL-4 mutein were loaded onto a 1 ml column of IL-4 affinity matrix, washed with 100 mM $NaHCO_3$, 500 mM NaCl, pH 8.3, washed with water to remove salt, and eluted with 8 column volumes of 100 mM Glycine, pH 3.0. Fractions were collected in siliconized vials containing 0.1 volume 1M Tris, pH 8.0. Mutein protein was firther purified by reverse phase chromatography using a Dynamax®-300 Å $C_{18}$ column (Rainin Instrument Co., Woburn, Mass.) with a 0–100% gradient of Buffer A to B (Buffer A, water; Buffer B, acetonitrile, 0.1% trifluoroacetic acid). Fractions were evaluated by SDS-PAGE, and mutein containing fractions were lyophilized for storage, and resuspended in sterile phosphate-buffered saline for assays. Mutein so purified was typically a single band as observed by SDS-PAGE (silver stain), and was quantitated by amino acid analysis (accuracy typically >90%).

Example 3

1° T Cell Proliferation Assay

Primary T cells were obtained from fresh blood from normal donors and purified by centrifugation using Ficoll-Paque® Plus 5 (Pharnacia, Upsalla, Sweden) essentially as described by Kruse, N., Tony, H. P. and Sebald, W. "Conversion of human interleukin-4 into a high affinity antagonist by a single amino acid replacement", *Embo J.* 11: 3237–44 (1992). The purified peripheral blood mononuclear cells were incubated for 7 days with 10 μg/ml phytohemagglutinin (Sigma Chemical Co., St. Louis, Mo.), harvested by centrifigation, and washed in RPMI 1640 media (GibcoBRL, Gaithersburg, Md.). 5×10⁴ activated T cells/well (PHA-blasts) were incubated with varying amounts of IL-4 or mutein in RPMI 1640 media containing 10% fetal bovine serum, 10 mM HEPES, pH 7.5, 2 mM L-glutamine, 100 units/ml penicillin G, and 100 μg/ml streptomycin sulphate in 96 well plates for 72 hrs at 37° C., pulsed with 1 μCi ³H-thymidine (DuPont NEN®, Boston, Mass.)/well for 6 hrs, harvested, and radioactivity was measured in a TopCount™ scintillation counter (Packard Instrument Co., Meriden, Conn.).

Example 4

HUVEC IL-6 Secretion Assay

Human umbilical vein endothelial cells (HUVEC) were obtained from Clonetics® Corp. (San Diego, Calif.), and maintained as per supplier's protocols. Cells (passage 3 to 6) were harvested by incubation with Trypsin/EDTA, washed, and plated at subconfluent densities in 48-well plates in EGM® media (Clonetics® Corp., San Diego, Calif.) containing bovine brain extract (BBE; Clonetics® Corp., San Diego, Calif.). At confluency (3–4 days at 37° C.), the media was removed and replaced with EGM® media without BBE. 24 hours later, varying concentrations of IL-4 or mutein was added to the cells in fresh EGM® without BBE, and allowed to incubate an additional 24 hrs. Supematants were harvested and the concentration of IL-6 was analyzed using a human IL-6 ELISA. The conditions were identical except for antagonist assays, varying concentrations of mutein were added to a constant concentration of 100 pM IL-4. Briefly, 96-well Immunolon® 2 plates (Dynatech Laboratories, Inc., Chantilly, Va.) were coated with 5 μg/ml anti-human IL-6 MAb Cat#1618-01 (Genzyme Diagnostics, Cambridge, Mass.) overnight at 4° C. Human IL-6 standard (Genzyme Diagnostics, Cambridge, Mass.) or samples were titrated in duplicate and incubated with the coated plate; after washes, secondary antibody rabbit anti-human IL-6 PAb (Caltag Laboratories, South San Francisco, Calif., Cat#PS-37) at a 1:1000 dilution was added. The presence of bound rabbit anti-IL-6 PAb was detected using alkaline phosphatase-coupled donkey anti-rabbit Ig PAb (Jackson ImmunoResearch Laboratories, Inc., West Grove, Pa., Cat#711-055-152) diluted 1:2000, and developed using pNPP (Sigma Chemical Co., St. Louis, Mo., Cat#N2770 or N1891). Absorbance was read at 405 nrn using a Vmax™ kinetic microplate reader (Molecular Devices Corp., Menlo Park, Calif.).

Example 5

Activities of Muteins

Table 1 summarizes the results of the muteins in the two assays described above. "$EC_{50}$, pM" is the effective concentration that produces a 50% maximal response measured in the concentration picomoles/liter. Activity is a function of both potency ($EC_{50}$) and maximal response ($R_{max}$). Cell-selective muteins exhibited differential activity of either a relative reduction in $R_{max}$ and/or a relative reduction in potency (increase in $EC_{50}$) in the HUVEC assay vs. the T cell assay. "$R_{max}$, % wt" is the maximal response measured relative to wild-type IL-4. By definition, wild-type IL-4 gives 100% response. All muteins were active in the T cell proliferation assay. Muteins R121D, R121E, R121P, and R121T/E122F/Y124Q were more potent than wild-type IL-4 in this assay, although mutein R121T/E122F/Y124Q had a reduced maximal response. Muteins Y124Q, Y124R, and Y124A/S125A had 2–3-fold increased $EC_{50}$ values than wild-type, as well as a reduced maximal response. However, they appear to retain a significant proportion of IL-4 activity on T cells. Muteins R121E, Y124Q and R121T/E122F/Y124Q had no measurable activity in the HUVEC assay, making them clearly T cell-selective, and thus selective for the IL-4 receptor expressed on T cells (IL-4Rα/IL-2Rγ). These muteins are IL-4 antagonists on endothelial cells because, although they interact normally with IL-4Rα, they do not activate the complex IL-4Rα/γ-like sub unit The muteins R121P and Y124R show activity in the HUVEC assay, but their $EC_{50}$ values are increased between 50–150-fold, and have reduced maximal responses relative to their ability to stimulate T cells. Although these two proteins do not appear to be absolutely T cell-selective, they are preferential for their activation of the T cell IL-4 receptor over the HUVEC IL-4 receptor.

TABLE 1

Muteins with preferential activity on T cells vs. endothelial cells

| Mutein | 1° T-cell proliferation | | HUVEC, IL-6 secretion | |
|---|---|---|---|---|
| | $EC_{50}$, pM | $R_{max}$, % wt | $EC_{50}$, pM | $R_{max}$, % wt |
| wildtype IL-4 | 150 | 100 | 20 | 100 |
| R121A | 150 | 100 | 20 | 65 |
| R121D | 100 | 40 | — | 0 |
| R121E | 65 | 100 | — | 0 |
| R121F | 150 | 100 | 20 | 60 |
| R121H | 150 | 80 | 40 | 70 |
| R121I | 100 | 100 | 40 | 50 |
| R121K | 150 | 100 | 100 | 75 |
| R121N | 150 | 100 | 35 | 50 |
| R121P | 100 | 100 | 650 | 45 |
| R121T | 150 | 100 | 20 | 75 |
| R121W | 150 | 100 | 80 | 35 |
| R121E/T13D | 100 | 100 | — | 0 |
| Y124A | 150 | 50 | 65 | 50 |
| Y124Q | 250 | 15 | 200 | 25 |
| Y124R | 750 | 30 | 250 | 25 |
| Y124S | 425 | 15 | 350 | 20 |
| Y124T | 300 | 15 | 350 | 35 |
| Y124A/S125A | 600 | 60 | 200 | 30 |
| R121T/E122F/Y124Q | 15 | 13 | — | 0 |

Example 6

Biological Response of IL-4 Muteins in HUVEC Assays

FIGS. 2A and B are a series of dose-response plots of HUVEC IL-6 secretion by the T cell-selective agonists relative to wild-type. IL-4 was included as an internal control on each plate used to assay mutein activity; a representative curve is shown. FIG. 4A is the dose-response curve for R121E versus wild-type L-4. Similarly, FIG. 4B–F are the dose-response curves for R121P, Y124Q, Y124R, Y124A/S125A, and R121T/E122F/Y124Q, respectively, versus wild-type IL-4. Activities have been normalized relative to the IL-4 control responses. Muteins R121E, Y124Q, and R121T/E122F/Y124Q demonstrate no activity in this assay. Muteins R121P and Y124R, though showing partial agonist activity in this assay, are relatively less potent to wild-type IL-4 than they are in the 1° T cell assay. Thus, despite their activity, they still demonstrate preferential activation of the T cell IL-4 receptor.

Example 7

Biological Response of IL-4 Muteins in 10 T Cell Assays

FIGS. 4A and B show dose-response curves of the T cell-selective agonist muteins in a representative assay using cells from a normal donor. IL-4 was included as an internal control on each plate used to assay mutein activity; a representative curve is shown. FIG. 6A is the dose-response curve for R121E versus wild-type IL-4. Similarly, FIG. 6B–F are the dose-response curves for R121P, Y124Q, Y124R, Y124A/S125A, and R121T/E122F/Y124Q, respectively, versus wild-type IL-4. Activities have been normalized relative to the IL-4 control responses. Muteins R121E, R121P, and R121T/E122F/Y124Q are more potent than wild-type IL-4, although R121T/E122F/Y124Q is only a partial agonist in this assay. Although not as potent as wild-type IL-4 in this assay, muteins Y124Q, Y124R, and Y124A/S125A are still effective partial agonists ($R_{max}$ values 60–70% of wild-type). In FIG. 6, activity is relative to the IL-4 response seen in the same plate for each mutein. Of particular note are muteins R121E and Y124Q, which show significant activity in the T cell assay yet no apparent activity in the HUVEC assay. Each of these muteins is a clear T cell-selective agonist.

Example 8

Antagonism of HUVEC IL-4-induced IL-6 Secretion by T Cell Selective Muteins

T cell-selective IL-4 muteins R121E (●) and Y124Q (▽), and the IL-4 antagonist R121D/Y124D (○) (FIG. 7), were titrated against a constant concentration of 100 pM IL-4. The IL-4 antagonist R121D/Y124D antagonizes IL-4 with a $K_I$ of ~1.5 nM under these conditions. HUVEC do not express IL-2Rγ, but do express the IL-4 receptor γ-like subunit. The substituted residues of R121E and Y124Q are in the D-helix of IL-4 and thus only affect interactions of IL-4 with IL-2Rγ (functional interaction) and the γ-like subunit (no or non-functional interaction), but do not affect the ability of these muteins to bind to IL-4Rα. Thus, the T cell-selective agonists R121E and Y124Q, by virtue of their ability to selectively interact with IL-2Rγ on T cells without promoting activation of the γ-like receptor sub unit on endothelial cells, are able to compete IL-4-induced responses on these endothelial cells ($K_I$ ~0.8–1 nM under these conditions). Such antagonism by T cell-selective IL-4 muteins may antagonize the effects of endogenously produced IL-4 on endothelial cells during T cell-directed therapy with said muteins.

Examples 9

Biological Response of IL-4 Mutein R121D.

The IL-4 mutein R121D (Arg-121 substituted with Asp) was generated as described and assayed in the 1° T cell and HUVEC assays. Referring to FIGS. 8A and 8B, data is shown for IL-4 (○) and R121D (●) in both the T cell (FIG. 8A) and the HUVEC (FIG. 8B) assays. In the T cell assay, R121D exhibited an $EC_{50}$ of ~100 pM and an $R_{max}$ value of ~60% relative to wild-type IL-4. It was inactive in the HUVEC assay ($EC_{50}$=●; $R_{max}$=○). These results demonstrate that the single substitution of Arg-121 of human IL-4 with Asp yields a protein that has selective activity on T cells, and lacks any apparent activity on endothelial cells. Although the mutein R121D is a partial agonist in the T cell assay, it is more potent than wild-type IL-4. However, like mutein R121E, R121D exhibits no activity in the HUVEC assay, demonstrating that it is a clear T cell-selective agonist.

Example 10

Biological Activity of IL-4 Mutein T13D/R121E.

The IL-4 mutein T13D/R121E (Thr-13 substituted with Asp together with Arg-121 substituted with Glu) was generated as described and assayed in the 1° T cell and HUVEC assays. Specifically with reference to FIGS. 9A–C, in the T cell assay (Panel A), T13D/R121E (▲) exhibited an $EC_{50}$ of ~100 pM, about 2–3-fold better than IL-4 (○) or R121E (Δ), and an $R_{max}$ value of 100% relative to IL-4. In HUVEC antagonist assays (Panel B), T13D/R121E (▲) was ~27-fold more potent an antagonist of IL-4 activity than R121E (Δ), exhibiting an $IC_{50}$ of ~2.2 nM vs. ~60 nM, respectively. The substitution of Thr-13 to Asp increases the potency of the T13D/R121E relative to R121E (both as an agonist in the T cell assay, and as an antagonist in the HUVEC assay), while the substitution Arg-121 to Glu confers T cell-selective activity to T13D/R121E (full agonist in the T cell assay, IL-4 antagonist in the HUVEC assay). In the HUVEC assay shown (Panel C), T13D/R121E (▲) exhibited nominal activity comparable to that seen with R121E (Δ). In this assay, measurement of monocyte chemoattractant protein 1 (MCP-1) in the media by ELISA was used instead of IL-6 to measure activity.

Example 11

Chimpanzee Toxicology and Immunopharmacology Study

Wild-type IL-4 ("wtIL-4") and IL-4[T13D/R121E] ("IL-4SA") were compared in a battery of tests in a two-phase study.

OBJECTIVE

The primary objective of this study was to determine whether IL-4SA has reduced toxicity relative to wtIL-4. A secondary objective was to determine whether the immunopharmacologic activity of wtIL-4 is similar to that of IL-4SA. Since very limited information was available prior to the start of the study regarding the in vivo effects of IL-4SA, both toxicity and immunomodulatory responses were assessed using a large number of endpoints.

METHODS

IL-4SA was originally chosen for development on the basis of its receptor selectivity. Since chimpanzee was determined to be the only species in which IL-4SA was highly specific for the same IL-4 receptor subtypes as in humans, the chimpanzee was considered to be the only viable preclinical model for accurately predicting IL-4SA safety and pharmacology in man.

The safety pharmacology study was performed according to the FDA guidelines for GLP. The materials and methods are largely described in detail in Protocol 98-15 (on file with the Bayer Berkeley Preclinical Department). The test articles were IL-4SA mutein T13D/R121E (lot numbers 97253-22 and 98251-96-14) and wtIL-4 (lot numbers 96241-41 and 723-1/95). The in-life portion of the study took place at New Iberia Research Center ("NIRC," New Iberia, La.) and involved 16 young adult to adult male and female chimpanzees with body weights that ranged from about 35 to 80 kg.

Table 2 provides an overview of the experimental design and indicates that the chimpanzees received once daily subcutaneous (s.c.) doses of test article for either 14 days (in Phase I) or 21 days (in Phase II). Following the cessation of dosing, the animals were continued on study for an additional 8-day period to determine if the effects caused by the test articule were reversible. Throughout the study, the animals were observed twice daily for any signs of reduced food consumption, behavioral abnormalities and general health.

TABLE 2

Overview of experimental design. In each of two portions of the study (Phase I and Phase II), there were four dose groups. The animals were dosed subcutaneously, once daily (between 8:00 and 10:00 a.m.), either for 14 days (in Phase I) or 21 days (in Phase II), then observed for an additional 8 days (the 'recovery phase' of each experiment). The treatment groups were as follows:

| Group Number | Number of Animals | Test Article | Dose ($\mu$g/kg) |
|---|---|---|---|
| Phase I | | | |
| 1 | 2 | wtIL-4 | 10 |
| 2 | 2 | Vehicle | NA |
| 3 | 2 | IL-4SA | 100 |
| 4 | 2 | IL-4SA | 10 |
| Phase II | | | |
| 1 | 2 | wtIL-4 | 30 |
| 2 | 2 | Vehicle | NA |
| 3 | 2 | IL-4SA | 300 |
| 4 | 2 | IL-4SA | 30 |

Whole blood, serum and plasma samples were analyzed by NIRC for a host of toxicity and immunomodulatory markers. The toxicity markers included a standard serum chemistry panel, a hematolgy panel covering complete blood counts, differentials and platelet counts, and coagulation profiling using assays for prothrombin time, activated partial prothrombin time, and fibrinogen. To assess immunomodulation, NIRC used fluorescence activated cell sorting (FACS) to follow a wide range of cell-associated proteins. These included markers tha allowed for demographic characterizations of the cellular populations (e.g., the percentage of total lymophocytes that were B cells) and markers that reflected phenotypic changes in immune cells (e.g., enhanced expression of cell-associated CD23).

In addition to assays performed at NIRC, the Bayer Berkeley Department of Preclinical Development and PPD Pharmaco (Richmond, Va.) analyzed plasma and serum samples for a wide range of responses that are typical of prolonged exposure to exogenous IL-4. These included antibodies against the IL-4 proteins (wtIL-4 and IL-4SA), test article concentrations in plasma before and after dosing, soluble IL-4 receptor (sIL-4R), soluble CD23, IgE, MCP-1, and endogenous LA-4.

RESULTS/DISCUSSION

A. Toxicity Endpoints

Wild type IL-4 was used in the study as a reference for comparing both the adverse and immunododulatory effects of IL-4SA. In humans, i.v. bolus administration of wtIL-4 at 20 $\mu$g/kg t.i.d. has been reported to result in reversible renal dysfunction, upper gastrointestinal tract bleeding, capillary leak syndrome, diarrhea, and carditis. Given the potential for this molecule to have severe toxicity, its dosage in the safety pharmacology study with chimpanzees was carefully selected in close consideration of published articles describing IL-4 toxicity in primates. The established dose for wtIL-4 in chimpanzees in the Phase I experiment, 10 $\mu$g/kg/day qd for 14 days was anticipated to result in clinically significant, but mild toxicity, with completely reversible clinical pathology. However, no clinically significant toxicity was statistically significant at this dose level, so the Phase II dose was increased to 30 $\mu$g/kg/day for wtIL-4.

Figure 10A:
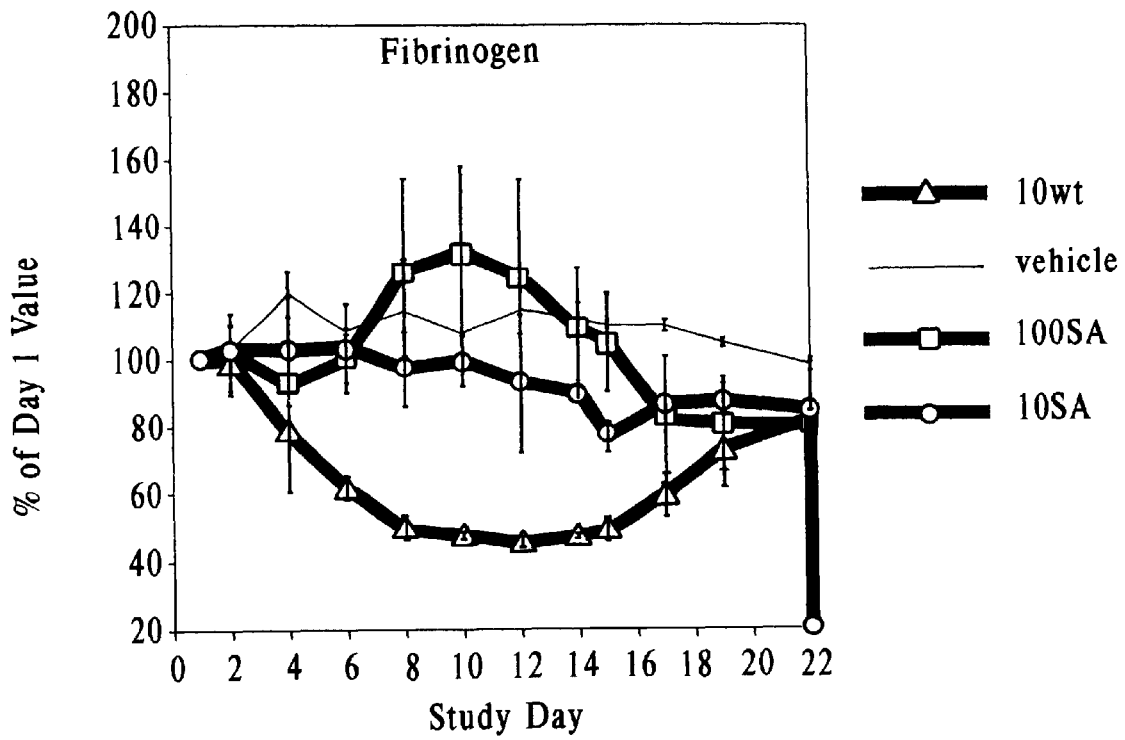
Figure 10B:
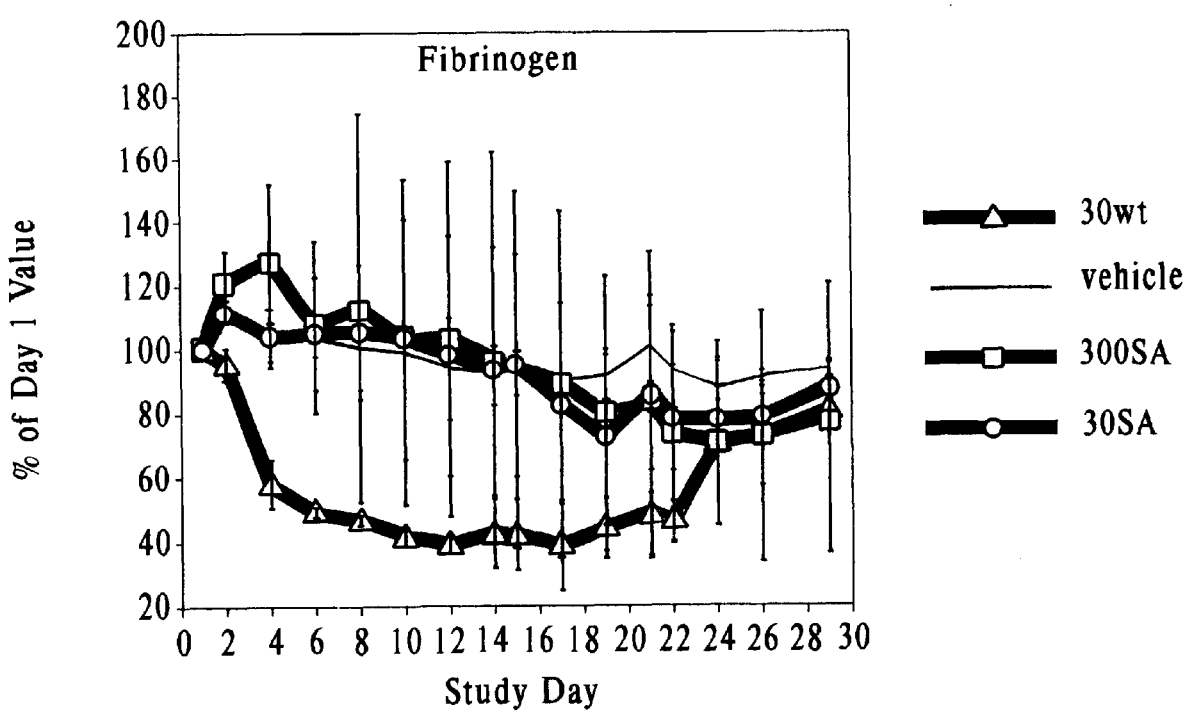
Figure 10C:
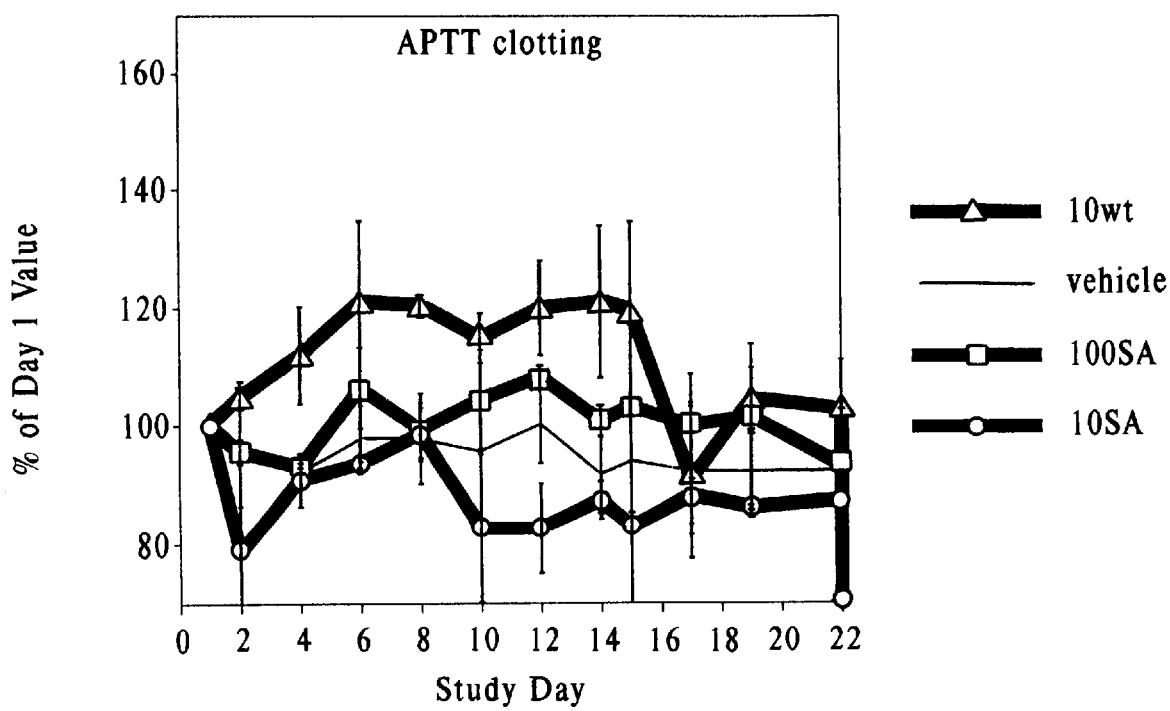
Figure 10D:
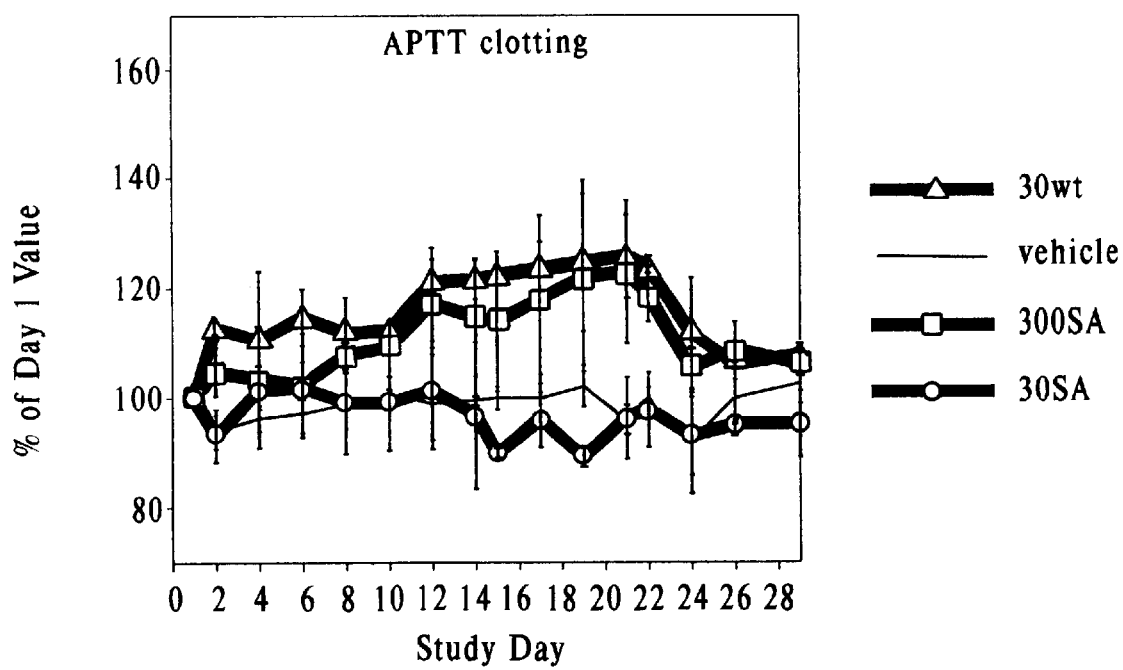

Although none of the changes in endpoints were of a magnitude that would constitute clinical significance, the coagulation parameters, fibrinogen and activated partial prothrombin time ("APTT"), showed clear treatment-related trends. Thus the greatest impact was seen with wtIL-4 at 10 μg/kg and no discernible effect was observed with IL-4SA at either 10 or 100 μg/kg (FIGS. 10A–10D). FIGS 10A through 10D show the change in Day 1 levels of fibrinogen and APTF as a function of exposure to test article. FIGS. 10A and 10B both show a deep reduction (50% or more) in fibrinogen production at the 30 μg/kg/day wtIL-4 dose, but no such reduction for either 30 or 300 μg/kg/day IL-4SA. FIGS. 10C and 10D also show increases in APTT at the 30 μg/kg/day wtIL-4 dose level of approximately 20%, while the 30 μg/kg/day IL-4SA dose shows little or no effect.

In contrast to the Phase I experiment, in which the twice-daily observations of the chimpanzees revealed no outwardly apparent toxicity, clinically significant events were observed in Phase II. These involved transient edema of the neck and face on day 14 with two animals, one dosed with 30 μg/kg wtIL-4 and the other with 300 μg/kg wtIL-4. The same animal from the 30 μg/kg wtIL-4 treatment later presented scrotal edema on day 20, which exacerbated on day 21 to include abdominal edema. The edema in this animal was sufficiently severe to warrant discontinuation of treatment with wtIL-4, but no action was ultimately taken since day 21 was the final day of dosing as prescribed by the protocol.

To rule out the possibility that differential effects observed in the toxicity wtIL-4 and IL-4SA were attributed to neutralization by antibodies against either of these proteins, assays were performed for IgG against both proteins. In the Phase I experiment, these assays showed that antibodies were not raised against either protein in any of the chimpanzees. In the Phase II experiment, antibody formation was confirmed in only two animals: one dosed with 300 μg/kg IL-4SA and one administered 30 μg/kg IL-4SA. However, these antibodies appeared fairly late in the study (starting on day 17), and therefore seem unlikely to account for a reduction in toxicity with IL-4SA during the first two weeks of the Phase II experiment.

B. Immunopharmacological Endpoints

Figure 11A:
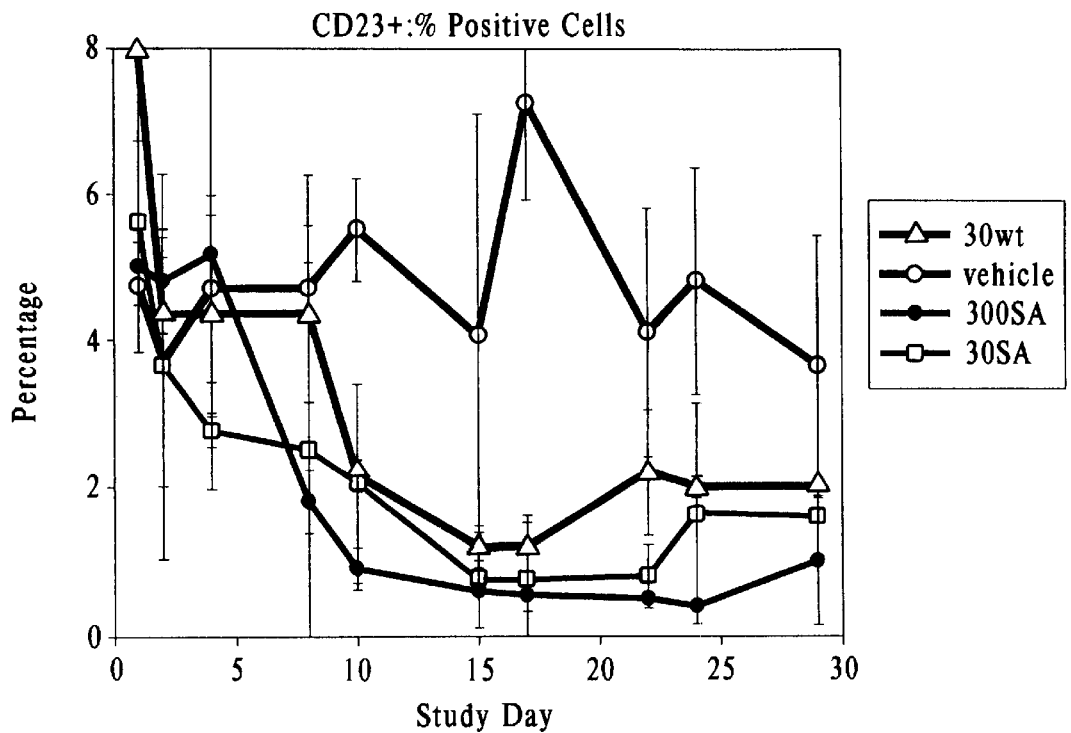
Figure 11B:
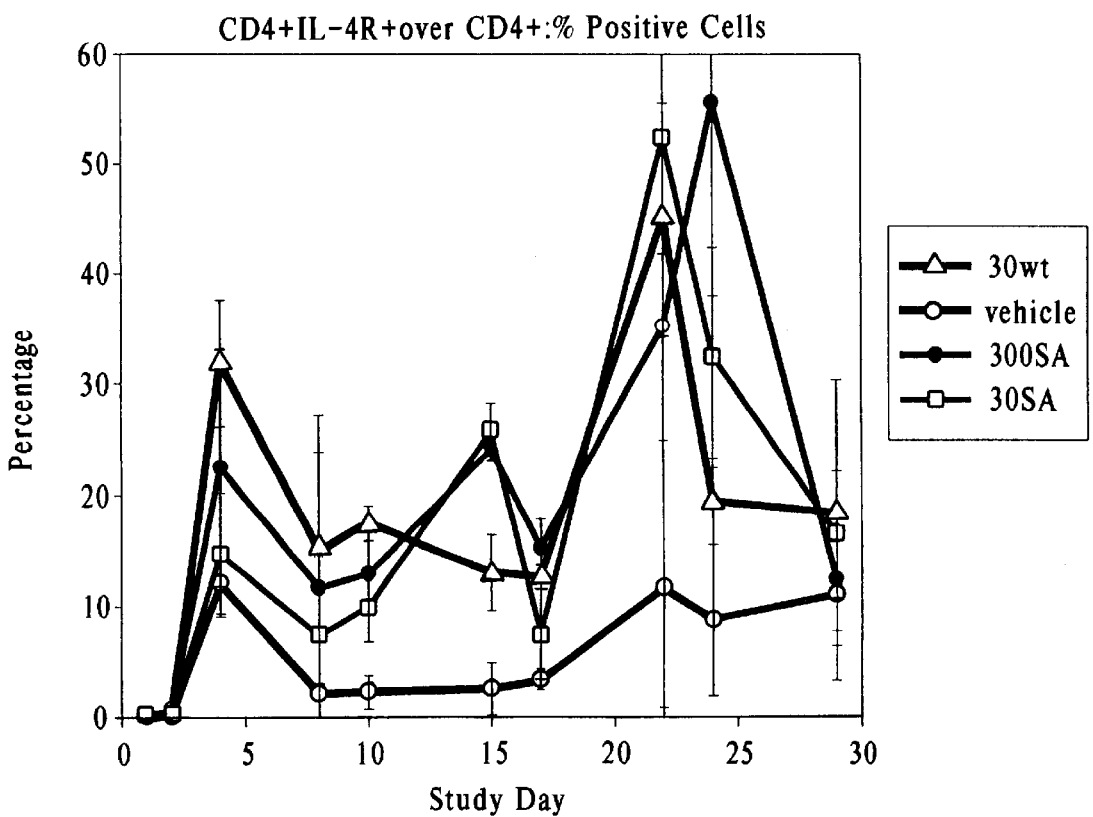
Figure 12A:
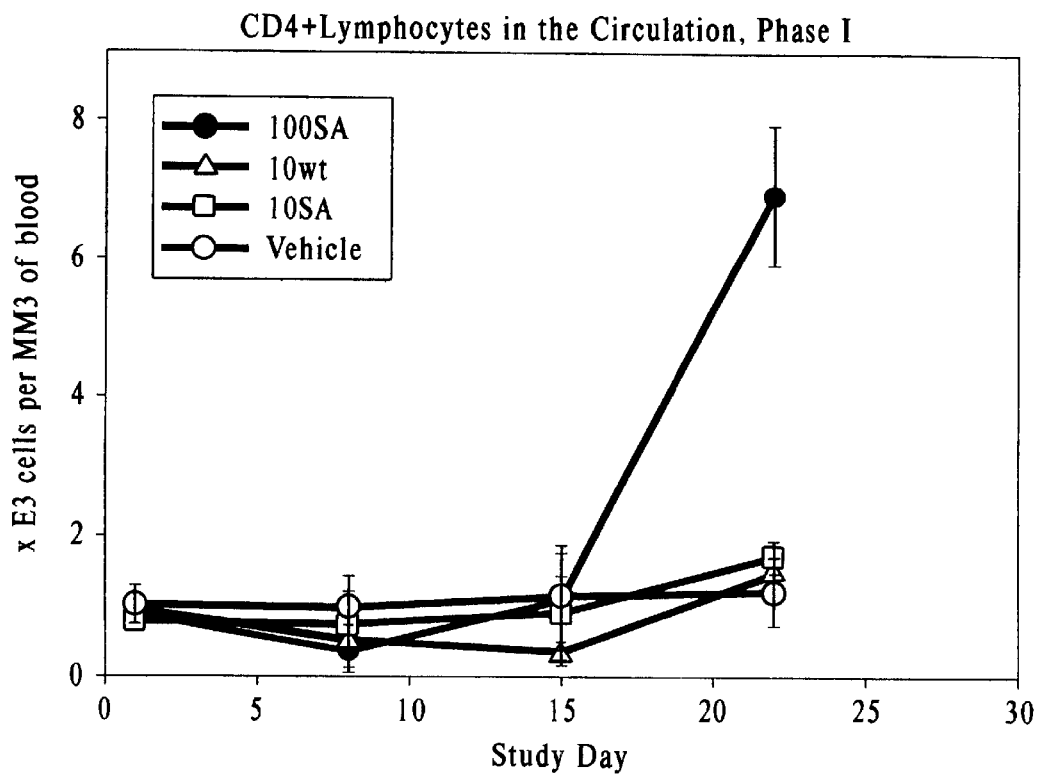
Figure 12B:
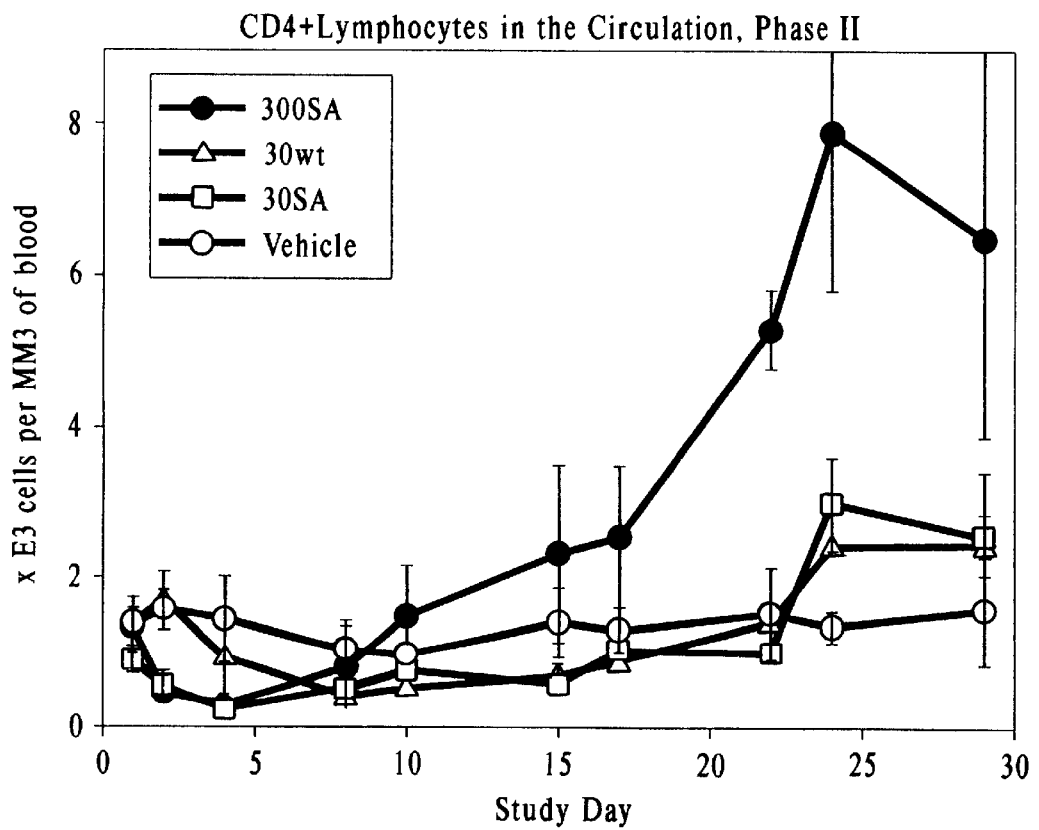
Figure 12C:
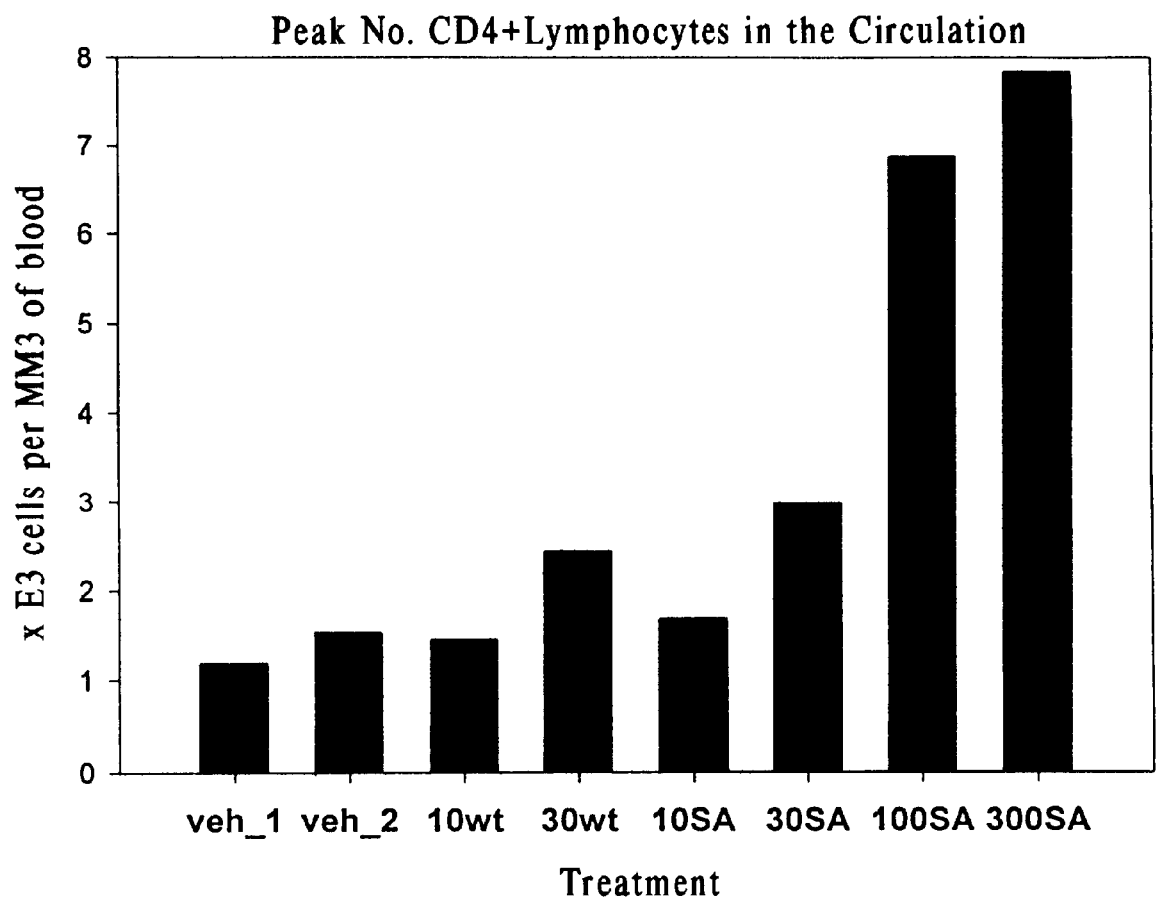

To assess immunopharmacologic activity, a wide range of responses was followed that are typical of prolonged exposure to exogenous IL-4. These included IL-4R, CD4 and CD23. The Phase II experiment showed that 30 ug/kg/day wtIL-4, 30 ug/kg/day IL-4SA and 300 ug/kg/day IL-4SA were roughly equipment at affecting the percentages of circulating lymphocytes staining positive for CD23 FIG. 11A) and CD4 plus IL-4R (FIG. 11B). However, the total number of circulating lymphocytes staining positive for CD4 alone showed a dose response relationship in which peak levels were greatest with 300 ug/kg/day IL-4SA (FIGS. 12A, 12B and 12C). Combined data from the Phase I and II experiments suggest that 30 ug/kg wtIL-4 was approximately equipment to 30 ug/kg IL-4SA at affecting the total number of circulating CD4 positive lymphocytes (FIG. 12C). These observations surrounding CD4 positive cells are noteworthy in that they indicate that IL-4SA is similar to wtIL-4 in affecting certain populations of T cells. Overall, the immunopharmacology data suggest that IL-4SA possesses many of the immunomodulatory properties of wtIL-4. These data serve to establish that the reduced toxicity observed with IL-4SA relative to wtIL-4 is not attributed to biological inertness. In conclusion, the experiments with chimpanzees showed that IL-4SA is significantly less toxic than wtIL-4, but has comparable potency in affecting certain populations of lymphocytes.

Example 12

Treatment of Multiple Sclerosis with IL-4 Selective Agonist

The use of an animal model as a predictor for pharmacological utility in humans is a well-accepted research tool. Initial testing of the IL-4 selective agonist for multiple sclerosis (MS) is conducted in a marmoset model using recombinant human IL-4 selective agonist protein. These studies are conducted to examine the effect of prophylactic and therapeutic treatment on disease induction and severity for both the acute symptomology as well as chronic relapsing-remitting disease.

Experimental autoimmune encephalomyelitis (EAE) is a CD4+ T cell-mediated autoimmune, inflammatory disease of the central nervous system. Induction of EAE is induced in marmosets (*C. jacchus*) weighing 300 to 400 gm by immunization with 200 mg of fresh-frozen postmortem human brain white matter homogenate (BH) emulsified with complete Freund's adjuvant (CFA) containing 3 mg/ml of killed *Mycobacterium tuberculosis* as described in Massacesi et al., Ann. Neurol., 37:519 (1995). On the day of immunization and again 2 days later, $10^{10}$ inactivated *Bordetella pertussis* organisms are diluted in 10 ml of saline solution and administered intravenously.

EAE is assessed by clinical and pathological criteria A standardized scoring system is employed to record the severity of clinical disease: 0=normal neurological findings; 1=lethargy, anorexia, weight loss; 2=ataxia, and either paraparesis/monoparesis, sensory loss, or brainstem syndrome including gaze palsy, or blindness; 3=paraplegia or hemiplegia; 4=quadriplegia.

Magnetic resonance imaging (MRI) has been shown to be a useful technique to characterize early as well as late immune mediated lesions of MS (Stewart et al., Brain, 114:1069 (1991). MRI is used to evaluate animals after immunization to monitor progression of disease over time. MRI data is collected on a Picker International NMR Cryogenic '2000' system, operating at a field strength of 0.15 Tesla; a receiver coil with an aperture of 15 cm to obtain the images. Multislice spin-echo and inversion-recovery pulse sequences are employed. Echo-delays times of either 40 and 60 ms, or 40 and 80 ms are used in the spin-echo sequences. In the inversion-recovery sequences the 180 –90 interpulse delay is 400 ms.

Marmosets are anesthetized with ketamine hydrochloride and placed in the scanner using a laser available for patient alignment such that the inner canthi of the eyes are aligned perpendicular to the direction of the static magnetic field. Animals are scanned before immunization and then daily from day 9 after immunization. Prior to scaning each day, animals are checked for signs of neurological impairment.

Animals are sacrificed at different times after immunization. The CNS is removed and fixed in 10% formalin. Paraffn sections of brain and spinal cord are prepared and stained with hematoxylin and eosin. Each coronal brain section or horizontal spinal cord section is analyzed for histopathological findings of inflammation and demyelination according to an arbitrary scale: inflammation; 0=no inflammation present, +=rare perivascular cuffs/average whole section; ++=moderate numbers of perivascular cuffs/section; may have meningeal inflammation; +++= widespread perivascular cuffing and parenchymal infiltration by inflammatory cells. Demyelination score; 0=no demyelination present; +=rare foci of demyelination; ++=moderate demyelination; +++=extensive demyelination with large confluent lesions.

For pretreatment studies on acute disease pathology, test drug is administered subcutaneously at a dosage range between 1 and 500 ug/kg following a dosing regimen of 1 administration per day to 1 administration per week prior to the onset of disease symptoms. For therapeutic intervention in existing disease, test article is administered subcutaneously at a dose range between 1 and 500 ug/kg following an extended dosing regimen of 1 treatment per day to 1 treatment per week over the course of several months.

Example 13

Treatment of Rheumatoid Arthritis

Rheumatoid arthritis (RA) is a debilitating inflamatory disease in which chronic activation of resident and infiltrating synovial cells causes destruction of cartilage and bone and leads to fibrosis and loss of function Cytokines released from activated T cells are thought to play a role in the maintenance of the chronic inflammatory reaction.

RA is induced in DBAII mice using type II collagen as described by Joosten et al., *Arthritis & Rheumatism*; 9:797 (1996). Collagen induced arthritis (CIA) is induced by immunniing mice via intradermal injection at the base of the tail with 100 ul of emulsion containing 100 ug of collagen. On day 21, animals are given a intraperitoneal booster injection of type II collagen (100 ug) dissolved in phosphate buffered saline (PBS).

Assessment of CIA is performed by examining the mice visually for the appearance of arthritis in the peripheral joints and scores for arthritis severity are assigned. Mice are considered to have arthritis when significant changes in redness and/or swelling is noted in the digits or in other parts of a minimum of 2 paws.

Clinical severity of arthritis is scored on a scale of 0–2 for each paw according to changes in redness and swelling (0=no change, 0.5=significant, 1.0=moderate, 1.5=marked and 2.0=severe maximal swelling and redness. Scoring is assessed by at least two blinded observers.

At the end of the study, some of the animals are sacrificed and paw and joint tissue is obtained for pathological and histopathology examination. The tissue is processed for immunohistochemical staining (frozen sections) or fixed and embedded in paraffin, sectioned and stained with H&E for analysis of cellular infiltration.

Evaluation of a murine analog of the IL-4 selective agonist of the present invention in the CIA model is performed with the use of a murine equivalent protein molecule. One of ordinary skill in the art is capable of comparing the marine IL-4 structure with the human IL-4 structure, generating parallel murine IL-4 muteins, and making any necessary adjustments based on responses in in vitro assays utilizing cell lines expressing either IL-4Rα/IL-2Rγ or IL-4Rα/γ-like sub unit in a manner analogous to that used for human IL-4 muteins with T cells and HUVEC. Animals are dosed one day prior to the booster administration of collagen and kept on a dosing regimen ranging between once a day to once a week for the duration of the study (40+ days). Animals are dosed with a range of concentrations of IL-4 selective agonist ranging between 1 to 100 ug/kg.

Example 14

Treatment of Insulin Dependent Diabetes Mellitus (IDDM)

There is some evidence in the literature of Th1 cell involvement in IDDM in humans and animal models of human disease. Nonobese diabetic (NOD) mice are utilized to examine the efficacy of a murine IL4 equivalent of IL-4 selective agonist in treating IDDM. One of ordinary skill in the art is capable of comparing the murine IL-4 structure with the human IL-4 structure, generating parallel murine IL-4 muteins, and making any necessary adjustments based on responses in in vitro assays utilizing cell lines expressing either IL-4Rα/IL-2Rγ or IL-4Rα/γ-like sub unit in a manner analogous to that used for human IL-4 muteins with T cells and HUVEC. Prediabetic NOD mice (approximately 7 wks) exhibit a proliferative unresponsiveness in vitro after T cell stimulation. The thning of this unresponsiveness is not related to insulitis and persists until the onset of diabetes which occurs at 24 wks of age.

Evaluation of the IL-4 selective agonist in NOD mice is conducted similar to studies reported by Rapoport et al., J. Exp Med; 178; p. 87 (1993). NOD mice are injected with test material at approximately 3 wks of age following a dosing regimen of once daily treatment or once a week treatment over the course of 12 weeks until the mice are 15 wks old. A control group of animals will receive treatment with a inert protein equivalent.

Mice will we tested for glycosuria using Tes-Tape and diagnosed for diabetes as determined by being glycosuria for at least two consecutive weeks. At the end of 52 wks, animals are sacrificed to obtain various organs and tissue for pathology evaluation. Tissue from the pancreas, submandibular salivary glands and kidney from each mouse is fixed and embedded in paraffin, sectioned and stained. Aldehyde fuchsin staining of pancreas sections is used to examine the extent to which insulitic infiltrates have reduced the mass of granulated β cells. Splenic leukocytes are counted by FAC-Scan analyses using anti-Thy-1.2, anti-CD4 and anti-CD8 mabs in ascites as described by Zipris et al., J. Immunol 146; p. 3763 (1991).

Other embodiments of the invention will become apparent to one of skill in the art. This invention teaches how to obtain muteins not specifically described herein but which have T cell activating ability and reduced endothelial cell activating ability, and thereby those muteins come within the spirit and scope of the invention. The concept and experimental approach described herein should be applicable to other cytokines utilizing heterologous multimeric receptor systems, in particular IL-2 and related cytokines (e.g. IL-7, IL-9 and IL-15), IL-10, interferon α, and interferon γ.

SEQUENCES

The following sequences are contained within this application:

SEQ ID NO: 1: hIL-4 (amino acid)
SEQ ID NO: 2: hIL-4 (amino acid, cDNA)
SEQ ID NO: 3: R121A (amino acid, cDNA)
SEQ ID NO: 4: R121D (amino acid, cDNA)
SEQ ID NO: 5: R121E (amino acid, cDNA)
SEQ ID NO: 6: R121F (amino acid, cDNA)
SEQ ID NO: 7: R121H (amino acid, cDNA)
SEQ ID NO: 8: R121I (amino acid, cDNA)
SEQ ID NO: 9: R121K (amino acid, cDNA)
SEQ ID NO: 10: R121N (amino acid, DNA)
SEQ ID NO: 11: R121P (amino acid, cDNA)
SEQ ID NO: 12: R121T (amino acid, cDNA)
SEQ ID NO: 13: R121W (amino acid, cDNA)
SEQ ID NO: 14: Y124A (amino acid, cDNA)
SEQ ID NO: 15: Y124Q (amino acid, cDNA)
SEQ ID NO: 16: Y124R (amino acid, cDNA)
SEQ ID NO: 17: Y121S (amino acid, cDNA)
SEQ ID NO: 18: R121T (amino acid, cDNA)
SEQ ID NO: 19: Y124A/S125A (a mino acid, cDNA)

SEQ ID NO: 20: T13D/R121E (amino acid, cDNA)
SEQ ID NO: 21: R121T/E122F/Y124Q (amino acid, cDNA)
SEQ ID NO: 22: 5' PCR Primer, IL-4
SEQ ID NO: 23: 3' PCR Primer, IL-4
SEQ ID NO: 24: Mutagenesis Primer for R121A
SEQ ID NO: 25: Mutagenesis Primer for R121D
SEQ ID NO: 26: Mutagenesis Primer for R121E
SEQ ID NO: 27: Mutagenesis Primer for R121F
SEQ ID NO: 28: Mutagenesis Primer for R121H
SEQ ID NO: 29: Mutagenesis Primer for R121I
SEQ ID NO: 30: Mutagenesis Primer for R121K
SEQ ID NO: 31: Mutagenesis Primer for R121N
SEQ ID NO: 32: Mutagenesis Primer for R121P
SEQ ID NO: 33: Mutagenesis Primer for R121T
SEQ ID NO: 34: Mutagenesis Primer for R121W
SEQ ID NO: 35: Mutagenesis Primer for Y124A
SEQ ID NO: 36: Mutagenesis Primer for Y124Q
SEQ ID NO: 37: Mutagenesis Primer for Y124R
SEQ ID NO: 38: Mutagenesis Primer for Y124S
SEQ ID NO: 39: Mutagenesis Primer for Y124T
SEQ ID NO: 40: Mutagenesis Primer for Y124A/S125A
SEQ ID NO: 41: Mutagenesis Primer for T13D
SEQ ID NO: 42: Mutagenesis Primer for R121T/E122F/Y124Q Note: for the T13D/R121E mutein, the primers SEQ ID NOs: 26 and 41 are used.

What is claimed is:

1. A polypeptide comprising a human IL-4 mutein numbered in accordance with wildtype IL-4, said mutein having the substitution R121E, wherein said substitution preserves native T cell activating ability but reduces endothelial cell activating ability on the resulting IL-4 mutein, relative to wild type.

2. A polypeptide comprising a human IL-4 mutein numbered in accordance with wild-type IL-4, said mutein having only both substitutions T13D and R121E, and any other conservative amino acid substitutions, wherein said substihions preserve native T cell activating ability but reduce endothelial cell activating ability on the resulting IL-4 mutein, relatve to wild type.

3. A pharmaceutical composition comprising the human IL-4 mutein of claim 1 in combination with a pharmaceutically acceptable carrier.

4. A pharmaceutical composition comprising the human IL-4 mutein of claim 2 in combination with a pharmaceutically acceptable carrier.

* * * * *